US012564636B2

(12) United States Patent
Wang et al.

(10) Patent No.: US 12,564,636 B2
(45) Date of Patent: Mar. 3, 2026

(54) PNICTOGEN-CONTAINING HETEROCYCLIC COMPOUNDS AND THEIR USE

(71) Applicants: University of Rhode Island Board of Trustees, Kingston, RI (US); Colgate University, Hamilton, NY (US)

(72) Inventors: Fang Wang, Saunderstown, RI (US); Jacob M. Goldberg, Hamilton, NY (US); Bradley M. Lipka, Middletown, RI (US); Daniel S. Honeycutt, West Warwick, RI (US)

(73) Assignees: University of Rhode Island Board of Trustees, Kingston, RI (US); Colgate University, Hamilton, NY (US)

( * ) Notice: Subject to any disclaimer, the term of this patent is extended or adjusted under 35 U.S.C. 154(b) by 471 days.

(21) Appl. No.: 18/106,242

(22) Filed: Feb. 6, 2023

(65) Prior Publication Data

US 2024/0285772 A1 Aug. 29, 2024

Related U.S. Application Data

(60) Provisional application No. 63/324,058, filed on Mar. 26, 2022.

(51) Int. Cl.

| | |
|---|---|
| ***A61K 47/54*** | (2017.01) |
| ***C07D 213/61*** | (2006.01) |
| ***C07D 213/64*** | (2006.01) |
| ***C07D 213/68*** | (2006.01) |
| ***C07D 213/71*** | (2006.01) |
| ***C07D 213/76*** | (2006.01) |
| ***C07D 235/24*** | (2006.01) |
| ***C07D 235/28*** | (2006.01) |
| ***C07D 237/12*** | (2006.01) |
| ***C07D 239/30*** | (2006.01) |
| ***C07D 277/62*** | (2006.01) |

(52) U.S. Cl.

CPC .......... *A61K 47/545* (2017.08); *C07D 213/61* (2013.01); *C07D 213/64* (2013.01); *C07D 213/68* (2013.01); *C07D 213/71* (2013.01); *C07D 213/76* (2013.01); *C07D 235/24* (2013.01); *C07D 235/28* (2013.01); *C07D 237/12* (2013.01); *C07D 239/30* (2013.01); *C07D 277/62* (2013.01)

(58) Field of Classification Search

CPC .................................................... A61K 47/545

See application file for complete search history.

(56) References Cited

U.S. PATENT DOCUMENTS

| | | | |
|---|---|---|---|
| 4,283,397 | A | 8/1981 | Hannah |
| 9,181,297 | B1 | 11/2015 | Pentelute et al. |
| 2006/0052421 | A1 | 3/2006 | Welter et al. |
| 2011/0053987 | A1 | 3/2011 | Selph et al. |
| 2021/0206791 | A1 | 7/2021 | Buchwald et al. |
| 2021/0290772 | A1 | 9/2021 | Wolfe et al. |

FOREIGN PATENT DOCUMENTS

| | | | |
|---|---|---|---|
| WO | 2014052650 | A2 | 4/2014 |
| WO | 2016205798 | A1 | 12/2016 |

OTHER PUBLICATIONS

Adamczyk, "Kinetic Studies of Thiol-Reactive Heterocycles for Bioconjugation", University of Rhode Island, Department of Chemistry, Wang Group (2022).
Kubota et al., "Palladium Oxidative Addition Complexes for Peptide and Protein Cross-linking", J. Am. Chem. Soc., DOI: 10.1021/jacs.8b00172 (2018).
Lipka et al., "Rapid Electrophilic Cysteine Arylation with Puridinium Salts", Bioconjugate Chem., 33: 2189-2196 (2022).
Lipka et al., "Supporting Information: Rapid Electrophilic Cysteine Arylation with Pyridinium Salts", University of Rhode Island, Department of Chemistry (2022).
Lipka, "Electrophilic Cysteine Arylation using Pyridinium Salts", University of Rhode Island, Department of Chemistry, Wang Group (2022).
Tang et al., "Tunable Amine-Reactive Electrophiles for Selective Profiling of Lysine", Angew. Chem. Int. Ed., 61: e202112107 (2022).
Tang et al., "Tunable heteroaromatic azoline thioethers (HATS) for cysteine profiling", Chemical Science, 13: 763 (2022).
Wolfe et al., "Perfluoroaryl Bicyclic Cell-Penetrating Peptides for Delivery of Antisense Oligonucleaotides", Angew. Chem. Int. Ed., 57: 1-5 (2018).
Zou et al., "Convergent diversity-oriented side-chain macrocyclization scan for unprotected polypeptides", Organic Biomolecular Chemistry, 12(4): 566-573 (2014).
International Search Report for International Application No. PCT/US2023/012401 mailed Jun. 30, 2023.

*Primary Examiner* — Golam M Shameem
(74) *Attorney, Agent, or Firm* — Morse, Barnes-Brown & Pendleton, P.C.; Martin Z. Zhang

(57) ABSTRACT

Disclosed are pnictogen-containing heterocyclic compounds of Formula (I)

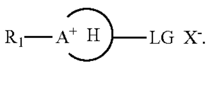

Each of $R_1$, the heterocyclic ring H, $A^+$, LG, and $X^-$ is defined herein. Also provided are methods of modifying a substrate using such a compound, conjugated biomolecules thus modified, and pharmaceutical compositions containing one of the conjugated biomolecules.

17 Claims, No Drawings

PNICTOGEN-CONTAINING HETEROCYCLIC COMPOUNDS AND THEIR USE

CROSS-REFERENCE TO RELATED APPLICATIONS

This application claims the benefit of priority based on U.S. Provisional Application No. 63/324,058, filed on Mar. 26, 2022, the content of which is incorporated herein by reference in its entirety.

BACKGROUND

Organic reagents are widely used for functionalizing biomolecules and other substrates containing chalcogens, including oxygen, sulfur, and selenium. For example, small molecule-based cysteine bioconjugation technology enables functionalization of proteins and peptides, which significantly expands the chemical space of biomacromolecules. Among various bioconjugation methods, nucleophilic aromatic substitution ($S_NAr$) of chalcogen-containing residues and the subsequent transformations of these substituted products have been broadly employed.

Despite a broad spectrum of reagents allowing for such transformations, no existing $S_NAr$ reactions are suitable for rapid conjugation of structurally complicated molecules to chalcogens of drugs, biomolecules, and nanomaterials at a second order reaction rate constant greater than 1 $M^{-1}\cdot s^{-1}$ in neutral aqueous media at an ambient temperature.

Known conventional reagents for chalcogen arylation suffer from three major disadvantages: (1) harsh reaction conditions, (2) slow reaction rates, and (3) limited synthetic modularity. Most known arylation methods are only suitable for relatively simple transformations in a non-aqueous medium at a high concentration. Arylation of chemically labile substrates (e.g., proteins and peptides) in a dilute solution has long been a formidable challenge.

There is a need to develop reagents and methods for arylation of chalcogen-containing substrates, especially biomolecules.

SUMMARY

To overcome the above-mentioned disadvantages in conventional nucleophilic chalcogen arylation, the present invention provides a novel method for rapid electrophilic chalcogenide arylation using pnictogen-containing heterocyclic electrophiles (CAP), each of which contains at least one positively charged quaternary pnictogen atom (e.g., nitrogen and phosphorus) and at least a leaving group.

A CAP is usually obtained from quaternizing a parental heterocyclic compound and thus converting it from a rather inert, hydrophobic electrophile into a highly reactive, hydrophilic reactant. Not to be bound by any theory, quaternization provides at least two benefits. First, the quaternization of the pnictogen atom introduces a positively charged center to the compound, which increases its polarity and in turn improves its water solubility. Second, the quaternized pnictogen atom increases the affinity of a CAP toward a nucleophilic substrate and thus the reactivity of a CAP as compared to its parent compound. Indeed, high reactivities were observed in all exemplary CAPs shown below.

Further, the prominent electron-withdrawing ability of quaternary pnictogen atoms facilitates effective activation of $S_NAr$ electrophiles without the need of introducing electron-withdrawing groups (EWGs), a strategy frequently adopted by conventional $S_NAr$-based chalcogen arylations. As such, extra handles can be accommodated on CAPs for further synthetic modifications. In light of the vast availability of substituted heterocyclic compounds, the described pnictogenium-based strategy, as a highly modular toolbox, provides a clear advantage over known nucleophilic chalcogen arylation chemistry.

In addition, CAPs are not only useful for functionalization of chalcogen-containing biomolecules but also applicable to modification of other chalcogen-bearing materials, such as thiol-decorated nanoparticles.

In one aspect, this invention relates to compounds of formula (I):

(I)

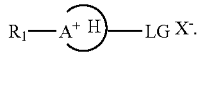

In this formula, $R_1$ is $C_1$-$C_6$ alkyl, $C_4$-$C_{10}$ cycloalkyl, 5- to 8-membered heterocycloalkyl, aryl, or heteroaryl;

is a heterocyclic ring (i.e., heterocyclic ring H);

- $A^+$ is a cationic quaternary pnictogen atom, preferably $N^+$;
- LG is a leaving group selected from the group consisting of halogen, aryloxy, $R_aO_2S$—, $R_bO_2S$—O—, $R_cOS$—, $R_dS(O)(NSO_2R_e)$—, $R_fS(O)(N^+(CH_3)_2)$—, cyano, nitro, aryloxy, heteroaryloxy, $R_iR_hS^+$—, and $R_kR_jS^+(O)$—, each of $R_a$, $R_b$, $R_c$, $R_d$, $R_e$, $R_f$, $R_h$, $R_i$, $R_j$, and $R_k$, independently, being $C_1$-$C_6$ alkyl, aryl, heteroaryl, halogen, alkoxy, or aryloxy, preferably being $C_1$-$C_6$ alkyl, aryl, or heteroaryl;
- $X^-$ is a counter anion selected from the group consisting of halide (e.g., $F^-$ and $I^-$), polyhalide anion, perchlorate, hydroxide, peroxide, siloxide, sulfate, hydrogen sulfate, sulfite, disulfite, dithionate, dithionite, halosulfate, thiosulfate, persulfate, disulfate, sulfinate ($R'SO_2^-$), sulfonate ($R''SO_3^-$), bis(sulfonyl)imide ($(R'SO_2)_2N^-$), nitrate, nitrite, azide, cyanide, cyanate, thiocyanate, phosphate, metaphosphate, polyphosphate, hydrogen phosphate, dihydrogen phosphate, monohalophosphate, dihalophosphate, hexahalophosphate, organophosphonate ($R'P(O)(O^-)_2$ or $R'P(O)(OR'')(O^-)$), organophosphate ($R'OP(O)(O^-)_2$ or $R'OP(O)(OR'')(O^-)$), arsenate, alkoxide, alkenoxide, aryloxide, carboxylate, percarboxylate, carbonate, bicarbonate, oxalate, borate, tetrahaloborate, tetraalkylborate, tetraarylborate, carborane, and combinations thereof, each of R' and R'', independently, being $C_1$-$C_6$ alkyl or aryl; and
- the number of net negative charges of $X^-$ equals to that of the net positive charges of

Some compounds of Formula (I) have two, three, four, or more leaving groups on heterocyclic ring H or, independently, on heterocyclic ring H or a different heterocyclic ring attached to heterocyclic ring H.

A subset of the compounds of Formula (I) are compounds of Formula (II):

(II)

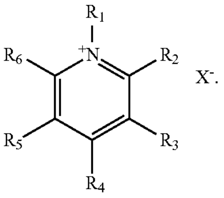

In this formula, $R_1$ and $X^-$ are defined above. Preferably, $R_1$ is $CH_3$ or $CH_2CH_3$ and $X^-$ is fluoride, iodide, or tetrafluoroborate.

In Formula (II) above, the cationic quaternary pnictogen atom is $N^+$;

each of $R_2$, $R_3$, $R_4$, $R_5$, and $R_6$, independently, is H, F, Cl, Br, I, $C_1$-$C_{10}$ alkoxy, $R_aO_2S$— (e.g., $CH_3O_2S$—), $R_bO_2S$—O— (e.g., $CH_3O_2S$—O—), $R_fS(O)(N^+(CH_3)_2)$— (e.g., phenyl-$S(O)(N^+(CH_3)_2)$—), halogenated aryl, halogenated heteroaryl, $Het^+$, or -L-$Het^+$, in which $Het^+$is

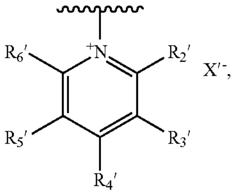

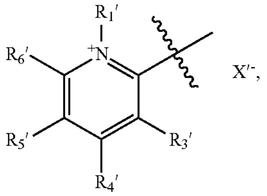

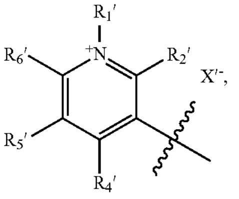

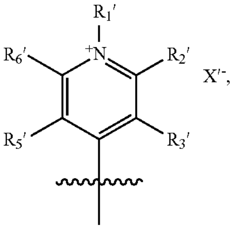

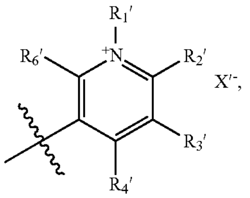

or

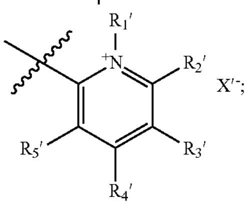

each of $R_a$ and $R_b$, independently, is $C_1$-$C_6$ alkyl (e.g., $CH_3$ and $CH_2CH_3$), or aryl (e.g., phenyl), $R_1$' is $CH_3$ or $CH_2CH_3$; each of $R_2$', $R_3$', $R_4$', $R_5$', and $R_6$', independently, is H, $NO_2$, F, Cl, Br, I, $R_a'O_2S$— (e.g., $CH_3O_2S$—), $R_b'O_2S$—O— (e.g., $CH_3O_2S$—O—), or $R_fS(O)(N^+(CH_3)_2)$— (e.g., phenyl-$S(O)(N^+(CH_3)_2)$—); each of $R_a$', $R_b$', and $R_f$', independently, is $C_1$-$C_6$ alkyl (e.g., $CH_3$ and $CH_2CH_3$) or aryl (e.g., phenyl); and $X^-$ is a counter anion selected from the group consisting of halide (e.g., $F^-$ and $I^-$), polyhalide anion, perchlorate, hydroxide, peroxide, siloxide, sulfate, hydrogen sulfate, sulfite, disulfite, dithionate, dithionite, halosulfate, thiosulfate, persulfate, disulfate, sulfinate ($R'SO_2$), sulfonate ($R''SO_3^-$), bis(sulfonyl) imide ($(R'SO_2)_2N^-$), nitrate, nitrite, azide, cyanide, cyanate, thiocyanate, phosphate, metaphosphate, polyphosphate, hydrogen phosphate, dihydrogen phosphate, monohalophosphate, dihalophosphate, hexahalophosphate, organophosphonate ($R'P(O)(O^-)_2$ or $R'P(O)(OR'')(O^-)$), organophosphate ($R'OP(O)(O^-)_2$ or $R'OP(O)(OR'')(O^-)$), arsenate, alkoxide, alkenoxide, aryloxide, carboxylate, percarboxylate, carbonate, bicarbonate, oxalate, borate, tetrahaloborate, tetraalkylborate, tetraarylborate, carborane, and combinations thereof, each of R' and R'', independently, being $C_1$-$C_6$ alkyl or aryl; L is a linker including $C_1$-$C_{20}$ alkyl, $C_2$-$C_{20}$ alkenyl, $C_2$-$C_{20}$ alkynyl, alkyl ether or polyether, aryl ether or polyether, oxygen, sulfur, sulfoxide, sulfone, aryl, heteroaryl, alkyl amino, and aryl amino with specific examples selected from the group consisting of

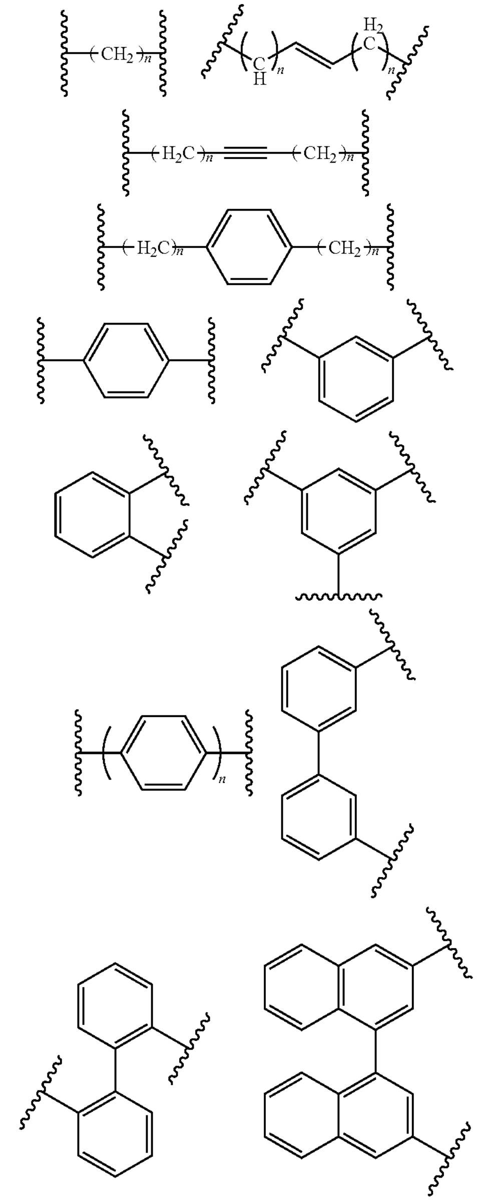

-continued

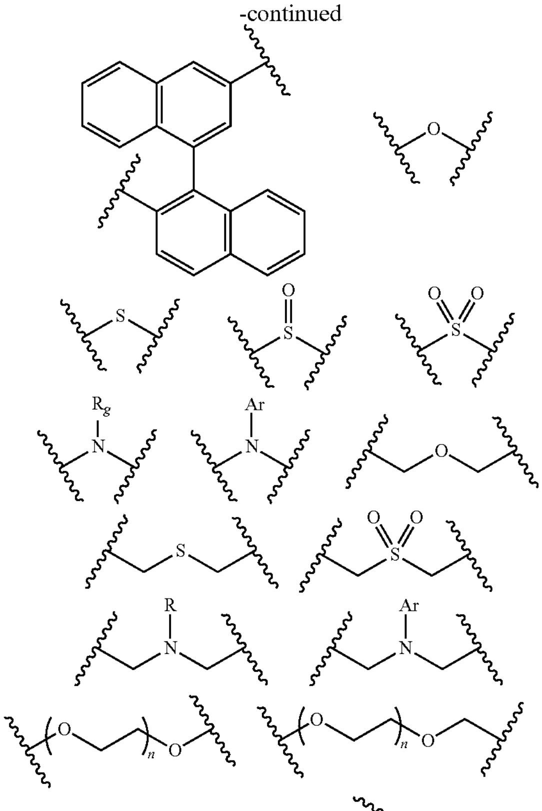

and

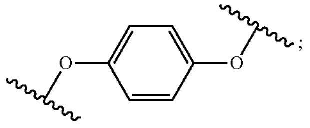

n is an integer from 0 to 20; $R_g$ is $C_1$-$C_6$ alkyl; and Ar is aryl;

at least one of $R_2$, $R_3$, $R_4$, $R_5$, and $R_6$ is the leaving group that is F, Cl, Br, I, $R_aO_2S$— (e.g., $CH_3O_2S$—), or $R_bO_2S$—O— (e.g., $CH_3O_2S$—O—);

when $R_2$ is F, (i) $R_4$ is F, Cl, Br, I, $C_1$-$C_{10}$ alkoxy, $R_aO_2S$— (e.g., $CH_3O_2S$—), or $R_bO_2S$—O— (e.g., $CH_3O_2S$—O—), (ii) $R_5$ is $NO_2$, or (iii) one and only one of $R_3$, $R_4$, $R_5$, and $R_6$ is $Het^+$;

when $R_2$ is Cl, $R_5$ is H or $Het^+$; and when $R_4$ is —$SO_2CH_3$, (i) $R_2$ is F, Cl, Br, I, $C_1$-$C_{10}$ alkoxy, $R_aO_2S$— (e.g., $CH_3O_2S$—), or $R_bO_2S$—O— (e.g., $CH_3O_2S$—O—), or (ii) one and only one of $R_2$, $R_3$, $R_5$, and $R_6$ is $Het^+$.

Another subset of the compounds of Formula (I) are compounds of Formula (III):

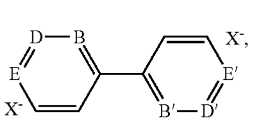

(III)

in which one and only one of B, D, and E is $N^+CH_3$ or $N^+CH_2CH_3$;

one and only one of B, D, and E is $CR_2$, $R_2$ being F, Cl, Br, I, $R_aO_2S$— (e.g., $CH_3O_2S$—), or $R_bO_2S$—O— (e.g., $CH_3O_2S$—O—) as a leaving group;

one and only one of B, D, and E is $CR_{11}$ (e.g., CH), $R_{11}$ being $C_1$-$C_6$ alkyl, $C_1$-$C_6$ alkoxy, $C_2$-$C_6$ alkenyl, $C_2$-$C_6$ alkynyl, $C_1$-$C_6$ alkyl amino, $C_4$-$C_{10}$ cycloalkyl, $C_4$-$C_{10}$ cycloalkoxy, 5- to 8-membered heterocycloalkyl, 5- to 8-membered heterocycloalkoxy, aryl, aryloxy, heteroaryl, or heteroaryloxy;

one and only one of B', D', and E' is $N^+CH_3$ or $N^+CH_2CH_3$;

one and only one of B', D', and E' is $CR_2'$, $R_2'$ being F, Cl, Br, I, $R_a'O_2S$— (e.g., $CH_3O_2S$—), or $R_b'O_2S$—O— (e.g., $CH_3O_2S$—O—) as a leaving group, and each of $R_a'$ and $R_b'$, independently, being aryl (e.g., phenyl) or $C_1$-$C_6$ alkyl (e.g., $CH_3$ and $CH_2CH_3$);

one and only one of B', D', and E' is $CR_{11}'$ (e.g., CH), $R_{11}'$ being $C_1$-$C_6$ alkyl, $C_1$-$C_6$ alkoxy, $C_2$-$C_6$ alkenyl, $C_2$-$C_6$ alkynyl, $C_1$-$C_6$ alkyl amino, $C_4$-$C_{10}$ cycloalkyl, $C_4$-$C_{10}$ cycloalkoxy, 5- to 8-membered heterocycloalkyl, 5- to 8-membered heterocycloalkoxy, aryl, aryloxy, heteroaryl, or heteroaryloxy;

$X^-$ is defined above; and $X'^-$ is a counter anion selected from the group consisting of halide (e.g., $F^-$ and $I^-$), polyhalide anion, perchlorate, hydroxide, peroxide, siloxide, sulfate, hydrogen sulfate, sulfite, disulfite, dithionate, dithionite, halosulfate, thiosulfate, persulfate, disulfate, sulfinate ($R'SO_2^-$), sulfonate ($R''SO_3^-$), bis(sulfonyl)imide ($(R'SO_2)_2N^-$), nitrate, nitrite, azide, cyanide, cyanate, thiocyanate, phosphate, metaphosphate, polyphosphate, hydrogen phosphate, dihydrogen phosphate, monohalophosphate, dihalophosphate, hexahalophosphate, organophosphonate ($R'P(O)(O^-)_2$ or $R'P(O)(OR'')(O^-)$), organophosphate ($R'OP(O)(O^-)_2$ or $R'OP(O)(OR'')(O^-)$), arsenate, alkoxide, alkenoxide, aryloxide, carboxylate, percarboxylate, carbonate, bicarbonate, oxalate, borate, tetrahaloborate, tetraalkylborate, tetraarylborate, carborane, and combinations thereof, each of R' and R'', independently, being $C_1$-$C_6$ alkyl or aryl.

A further subset of the compounds of Formula (I) are compounds of Formula (IV):

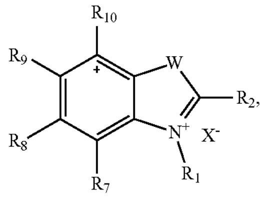

(IV)

in which $R_1$ is $CH_3$ or $CH_2CH_3$;

$R_2$, a leaving group, is $R_aO_2S$— (e.g., $CH_3O_2S$—), or $R_bO_2S$—O— (e.g., $CH_3O_2S$—O—);

each of $R_7$, $R_5$, $R_9$, and $R_{10}$, independently, is H or $C_1$-$C_6$ alkyl; and W is S or $NR_{11}$, $R_{11}$ being $C_1$-$C_6$ alkyl.

In this formula, $R_1$ and $X^-$ are defined above.

Still another subset of the compounds of Formula (I) are compounds of Formula (V):

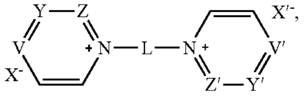

(V)

in which one and only one of V, Y, and Z is $CR_2$, $R_2$ being F, Cl, Br, I, $R_aO_2S$— (e.g., $CH_3O_2S$—), or $R_bO_2S$—O— (e.g., $CH_3O_2S$—O—) as a leaving group;

the other two of V, Y, and Z is $CR_{11}'$ (e.g., CH), $R_{11}'$ being $C_1$-$C_6$ alkyl, $C_1$-$C_6$ alkoxy, $C_2$-$C_6$ alkenyl, $C_2$-$C_6$ alkynyl, $C_1$-$C_6$ alkyl amino, $C_4$-$C_{10}$ cycloalkyl, $C_4$-$C_{10}$ cycloalkoxy, 5- to 8-membered heterocycloalkyl, 5- to 8-membered heterocycloalkoxy, aryl, aryloxy, heteroaryl, or heteroaryloxy;

one and only one of V', Y', and Z' is $CR_2'$, $R_2'$ being F, Cl, Br, I, $R_a'O_2S$— (e.g., $CH_3O_2S$—), or $R_b'O_2S$—O— (e.g., $CH_3O_2S$—O—) as a leaving group;

the other two of V', Y', and Z' is $CR_{11}'$ (e.g., CH), $R_{11}'$ being $C_1$-$C_6$ alkyl, $C_1$-$C_6$ alkoxy, $C_2$-$C_6$ alkenyl, $C_2$-$C_6$ alkynyl, $C_1$-$C_6$ alkyl amino, $C_4$-$C_{10}$ cycloalkyl, $C_4$-$C_{10}$ cycloalkoxy, 5- to 8-membered heterocycloalkyl, 5- to 8-membered heterocycloalkoxy, aryl, aryloxy, heteroaryl, or heteroaryloxy;

L is a linker as defined above; and $X^-$ and $X^-$ are counter anions as defined above.

The compounds described above can have one or any combinations of the following features:

(i) $R_1$ is $CH_3$ or $CH_2CH_3$;

(ii) $X^-$ is fluoride, iodide, or tetrafluoroborate;

(iii) $X'^-$ is fluoride, iodide, or tetrafluoroborate;

(iv) in Formula (II), at least one of $R_2$, $R_4$, and $R_6$ is the leaving group; in Formulas (III) and (V), $R_2$ and $R_2'$ are the leaving groups; and in Formula (IV), $R_2$ is the leaving group;

(v) in Formula (II), $R_2$, being the leaving group, is $CH_3O_2S$—, $R_4$ is H, $C_1$-$C_{10}$ alkoxy, or $Het^+$, and/or $R_3$ or $R_5$ is $NO_2$; and (vi) in Formula (II), at most only one of $R_2$, $R_3$, $R_4$, $R_5$, and $R_6$ is $Het^+$ or -L-$Het^+$.

Each of alkyl, alkoxy, alkenyl, alkynyl, alkyl amino, cycloalkyl, heterocycloalkyl, heterocyclic ring, phenyl, aryl, aryloxy, heteroaryl, and heteroaryloxy is optionally substituted with one or more of deuterium, halogen (e.g., F), CN, oxo, $C_1$-$C_6$ alkyl, $C_3$-$C_6$ cycloalkyl, $C_1$-$C_6$ haloalkyl, $C_2$-$C_6$ alkenyl, $C_2$-$C_6$ alkynyl, —OR', —C(O)R', —C(O)OR', —O—COR', —C(O)NR'R", —NR'R", —SR', —SOR', —$S(O)_2R'$, or —POR'R", in which each of R' and R", independently, is H, halogen, $C_1$-$C_6$ alkyl, $C_1$-$C_6$ haloalkyl, $C_3$-$C_6$ cycloalkyl, 3-6 membered heterocycloalkyl, 5-10 membered heteroaryl, or 6 or 10 membered aryl.

Another aspect of this invention relates to a method for modifying a substrate. The method includes the steps of a) providing a substrate, and b) contacting the substrate with a pnictogen-containing heterocyclic compound as described above, thereby obtaining a conjugated substrate containing a substrate moiety derived from the substrate and a pnictogen-containing heterocyclic moiety derived from the pnictogen-containing heterocyclic compound. The substrate preferably contains a functional group selected from the group consisting of hydroxyl, thiol, selenol, and tellurol, and the substrate moiety is linked to the pnictogen-containing heterocyclic moiety via a covalent bond formed by replacing the leaving group in the pnictogen-containing compound with the O, S, Se, or Te atom in the functional group of the substrate.

In a preferred method, the pnictogen-containing heterocyclic compound is a compound of Formula (II):

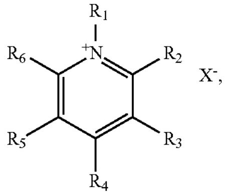

(II)

in which $R_1$ is $CH_3$, $CH_2CH_3$, or -L-$Het^+$;

each of $R_2$, $R_3$, $R_4$, $R_5$, and $R_6$, independently, is H, F, Cl, Br, I, $C_1$-$C_{10}$ alkoxy, $R_aO_2S$— (e.g., $CH_3O_2S$—), or $R_bO_2S$—O— (e.g., $CH_3O_2S$—O—), $Het^+$, or -L-$Het^+$, in which $R_a$, $R_b$, L, and $Het^+$ are as defined above; and at least one of $R_2$, $R_3$, $R_4$, $R_5$, and $R_6$ is the leaving group that is F, Cl, Br, I, $R_aO_2S$— (e.g., $CH_3O_2S$—), or $R_bO_2S$—O— (e.g., $CH_3O_2S$—O—).

The method described above can have one or any combination of the following features:

(i) at most only one of $R_2$, $R_3$, $R_4$, $R_5$, and $R_6$ is $Het^+$ or -L-$Het^+$, (ii) the contacting step is performed in a medium, (iii) the medium is water, (iv) the contacting step is performed in an aqueous medium having a pH of 2 to 10 (preferably, 3 to 9, and more preferably, 6 to 8), and (v) the substrate is a biomolecule selected from the group consisting of an amino acid, a peptide, a protein, a deoxyribonucleic acid or a derivative thereof, a ribonucleic acid or a derivative thereof, a peptoid, and poly(amino acid).

Also within the scope of this invention is a conjugated biomolecule comprising (i) a biomolecule moiety derived from a biomolecule, and (ii) a pnictogen-containing heterocyclic moiety derived from any pnictogen-containing heterocyclic compound described above, in which the biomolecule is an amino acid, a peptide, a protein, a deoxyribonucleic acid or a derivative thereof, a ribonucleic acid or a derivative thereof, a peptoid, or poly(amino acid), each having a functional group selected from the group consisting of hydroxyl, thiol, selenol, and tellurol, and the biomolecule moiety is linked to the pnictogen-containing heterocyclic moiety via a covalent bond formed by substitution of the leaving group in the pnictogen-containing heterocyclic compound by the functional group in the biomolecule.

The conjugated biomolecule can further contain a therapeutic moiety derived from a therapeutic agent selected from the group consisting of an anticancer agent, a therapeutically active peptide and protein, a medication for a neurological disorder, a molecular scaffold for targeted drug delivery, or a radioactive tracer, in which the therapeutic moiety is linked to the pnictogen-containing heterocyclic moiety via a covalent bond. Preferably, the therapeutic agent contains a functional group selected from the group consisting of hydroxyl, thiol, selenol, and tellurol, and the pnictogen-containing heterocyclic compound has two leaving groups.

Still within the scope of this invention is a pharmaceutical composition containing any of the conjugated biomolecule described above and a pharmaceutically acceptable carrier thereof. The conjugated biomolecule is present at an effective amount for treating a condition or disorder in a subject.
Table 1 below shows 31 exemplary CAP compounds of the present invention, namely, CAP1-a, CAP1-b, CAP1-F, CAP1-$N_3$, CAP1-CCH, and CAP2-CAP27.
TABLE 1
| | |
|---|---|
| 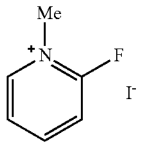 | 1-a |
| 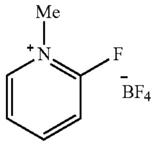 | 1-b |
| 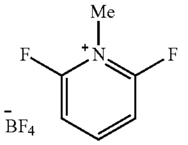 | 1-F |
| 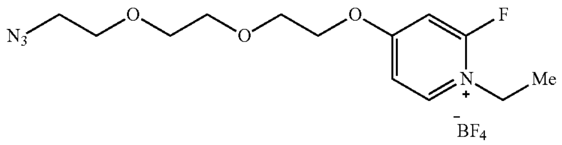 | 1-$N_3$ |
| 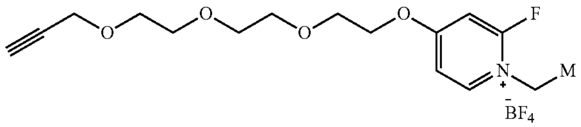 | 1-CCH |
| 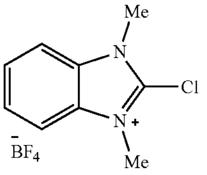 | 2 |
| 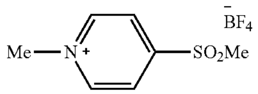 | 3 |
| 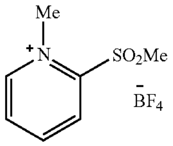 | 4 |
| 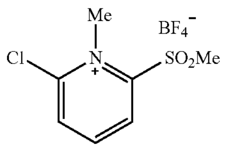 | 5 |

TABLE 1-continued
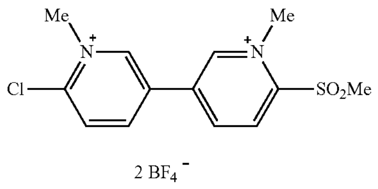 [SMILES: C[n+]1cc(-c2ccc(S(C)(=O)=O)[n+](C)c2)ccc1Cl]
6
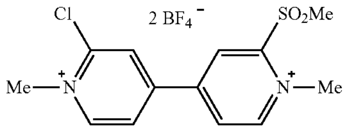 [SMILES: C[n+]1ccc(-c2cc[n+](C)c(S(C)(=O)=O)c2)cc1Cl]
7
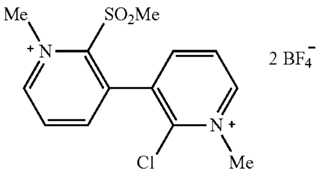 [SMILES: C[n+]1cccc(-c2ccc[n+](C)c2S(C)(=O)=O)c1Cl]
8
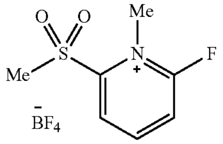
9
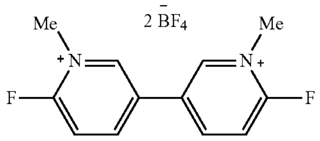 [SMILES: C[n+]1cc(-c2ccc(F)[n+](C)c2)ccc1F]
10
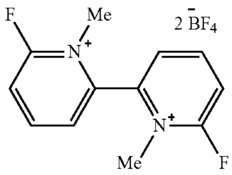 [SMILES: C[n+]1c(F)cccc1-c1cccc(F)[n+]1C]
11
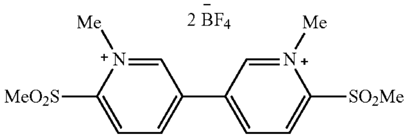 [SMILES: C[n+]1cc(-c2ccc(S(C)(=O)=O)[n+](C)c2)ccc1S(C)(=O)=O]
12
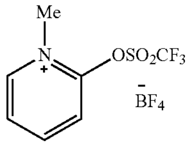
13
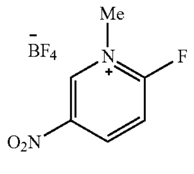 [SMILES: "BF4" ; C[n+]1cc([N+](=O)[O-])ccc1F]
14

TABLE 1-continued
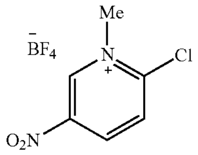 [SMILES: "BF4" ; C[n+]1cc([N+](=O)[O-])ccc1Cl]
15
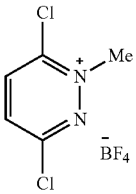
16
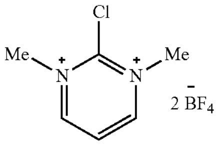
17
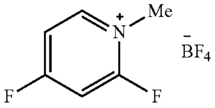
18
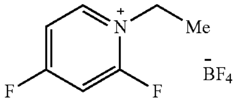
19
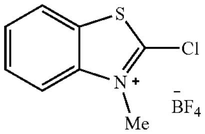
20
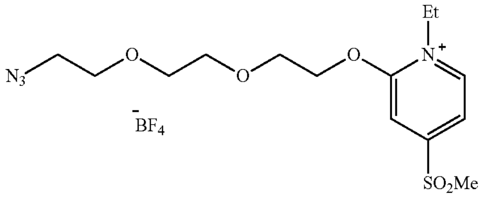
21
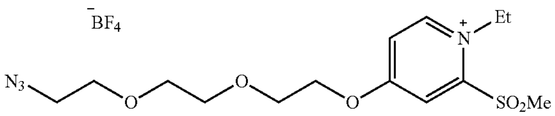 [SMILES: CC[n+]1ccc(OCCOCCOCCN=[N+]=[N-])cc1S(C)(=O)=O ; "BF4"]
22
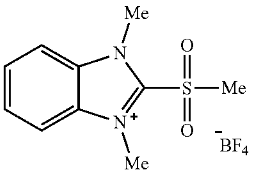
23

TABLE 1-continued

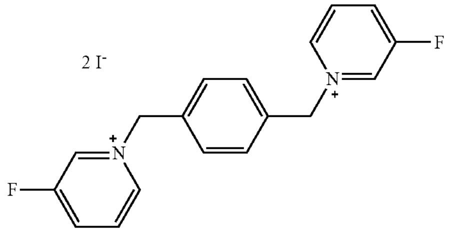 [SMILES: Fc1ccc[n+](Cc2ccc(C[n+]3cccc(F)c3)cc2)c1]

24

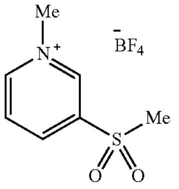

25

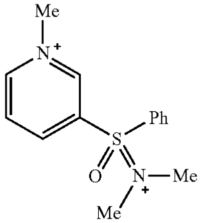 [SMILES: C[N+](C)=S(=O)(c1ccccc1)c1ccc[n+](C)c1]

26

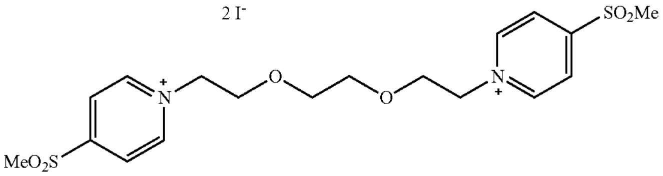 [SMILES: CS(=O)(=O)c1cc[n+](CCOCCOCC[n+]2ccc(S(C)(=O)=O)cc2)cc1]

27

Preferred compounds include Compounds 1-N3, 1-CCH, 4-14, 18, 19, and 21-27. More preferred compounds are Compounds 4-9, 21, and 22.

The term "chalcogen" herein refers a chemical element in group 16 of the periodic table including oxygen (O), sulfur (S), selenium (Se), and Tellurium (Te).

The term "pnictogen" refers to a chemical element in group 15 of the periodic table including nitrogen (N), phosphorus (P), arsenic (As), antimony (Sb), bismuth (Bi), and moscovium (Mc).

The term "halogen" herein refers to a fluoro (F), chloro (Cl), bromo Br), or iodo (I) radical. A particular halogen is a fluoro radical.

The term "alkyl" refers to a straight or branched hydrocarbon group, containing 1-20 carbon atoms (e.g., $C_{1-10}$, $C_{1-6}$, $C_{1-4}$, and $C_{1-3}$) and a monovalent radical center derived by the removal of a hydrogen atom from a carbon atom of a parent alkane. Exemplary alkyl groups are methyl, ethyl, n-propyl, isopropyl, n-butyl, iso-butyl, tert-butyl, n-pentyl, and n-hexyl. "Alkyl" includes "haloalkyl", which refers to alkyl substituted with one or more halogens (fluoro, chloro, bromo, or iodo). Examples include fluoromethyl, difluoromethyl, trifluoromethyl, fluoroethyl (e.g., 1-fluoroetyl and 2-fluoroethyl), difluoroethyl (e.g., 1,1-, 1,2-, and 2,2-difluoroethyl), and trifluoroethyl (e.g., 2,2,2-trifluoroethyl).

The term "alkoxy" refers to an —O-alkyl group. The terms "alkoxy" and "alkyl ether" are used interchangeably. Examples are methoxy, ethoxy, propoxy, and isopropoxy. Alkoxy also includes haloalkoxy, namely, alkoxy substituted with one or more halogens, e.g., —O—$CH_2Cl$ and —O—$CHClCH_2Cl$.

The term "cycloalkyl" refers to a nonaromatic, saturated or unsaturated monocyclic, bicyclic, tricyclic, or tetracyclic hydrocarbon group containing 3 to 12 carbons (e.g., $C_{3-10}$, $C_{3-8}$, $C_{4-7}$, and $C_{3-6}$). Cycloalkyl also includes fused, bridged, and spiro ring systems. Examples are cyclopropyl, cyclobutyl, cyclopentyl, cyclopentenyl, cyclohexyl, cyclohexenyl, cycloheptyl, cyclooctyl, bicyclo[1.1.1]pentyl, bicyclo[2.1.1]hexyl, bicyclo[2.1.1]heptyl, bicyclo[2.2.2]octanyl, and decahydronaphthalene. The term "cycloalkoxy" refers to —O— cycloalkyl.

The term "heterocycloalkyl" refers to a nonaromatic, saturated or unsaturated, 3-8 membered monocyclic, 8-12 membered bicyclic, or 11-14 membered tricyclic ring system having one or more heteroatoms (e.g., O, N, P, and S). The term also includes fused, bridged, and spiro ring systems. Examples include aziridinyl, azetidinyl, pyrrolidinyl, dihydrofuranyl, tetrahydrofuranyl, tetrahydropyranyl, tetrahydrothiophenyl, tetrahydro-2-H-thiopyran-1,1-dioxidyl, piperazinyl, piperidinyl, morpholinyl, imidazolidinyl, azepanyl, dihydrothiadiazolyl, dioxanyl, 2-azaspiro[3.3] heptanyl, quinuclidinyl, and 8-azabicyclo[3.2.1]octanyl. The term "heterocycloalkoxy" refers to an —O-heterocycloalkyl group.

The term "alkenyl" refers to a straight or branched, monovalent, unsaturated aliphatic chain having 2 to 20 carbon atoms (e.g., $C_{2-4}$, $C_{2-6}$, and $C_{2-10}$) and one or more carbon-carbon double bonds. Examples are ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, and 2-pentenyl. The term “alkenylene” refers to a straight or branched, bivalent, unsaturated aliphatic chain having 2 to 20 carbon atoms (e.g., $C_{2-4}$, $C_{2-6}$, and $C_2$ ) and one or more carbon-carbon double bonds.

The term “alkynyl” refers to a straight or branched aliphatic chain having 2 to 20 carbon atoms (e.g., $C_{2-4}$, $C_{2-6}$, and $C_2$ ) and one or more carbon-carbon triple bonds. Examples are ethynyl, 2-propynyl, 2-butynyl, 3-methylbutynyl, and 1-pentynyl. The term “alkynylene” refers to a straight or branched, bivalent, unsaturated aliphatic chain having 2 to 20 carbon atoms (e.g., $C_{2-4}$, $C_{2-6}$, and $C_2$ ) and one or more carbon-carbon triple bonds.

The term “aryl” refers a 6-carbon monocyclic, 10-carbon bicyclic, 14-carbon tricyclic aromatic ring system wherein each ring can have one or more (e.g., 1 to 10, 1 to 5, and 1 to 3) substituents. Examples include phenyl, biphenyl, 1- or 2-naphthyl, 1,2-dihydronaphthyl, 1,2,3,4-tetrahydronaphthyl, indenyl, and indanyl. The term “aryloxy” refers to —O-aryl. The term “halogenated aryl” refers to aryl substituted with one, two, three, or more halogen atoms. Examples include 2-fluorophenyl, 3-fluorophenyl, and 4-fluorophenyl.

The term “heteroaryl” refers to an aromatic 5-8 membered monocyclic, 8-12 membered bicyclic, or 11-14 membered tricyclic ring system having one or more heteroatoms (e.g., O, N, P, and S). Examples include pyridinyl, pyridinium, pyrimidinyl, quinolinyl, isoquinolinyl, indolyl, benzimidazolyl, benzoxazolyl, benzothiophenyl, benzofuranyl, pyrazolyl, triazolyl, oxazolyl, thiadiazolyl, tetrazolyl, oxazolyl, isoxazolyl, carbazolyl, furyl, imidazolyl, thienyl, quinolinyl, indolyl, thiazolyl, and benzothiazolyl. The term “heteroaryloxy” refers to —O-heteroaryl. The term “halogenated heteroaryl” refers to heteroaryl substituted with one, two, three, or more halogen atoms.

The term “heterocyclic” includes heterocycloalkyl and heteroaryl.

Alkyl, alkylene, haloalkylene, alkoxyl, cycloalkyl, heterocycloalkyl, heterocycloalkoxy, alkenyl, alkynyl, aryl, and heteroaryl mentioned herein include both substituted and unsubstituted moieties. Examples of a substituent include deuterium, halogen (e.g., F, Cl, and Br), amino, hydroxy, alkyl and haloalkyl (e.g., methyl, fluoromethyl, difluoromethyl, trifluoromethyl, difluoroethyl, and 1,1-difluoro-2-hydroxylethan-1-yl), alkenyl and haloalkenyl (e.g., ethylenyl and 3,3-difluoro-2-methylpropen-3-yl), cycloalkyl (e.g., cyclopropyl and cyclobutyl), cycloheteroalkyl (e.g., tetrahydrofuranyl), —CN, —CONR'R", —NR'R", —NR'COR", —NR'$SO_2$R", —NCOOR', —COR', —COOR', —SR', —SONR'R", and —OR', wherein R' and R' are on each occurrence independently selected from the group consisting of hydrogen, $C_{1-6}$ alkyl, $C_{24}$ alkenyl, and $C_{24}$ alkynyl optionally substituted with 1-3 halogens. All substituents can be further substituted.

The term “compound”, when referring to a compound of this invention, also includes its salts, solvates, hydrates, polymorph, co-crystals, tautomers, stereoisomers, or isotopically labeled derivatives thereof.

The pharmaceutically acceptable salts include those listed in Handbook of Pharmaceutical Salts: Properties, Selection and Use, $2^{nd}$ Revised Edition, P. H. Stahl and C. G. Wermuth (Eds.), Wiley-VCH, New York, (2011). In addition to pharmaceutically acceptable salts, other salts are contemplated in the invention. They may serve as intermediates in the purification of compounds or in the preparation of other pharmaceutically acceptable salts, or are useful for identification, characterization or purification of compounds of the invention. A solvate refers to a complex formed between an active compound and a pharmaceutically acceptable solvent. Examples of a pharmaceutically acceptable solvent include water, ethanol, isopropanol, acetonitrile, dimethylformamide, dimethyl sulfoxide, ethyl acetate, acetic acid, and ethanolamine. A prodrug refers to a compound that, after administration, is metabolized into a pharmaceutically active drug. Examples of a prodrug include esters and other pharmaceutically acceptable derivatives.

The compounds of the present invention may contain one or more non-aromatic double bonds or asymmetric centers. Each of them occurs as a racemate or a racemic mixture, a single R enantiomer, a single S enantiomer, an individual diastereomer, a diastereomeric mixture, a cis-isomer, or a trans-isomer. Compounds of such isomeric forms are within the scope of this invention. They can be present as a mixture or can be isolated using chiral synthesis or chiral separation technologies.

“An effective amount” refers to the amount of a compound that is required to confer the therapeutic effect. Effective doses will vary, as recognized by those skilled in the art, depending on the types of symptoms treated, route of administration, excipient usage, and the possibility of co-usage with other therapeutic treatment.

The term “subject” refers to an animal such as a mammal including a human. A human is a preferred subject.

The carrier in the pharmaceutical composition must be “acceptable” in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples include colloidal silicon oxide, magnesium stearate, cellulose, sodium lauryl sulfate, and D&C Yellow #10.

The details of one or more embodiments of the invention are set forth in the description below. Other features, objects, and advantages of the invention will be apparent from the description and from the claims.

DETAILED DESCRIPTION

The pnictogen-containing heterocyclic compounds of this invention contains at least one cationic quaternary pnictogen atom and a leaving group.

The compounds are particularly useful in modifying a substrate having a functional group such as hydroxyl (OH), thiol (SH), selenol (SeH), and tellurol (TeH). These functional group in the substrate can substitute the leaving group of the pnictogen-containing heterocyclic compound. It is unexpectedly found that reaction rate of the modification is surprisingly fast and that the reaction can be carried out in a mild condition such as in an aqueous medium at a mild pH range in the absence of a catalyst. The pnictogen-containing heterocyclic compounds of this invention each have a high water solubility. They can be used to modify a substrate in a medium with a high water content, which is not achievable with other existing reagents due to their low aqueous solubility or instability. Modification is readily carried out under mild conditions near pH 7 without the need to use a base, which is not practically possible with other existing reagents due to their slow reaction with chalcogens. As shown in examples below, the compounds of this invention allow incorporation of biomolecules with high structural complexity, which cannot be attained by other existing methods due to limited structural complexity of the employed reagents.

Suitable substrates include pharmaceutical active ingredients, amino acids, peptides, proteins, polymers, modified DNA, modified RNA, polymers, other macromolecules, and nanoparticle.

Referring to Formula (I):

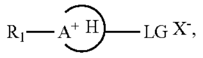

$R_1$ can be hydrogen, oxygen, alkyl, aryl, amino, alkylamino, arylamino, dialkylamino, diarylamino, borate (RR'R"$B^-$—), or silyl (—SiRR'R"), in which each of R, R', and R", independently, is hydrogen, alkyl, aryl, halogen, hydroxy, alkoxy, aryloxy, siloxy, amino, alkylamino, arylamino, dialkylamino, or diarylamino. LG is a leaving group, which is replaced by the incoming sulfur nucleophile during a modification reaction. It can be selected from group consisting of hydrogen, halogen, cyano, thiolate (RS—), sulfoxide (R(O)S—), sulfonyl ($R(O)_2S$—), sulfonate ($R(O)_2S$—O—), sulfonamide, diazo, azido, nitro, nitroso, hydroxy, alkoxy, alkenoxy, aryloxy, carboxyl (RCOO—), siloxy, phosphonate ((RO)(R'O)(O)P—), phosphate ((RO)(R'O)(O)P—O—), trialkyl ammonium, triaryl ammonium, trialkyl phosphonium, and triaryl phosphonium, in which R and R' are independently selected from the group consisting of hydrogen, alkyl, aryl, halogen, hydroxy, alkoxy, aryloxy, siloxy, amino, alkylamino, arylamino, dialkylamino, and diarylamino.

The heterocyclic compounds can be any of the compounds of the following formula:

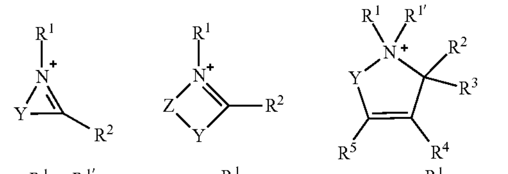
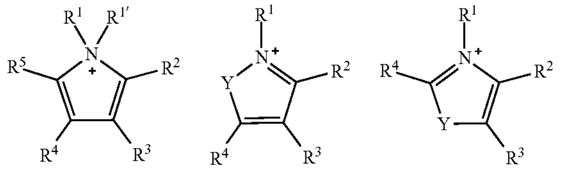
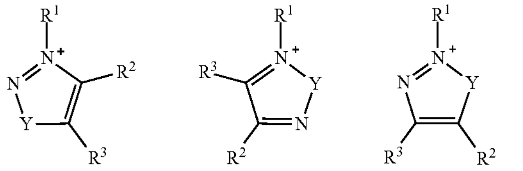
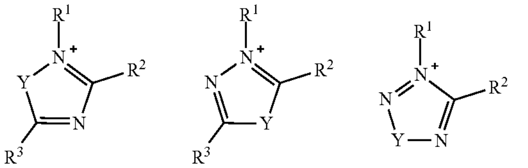
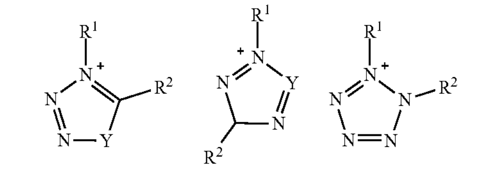

-continued

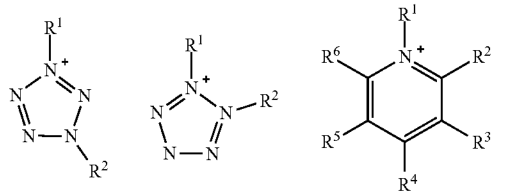
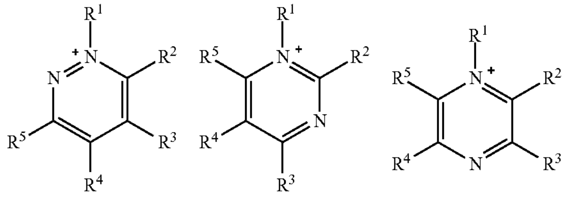
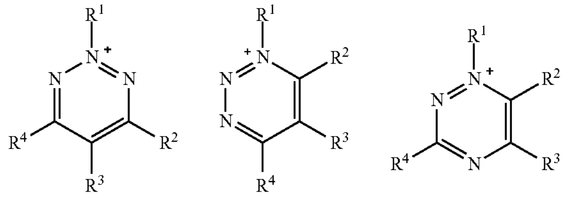
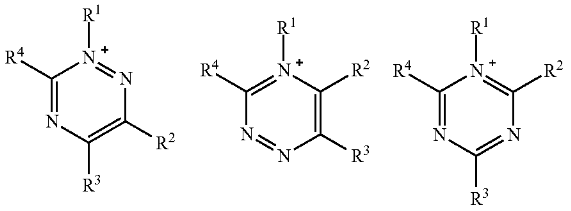
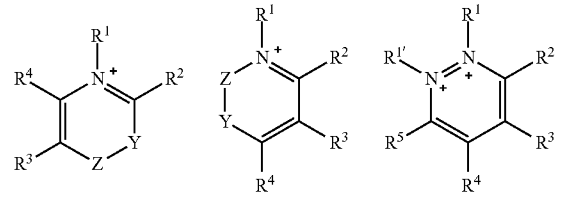
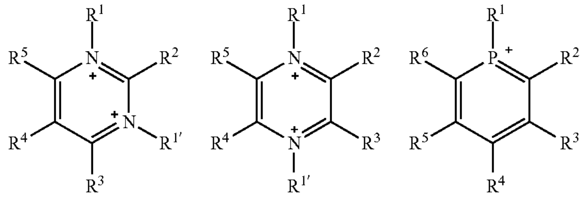
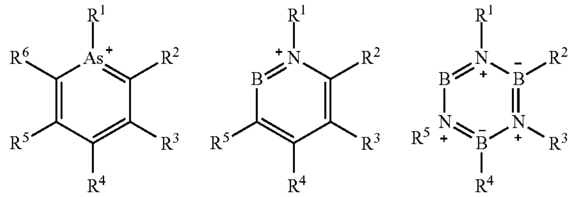
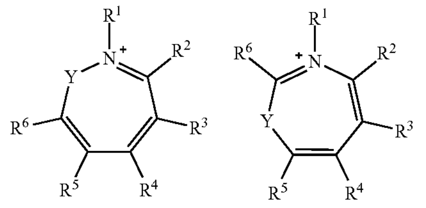

-continued
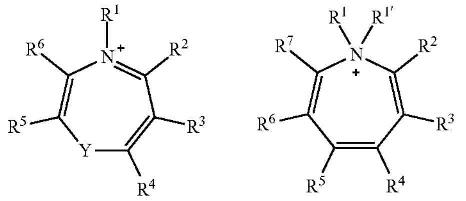
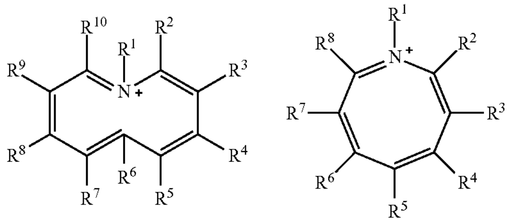
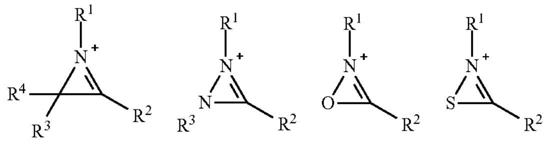
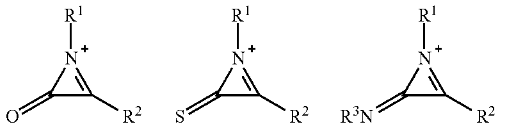
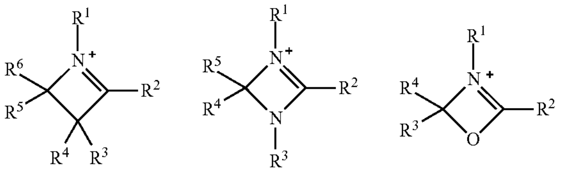
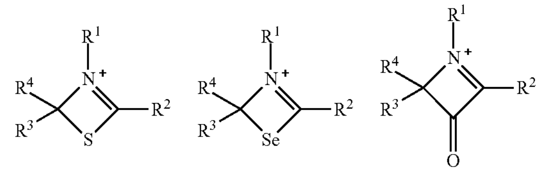
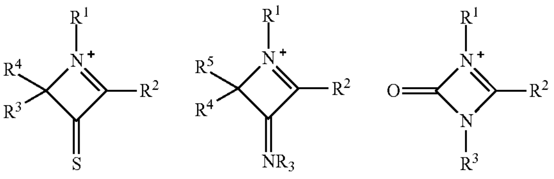
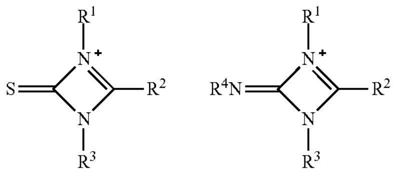
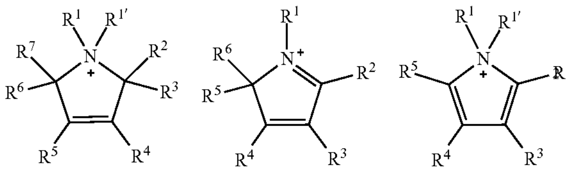
-continued
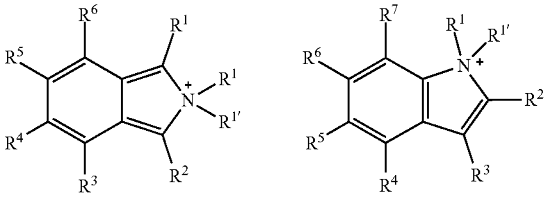
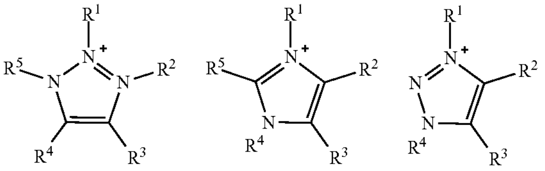
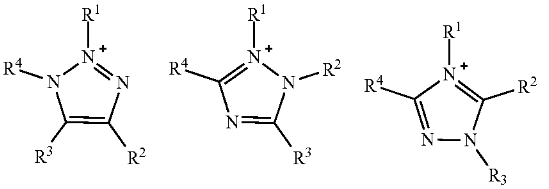
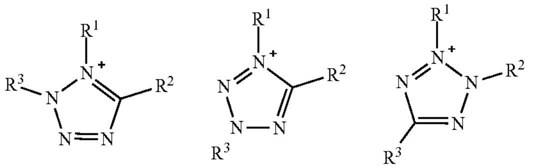
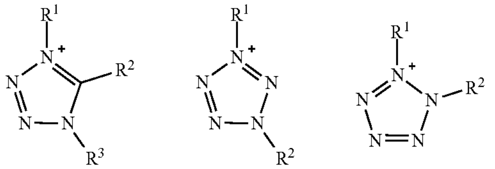
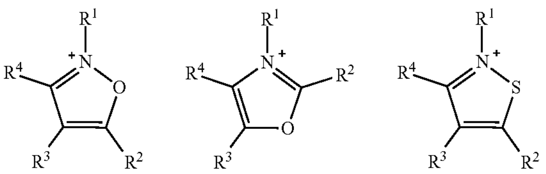
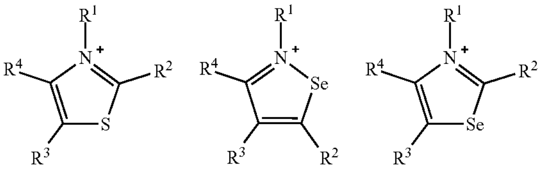
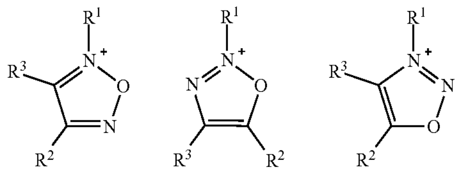
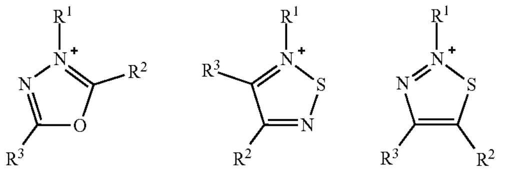

-continued
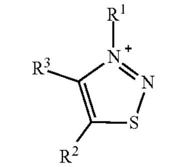
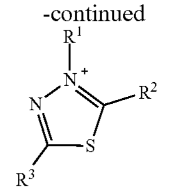
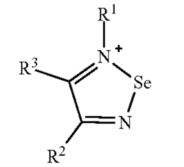
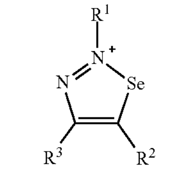
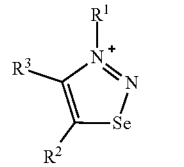
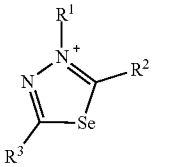
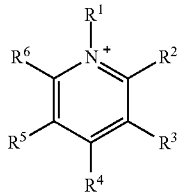
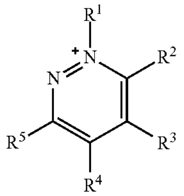
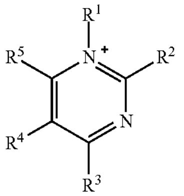
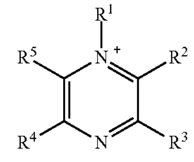
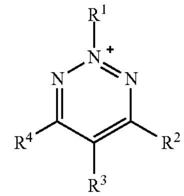
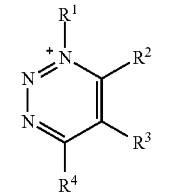
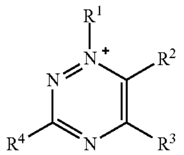
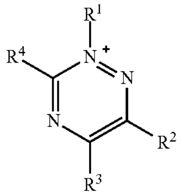
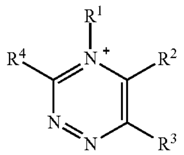
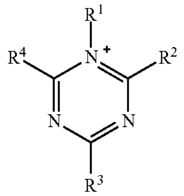
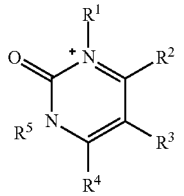
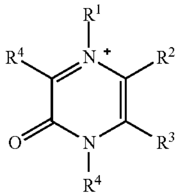
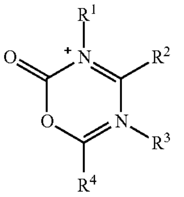
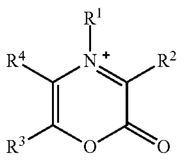
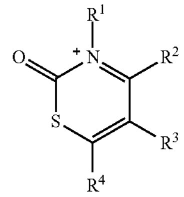
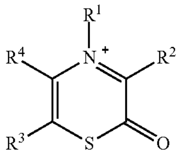
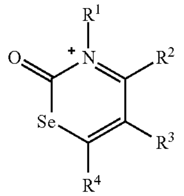
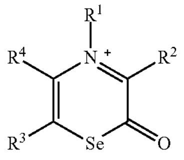
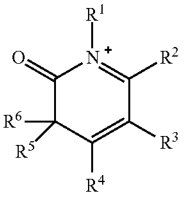
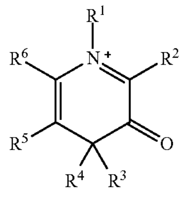
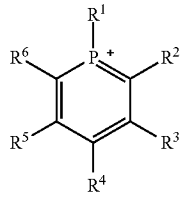
-continued
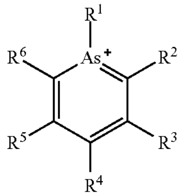
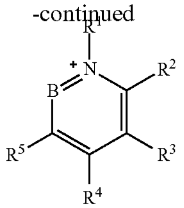
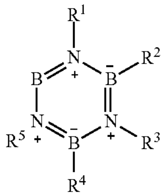
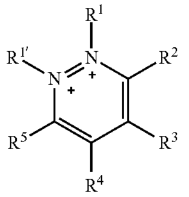
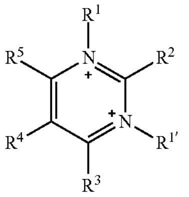
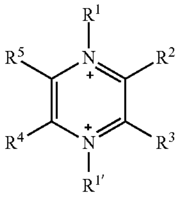
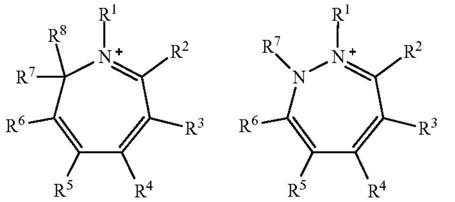
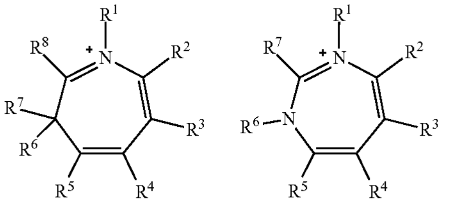
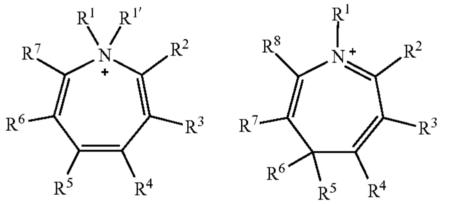
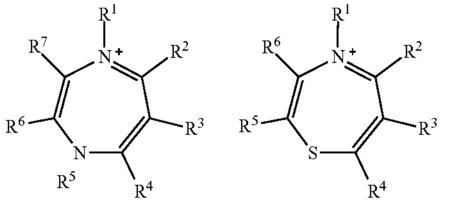
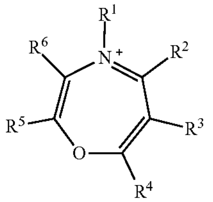
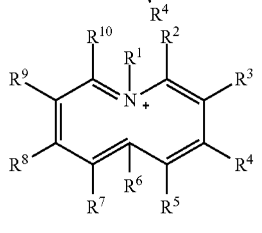
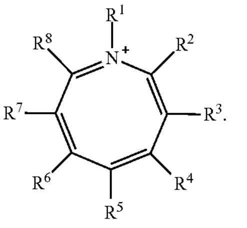
In the above formulas, $R^1$ and $R^{1'}$ are independently selected from the group consisting of hydrogen, oxygen, alkyl, aryl, amino, alkylamino, arylamino, dialkylamino, diarylamino, borate ($RR'R''B^-$—), and silyl (—SiRR'R''), in which R, R', and R'' are independently selected from the group consisting of hydrogen, alkyl, aryl, halogen, hydroxy, alkoxy, aryloxy, siloxy, amino, alkylamino, arylamino, dialkylamino, and diarylamino;

each of $R^2$, $R^3$, $R^4$, $R^5$, $R^6$, $R^7$, $R^8$, $R^9$, and $R^{10}$ is independently selected from the group consisting of hydrogen, alkyl, alkenyl, alkynyl, aryl, carbonyl, imine, iminium, cyano, halogen, sulfoxide, sulfonyl ($R(O)_2S$—), sulfonate ($R(O)_2S$—O—), sulfonamide, diazo, azido, nitro, nitroso, hydroxy, alkoxy, alkenoxy, aryloxy, carboxyl (RCOO—), siloxy, phosphonate ((RO)(R'O)(O)P—), phosphate ((RO)(R'O)(O)P—O—), amino, alkylamino, arylamino, dialkylamino, diarylamino, trialkyl ammonium, triaryl ammonium, trialkyl phosphonium, and triaryl phosphonium; and at least one of the $R^2$, $R^3$, $R^4$, $R^5$, $R^6$, $R^7$, $R^8$, $R^9$, and $R^{10}$ groups is a leaving group, which is replaced by the incoming sulfur nucleophile, selected from group consisting of hydrogen, halogen, cyano, thiolate (RS—), sulfoxide (R(O)S—), sulfonyl ($R(O)_2S$—), sulfonate ($R(O)_2S$—O—), sulfonamide, diazo, azido, nitro, nitroso, hydroxy, alkoxy, alkenoxy, aryloxy, carboxyl (RCOO—), siloxy, phosphonate ((RO)(R'O)(O)P—), phosphate ((RO)(R'O)(O)P—O—), trialkyl ammonium, triaryl ammonium, trialkyl phosphonium, and triaryl phosphonium; and Y and Z are independently selected from the group consisting of oxygen, sulfur, selenium, amino group (—NR—), —CR(R')—, carbonyl, thiocarbonyl, imine, alkylimine, and arylimine, in which R and R' are independently selected from the group consisting of hydrogen, alkyl, aryl, halogen, hydroxy, alkoxy, alkenoxy, aryloxy, siloxy, nitro, nitroso, amino, alkylamino, arylamino, dialkylamino, diarylamino, and cyano.

In certain instances, any combination of two of $R^1$, $R^{1'}$, $R^2$, $R^3$, $R^4$, $R_5$, $R^6$, $R^7$, $R^8$, $R^9$, and $R^{10}$ can be joined together to form a cyclic structure.

In other instances, any combination of three of $R^1$, $R^{1'}$, $R^2$, $R^3$, $R^4$, $R_5$, $R^6$, $R^7$, $R^8$, $R^9$, and $R^{10}$ can be joined together to form a bicyclic structure.

Any compound described above, if not charge-neutral, should also contain one or more counter anions to form a charge-neutral entity. The number of net negative charges of the anion(s) matches that of the net positive charges of the pnictogen-containing heterocycle described above.

The compounds described above are useful in modifying a substrate containing a chalcogen functional groups such as OH, SH, SeH, and TeH. The modification reaction can be depicted in Schemes I-V below.

Scheme I

One-step functionalization of chalcogen-containing substrates using single reaction site CAP reagents

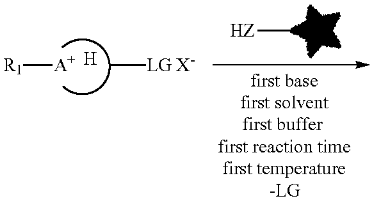

-continued

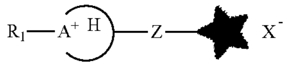

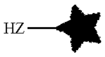 = chalcogen-containing substrate

Z = O, S, or Se

Referring to Scheme I above, $R_1$, $A^+$,

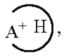,

LG, and $X^-$ are defined for Formula (I) above. The reaction is performed for a first reaction time (e.g., 1 minute to 48 hours, preferably 2 minutes to 12 hours, and more preferably 5 minutes to 6 hours) at a first temperature (e.g., −80° C. to 150° C., −20° C. to 100° C., and 10° C. to 40° C.), optionally in the presence of a first base, a first solvent, a first buffer, or any combination thereof.

The first base, if needed for the chemical transformation, can be ammonium hydroxide, alkylamines, dialkylamines, trialkylamines, pyridine derivatives, imidazole derivatives, guanidine derivatives, 1,8-bis(dimethylamino)naphthalene, phosphazenes, tetraalkylammonium hydroxides, trialkylaryllammonium hydroxides, tetraalkylphosphonium hydroxides, tetraarylphosphonium hydroxides, alkali metal hydroxides, alkali metal alkoxides, alkali metal carbonates, alkali metal bicarbonates, alkali metal phosphates, alkaline earth metal hydroxides, alkaline earth metal alkoxides, alkaline earth metal carbonates, alkaline earth metal bicarbonates, alkaline earth metal phosphates, alkyllithium reagents, aryllithium reagents, alkali metal amides, alkali metal dialkylamides, alkali metal hexamethyldisilazides, or an acceptable salt, solvate, hydrate, polymorph, co-crystal, tautomer, or a mixture thereof;

Examples of the first solvent, if needed, include water, dimethylformamide (DMF), N-methylformamide, $CH_3CN$, t-butanol, $(CH_3)_2CHOH$, $CH_3CH_2OH$, $CH_3OH$, $CF_3CH_2OH$, DMSO, diethyl ether, dibutyl ether, methyl t-butyl ether, tetrahydrofuran (THF), 1,4-dioxane, dimethoxyethane, diglyme, ethylene glycol, glycerol, carbon tetrachloride, chloroform, dichloromethane, dichloroethane, acetone, 2-butanone, toluene, xylenes, fluorobenzene, chlorobenzene, α,α,α-trifluorotoluene, hexafluorobenzene, tris(2-carboxyethyl)phosphine (TCEP), and a mixture thereof.

The first buffer, if needed, typically contains $Na_3PO_4$, piperazine-N,N'-bis(2-ethanesulfonic acid) (PIPES)(Fisher Scientific® Company, Pittsburgh, PA), 3-(N-morpholino) propanesulfonic acid (MOPS), 4-(2-hydroxyethyl)-1-piperazineethanesulfonic acid (HEPES), 2-(N-morpholino)ethanesulfonic acid (MES), tris(hydroxymethyl)aminomethane (TRIS), tris(2-carboxyethyl)phosphine (TCEP), or a mixture thereof.

A subset of the above-described compounds each contain two, three, or more leaving groups. They can react with two functional groups as shown in Schemes II, III, and IV below.

Scheme II

Two-step functionalization of chalcogen-containing substrates using dual reactive site CAP

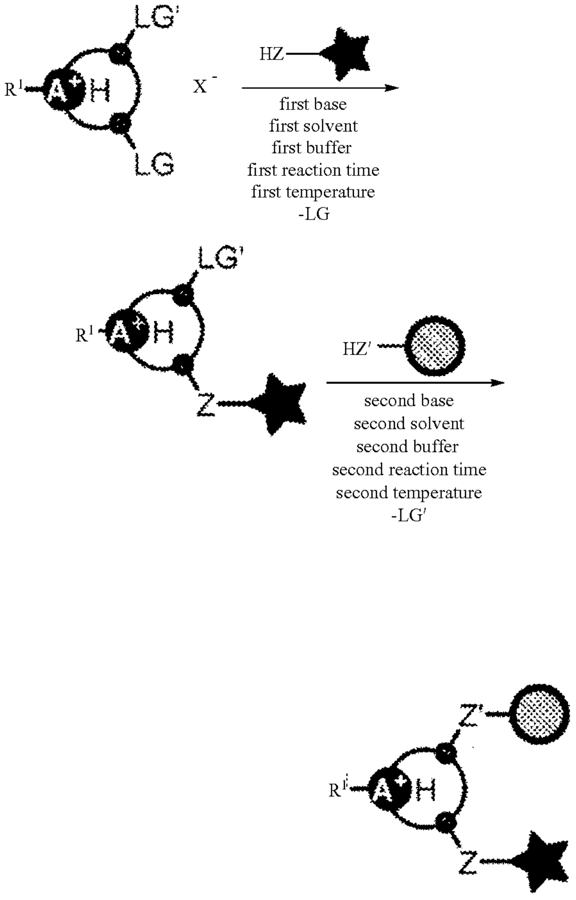

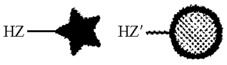 = chalcogen-containing labeling target molecule or matter

Each of LG and LG' is a leaving group
Z and Z' = O, S, or Se

Scheme III

Stapling a substrate containing two chalcogens using ditopic CAP reagents

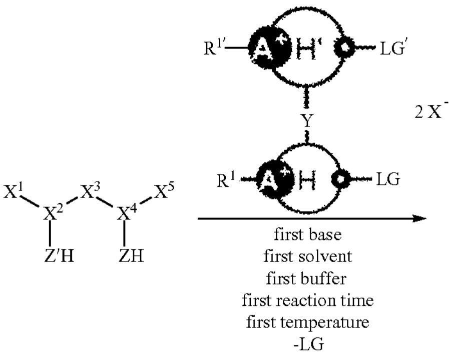

-continued

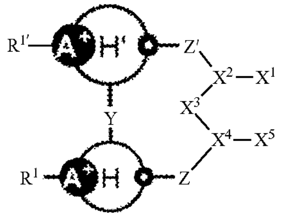

Scheme IV

Stapling a substrate containing two chalcogens using ditopic monocyclic CAP reagents

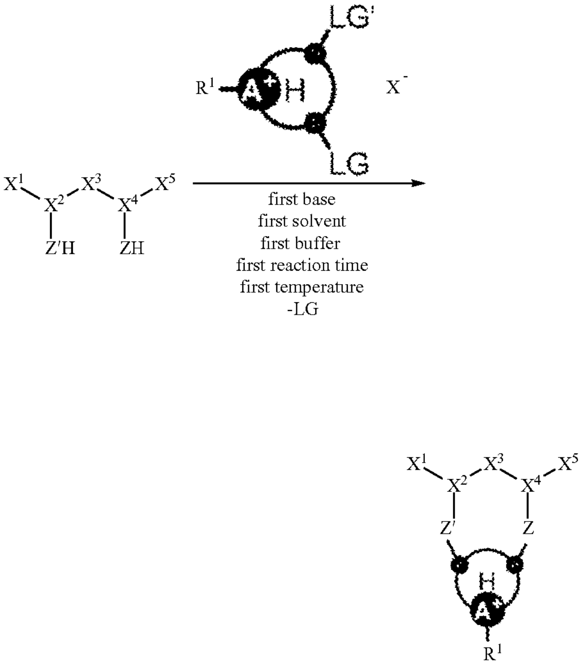

In Schemes II, III, and IV above, each of the pnictogen-containing heterocyclic compound is used to conjugate two functional groups, either in a single substrate or two separate substrates. Each substrate contains hydroxyl, thiol, or selenol, which is then covalently bond to the pnictogen-containing heterocyclic compound.

In the schemes above, LG and LG' each are leaving groups as described above; $X^-$ is a counter anion; H-Z-★ is a chalcogen-containing substrate, in which Z is oxygen, sulfur, or selenium; H-Z'-o is a chalcogen-containing substrate, wherein Z' is oxygen, sulfur, or selenium; $X^1$, $X^2$, $X^3$, $X^4$, and $X^5$ are each independently selected from the group consisting of a natural amino acid, an unnatural amino acid, a peptide, an oligopeptide, a polypeptide, a protein, hydrogen, an alkyl group, an alkenyl group, an alkynyl group, an aryl group, an heteroaryl group, —CR(R')—, carbonyl, ether, thioether, sulfoxide, sulfone, phosphate, imine, alkylimine, and arylimine; wherein R and R' are independently selected from the group consisting of hydrogen, alkyl, aryl, halogen, hydroxy, alkoxy, aryloxy, siloxy, amino, alkylamino, arylamino, dialkylamino, and diarylamino; and Y is a linker and selected from the group consisting of a natural amino acid, an unnatural amino acid, a peptide, an oligopeptide, a polypeptide, a protein, $(CH_2)_n$, an alkyl group, an alkyl group, an alkenyl group, an alkynyl group, an aryl group, an heteroaryl group, —CR(R')—, carbonyl, ether, thioether, sulfoxide, sulfone, phosphate, imine, alkylimine, and arylimine; wherein R and R' are independently selected from the group consisting of hydrogen, alkyl, aryl, halogen, hydroxy, alkoxy, aryloxy, siloxy, amino, alkylamino, arylamino, dialkylamino, and diarylamino, n being 0 to 50.

In Scheme II above, the CAP compound is reacted with a first substrate, followed by a reaction with a second substrate. This two-step reaction sequence leads to a covalent conjugate of two chalcogen-containing substrates.

The first base, the first solvent, the first buffer, the first temperature, and the first reaction time are as defined above.

The second reaction is carried out at a second temperature for a second reaction time, optionally in the presence of a second base, a second solvent, a second buffer, or any combinations thereof. The second base, the second solvent, the second buffer, the second temperature, and the second reaction time can be selected from the groups shown above for their counterparts in the first reaction.

In Schemes III and IV above, the substrate can a biomolecule, including peptides, proteins, modified DNA, modified RNA, synthetic polymers, and nanoparticles. The number of atoms between the ZH and Z'H ranges from 1 to 50000.

In certain embodiments, the pnictogen-containing heterocyclic compound of this invention is used to functionalize a substrate having two or more hydroxyl, thiol, and selenol groups in a sequence-dependent regioselective manner as shown in Scheme V below.

Scheme V

Sequence-dependent regioselective functionalization of chalcogens with CAP reagents

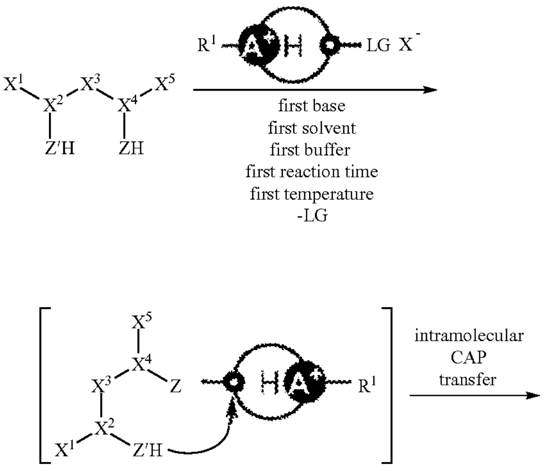

intermediate, kinetic product

-continued

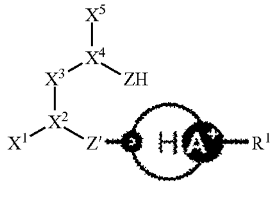

thermodynamic product

Each variable in Scheme V is as defined above. In the first step, the CAP compound reacts with the most nucleophilic hydroxyl, thiol, or selenol group (i.e., ZH). The resultant kinetic product is an intermediate, which undergoes intramolecular CAP transfer to the adjacent chalcogen (i.e., Z'H) to form a product with a higher thermodynamic stability. The sequence-dependent regioselective functionalization relies on (1) the faster reaction of the chalcogen with higher reactivity toward the CAP compound and (2) the intramolecular transfer of the CAP moiety to a spatially close nucleophilic chalcogen.

The substrate can be a biomolecule, including peptides, proteins, modified DNA, modified RNA, synthetic polymers, and nanoparticles. The number of atoms between the ZH and Z'H ranges from 1 to 50000.

Following the reaction schemes shown above, the CAP compounds of this invention are suitable to modifying substrates such as biomolecules, particularly proteins and peptides. The modified biomolecules are useful in broad applications, including the production of protein-drug conjugates for targeting specific tissues, the synthesis of stapled peptides for improved metabolic stability and cell permeability, mass spectrometry-based protein profiling studies, the incorporation of functional tags, such as fluorescent labels, into biomacromolecules for detection and imaging studies, and the development of covalent drugs by formation protein-small molecule complexes. In addition, these reactions are used in biological studies, in which protein or peptide functionality needs to be reversibly or irreversibly modified by introduction or masking of particular functional groups.

Some applications include antibody-CAP-drug conjugate and protein-CAP-drug conjugate, in which a CAP compound having two leaving groups is utilized. The antibody or protein covalently bonds the CAP compound through the substitution of the first leaving group in the CAP compound with the thiol functional group in the antibody or protein. A drug molecule is also covalently attached to the CAP compound through the substitution of the second leaving group in the CAP compound with the hydroxyl, thiol, or selenol functional group in the drug molecule.

Exemplary therapeutic protein-CAP-drug and antibody-CAP-drug conjugates are illustrated in Scheme VI below.

Scheme VI

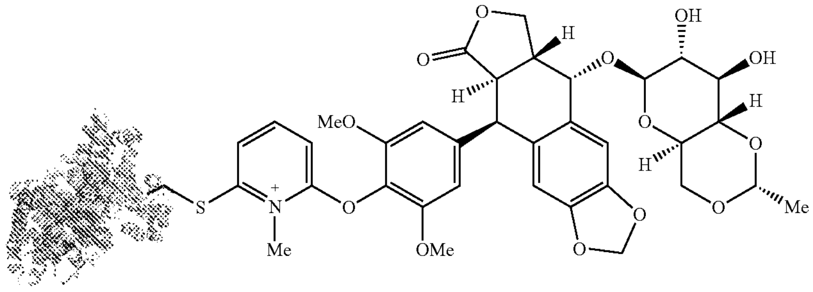

protein-CAP-etoposide conjugate

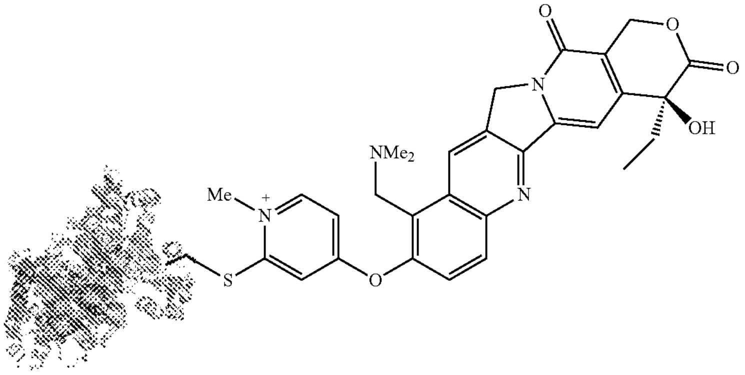

protein-CAP-topotecan conjugate

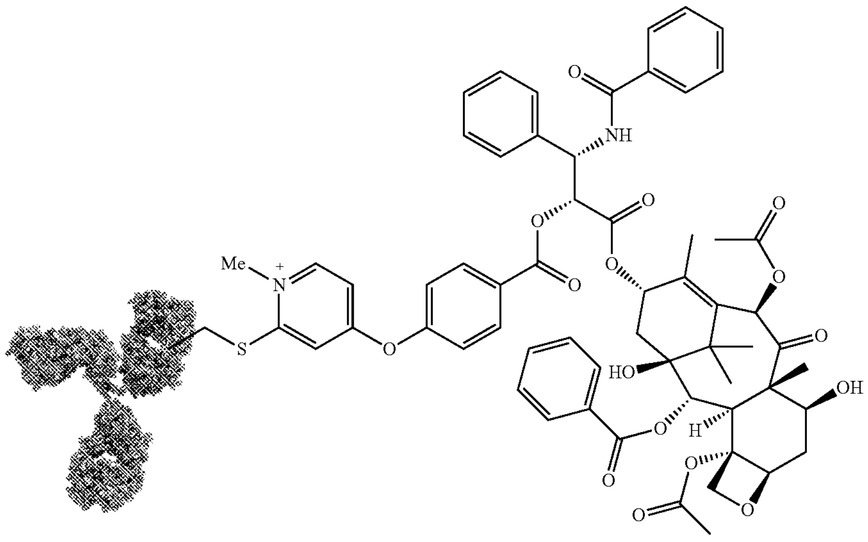

antibody-CAP-paclitaxel conjugate

In Scheme VI above, etoposide, topotecan, and paclitaxel are all anti-cancer agents. A CAP compound is a pnictogen-containing heterocyclic compound of this invention. All proteins and antibodies can be modified by a CAP compound. Specific suitable proteins and antibodies are those containing a thiol functional group.

The compounds and conjugates described above can be prepared by synthetic methods well known in the art. See, e.g., R. Larock, Comprehensive Organic Transformations ($3^{rd}$ Ed., John Wiley and Sons 2018); P. G. M. Wuts and T. W. Greene, Greene's Protective Groups in Organic Synthesis ($4^{th}$ Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis ($2^{nd}$ ed., John Wiley and Sons 2009) and subsequent editions thereof.

The compounds thus prepared can be purified following conventional methods such as crystallization, distillation/vacuum distillation, flash chromatography over silica, and preparative liquid chromatography.

Without further elaboration, it is believed that one skilled in the art can, based on the above description, utilize the present invention to its fullest extent. The following examples are to be construed as merely illustrative and not limitative of the disclosure in any way whatsoever.

All publications cited herein are hereby incorporated by reference in their entirety.

Set forth below are examples illustrating preparation and evaluation of compounds of this invention.

The abbreviations as used herein are provided in Table 2 below with their definitions, which are used conventionally in the art.

TABLE 2

| Abbr. | Name | Abbr. | Name |
|---|---|---|---|
| BAPNA | Nα-benzoyl-DL-arginine 4-nitroanilide hydrochloride | BSA | bovine serum albumin |
| CHCA | α-cyano-4-hydroxycinnamic acid | Cys | cysteine |
| DMF | dimethylformamide | DMSO | Dimethyl sulfoxide |
| EDTA | ethylenediaminetetraacetic acid | ESI-HRMS | High resolution electrospray ionization mass spectrometry |
| Et | ethyl | $Et_2O$ | ethyl ether |
| GFP | Green Fluorescent Protein | HATU | 1-[bis(dimethylamino)-methylene]-1H-1,2,3-tri-azolo[4,5-b] pyridinium 3-oxide hexafluorophosphate |
| HPLC | High-Performance Liquid Chromatography | MALDI-MS | matrix-assisted laser desorption/ionization mass spectrometry |
| LCMS | Liquid Chromatography-Mass Spectrometry | HD | high resolution |
| Me | methyl | MeCN | acetonitrile |
| MS | mass spectrometry | NMR | nuclear magnetic resonance |
| Ph | phenyl | PIPES | piperazine-N,N'-bis(2-ethanesulfonic acid) |
| TAMRA | carboxytetramethyl-rhodamine | TCEP | tris(2-carboxyethyl)phosphine |
| THF | tetrahydrofuran | TLC | thin layer chromatography |

EXAMPLES

Reagents were purchased from commercial sources and used as received unless otherwise indicated. Anhydrous solvents were purchased from commercial sources and stored in a dry box. Reaction mixtures were monitored by thin-layer chromatography (TLC) on pre-coated, aluminum-backed silica gel 60 F254 plates. Column chromatography was performed on silica gel 60 (230-400 mesh). NMR spectra were recorded on a Bruker® Avance III HD NMR spectrometer. $^1H$ and $^{13}C$ chemical shifts are reported in ppm relative to $SiMe_4$ (δ=0.00 ppm). $^1H$ and $^{13}C$ NMR spectra were referenced internally to residual solvent peaks. $^{19}F$ spectra were referenced externally to $CFCl_3$ (0.0 ppm). Low-resolution electrospray mass spectra were acquired on a Shimadzu® LCMS-2020 spectrometer. High-resolution mass spectra were acquired on AB SCIEX® TripleTOF 4600 system at the RI-INBRE Centralized Research Core Facility. Compounds were purified using Agilent® 1200 Series HPLC systems fitted with multi-wavelength detectors and automated fraction collectors using a C18 reverse stationary phase (Zorbax®-SB C18 columns: preparative, 7 μm, 21.2×250 mm; semi-preparative, 5 μm 9.4×250 mm; and analytical, 5 μm, 4.6×250 mm; all commercially available from Agilent, Santa Clara, CA) and a mobile phase composed of two solvents (A: $H_2O$+0.1% (v/v) $CF_3CO_2H$; B: $CH_3CN$+0.1% (v/v) $CF_3CO_2H$) with a solvent gradient selected from those shown in Table 3 below. UV-visible spectra were recorded on a Varian® Cary 60 Bio UV-visible spectrophotometer. Quartz cuvettes with 1 cm path lengths were used for all spectroscopic measurements. Milli-Q® purified water with resistivity of at least 18 MΩ·$cm^{-1}$ was used to prepare all buffers. Aqueous PIPES buffers consisted of 50 mM PIPES, 100 mM KCl. Unless otherwise indicated, the pH of the buffers was adjusted to 7.

TABLE 3

HPLC Solvent Gradients

| Gradient | Time (min) | % Solvent B | Gradient | Time (min) | % Solvent B |
|---|---|---|---|---|---|
| 1[a] | 0 | 10 | 2[b] | 0 | 0 |
| | 3 | 35 | | 2 | 0 |
| | 15 | 38 | | 6 | 3 |
| | 17 | 100 | | 12 | 9 |
| | 19 | 10 | | 14 | 100 |
| | 20 | 10 | | 16 | 0 |
| | | | | 18 | 0 |
| 3[b] | 0 | 10 | 4[b] | 0 | 10 |
| | 3 | 20 | | 3 | 20 |
| | 11 | 28 | | 9 | 26 |
| | 13 | 100 | | 11 | 100 |
| | 15 | 10 | | 13 | 10 |
| | 16 | 10 | | 14 | 10 |
| 5[b] | 0 | 10 | 6[b] | 0 | 10 |
| | 3 | 25 | | 3 | 15 |
| | 13 | 35 | | 13 | 25 |
| | 15 | 100 | | 15 | 100 |
| | 17 | 10 | | 17 | 10 |
| | 18 | 10 | | 18 | 10 |
| 7[b] | 0 | 10 | 8[c] | 0 | 0 |
| | 5 | 10 | | 20 | 20 |
| | 9 | 25 | | 25 | 22.5 |

TABLE 3-continued

| HPLC Solvent Gradients | | | | | |
|---|---|---|---|---|---|
| Gradient | Time (min) | % Solvent B | Gradient | Time (min) | % Solvent B |
| | 14 | 100 | | 28 | 100 |
| | 16 | 10 | | 30 | 100 |
| | 19 | 10 | | 32 | 0 |
| | | | | 35 | 0 |
| $9^c$ | 0 | 0 | $10^c$ | 0 | 0 |
| | 10 | 15 | | 20 | 20 |
| | 30 | 75 | | 40 | 30 |
| | 32 | 100 | | 45 | 40 |
| | 33 | 100 | | 50 | 100 |
| | 35 | 0 | | 52 | 100 |
| | 36 | 0 | | 54 | 0 |
| | | | | 56 | 0 |
| $11^d$ | 0 | 10 | $12^c$ | 0 | 10 |
| | 5 | 10 | | 5 | 10 |
| | 30 | 100 | | 23 | 74 |
| | 33 | 100 | | 26 | 100 |
| | 36 | 10 | | 27 | 100 |
| | 40 | 10 | | 30 | 10 |
| | | | | 31 | 10 |
| $13^c$ | 0 | 0 | $14^b$ | 0 | 0 |
| | 3 | 0 | | 5 | 0 |
| | 6 | 24 | | 15 | 20 |
| | 13 | 28 | | 17 | 100 |
| | 16 | 100 | | 18 | 100 |
| | 17 | 100 | | 20 | 0 |
| | 20 | 0 | | 22 | 0 |
| | 21 | 0 | | | |
| $15^b$ | 0 | 10 | $16^b$ | 0 | 10 |
| | 5 | 28 | | 5 | 28 |
| | 19 | 69 | | 19 | 31 |
| | 21 | 100 | | 21 | 100 |
| | 22 | 100 | | 22 | 100 |
| | 25 | 10 | | 25 | 10 |
| | 30 | 10 | | 30 | 10 |
| $17^b$ | 0 | 0 | | | |
| | 5 | 5 | | | |
| | 30 | 30 | | | |
| | 33 | 33 | | | |
| | 36 | 36 | | | |
| | 40 | 40 | | | |

[a]Flow rate was 15 mL/min.
[b]Flow rate was 3 mL/min.
[c]Flow rate was 4 mL/min.
[d]Flow rate was 1 mL/min.

1-Iodo-9-(2-fluoro-4-pyridyl)-3,6,9-trioxanonane

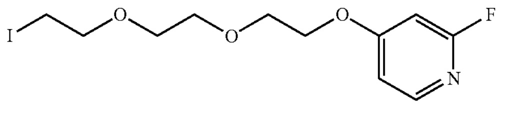 [SMILES: Fc1cc(OCCOCCOCCI)ccn1]

In a 20 mL scintillation vial, triglycol diiodide (2.22 g, 1.09 mL, 6 mmol), 2-fluoro-4-hydroxypyridine (339 mg, 3 mmol), and $K_2CO_3$ (415 mg, 3 mmol) were mixed in DMF (9 mL). The reaction was heated at 60° C. for 3 h, during which time the solid $K_2CO_3$ dissolved. The yellow reaction mixture was cooled to rt. DMF was removed by air flow. The crude product was purified by silica gel column chromatography (ethyl acetate:hexanes=1:2 to 1:1). A slightly yellow liquid was obtained (742 mg, 70% yield).

$^1$H NMR (400 MHz, $CDCl_3$) δ 8.00 (d, J=5.9 Hz, 1H), 6.73 (ddd, J=5.9, 2.1, 1.2 Hz, 1H), 6.40 (d, J=2.1 Hz, 1H), 4.21-4.16 (m, 2H), 3.91-3.86 (m, 2H), 3.74 (t, J=6.8 Hz, 2H), 3.73-3.69 (m, 2H), 3.69-3.65 (m, 2H), 3.25 (t, J=6.8 Hz, 2H). $^{19}$F NMR (377 MHz, $CDCl_3$) δ −66.70. $^{13}C^1\{H\}$ NMR (101 MHz, $CDCl_3$) δ 168.80 (d, J=11.7 Hz), 165.34 (d, J=235.2 Hz), 148.15 (d, J=18.6 Hz), 109.57 (d, J=4.2 Hz), 94.83 (d, J=41.8 Hz), 72.08, 71.00, 70.35, 69.37, 68.11, 2.98. MS (ESI+): m/z calculated for $[M+H]^+$ 356.0, found 356.1. MS (ESI+): m/z calculated for $[M+H]^+$ 356.0, found 356.1. ESI-HRMS(+) m/z calculated for $C_{11}H_{16}FINO_3^+$ $[M+H]^+$ 356.0154, found 356.0141.

1-Azido-9-(2-fluoro-4-pyridyl)-3,6,9-trioxanonane

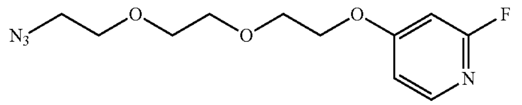 [SMILES: [N-]=[N+]=NCCOCCOCCOc1ccnc(F)c1]

In a 10 mL Schlenk flask, tetra-n-butylammonium azide (63 mg, 0.22 mmol) was added to a solution of 2-fluoro-4-(2-(2-(2-iodoethoxy)ethoxy)ethoxy)pyridine (71 mg, 0.2 mmol) in anhydrous THF (1 mL). The reaction was stirred at rt for 12 h. The solvent was removed under vacuum. The crude product was purified by silica gel column chromatography (ethyl acetate:hexanes=1:1 to 2:1). A colorless liquid was obtained (53 mg, 98% yield).

$^1$H NMR (400 MHz, $CDCl_3$) δ 8.01 (d, J=5.9 Hz, 1H), 6.73 (ddd, J=5.9, 2.1, 1.1 Hz, 1H), 6.41 (d, J=2.1 Hz, 1H), 4.21-4.17 (m, 2H), 3.92-3.86 (m, 2H), 3.74-3.71 (m, 2H), 3.69-3.65 (m, 4H), 3.38 (t, J=5.0 Hz, 2H). $^{13}C^1\{H\}$ NMR (101 MHz, $CDCl_3$) δ 168.84 (d, J=11.7 Hz), 165.37 (d, J=235.2 Hz), 148.16 (d, J=18.5 Hz), 109.57 (d, J=3.9 Hz), 94.84 (d, J=41.8 Hz), 71.07 (s), 70.86 (s), 70.28 (s), 69.39 (s), 68.11 (s), 50.78 (s). $^{19}$F NMR (471 MHz, $CDCl_3$) δ −66.7 (s). MS (ESI+): m/z calculated for $[M+H]^+$ 271.1, found 271.2. ESI-HRMS(+) m/z calculated for $C_{11}H_{16}FN_4O_3^+$ $[M+H]^+$ 271.1201, found 271.1189.

1-(2-Fluoro-4-pyridyl)-10-propargyl-1,4,7,10-tetraoxadecane

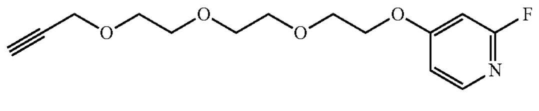 [SMILES: C#CCOCCOCCOCCOc1ccnc(F)c1]

In a 50 mL pressure tube, 3-(2-(2-(2-iodoethoxy)ethoxy)ethoxy)prop-1-yne (149 mg, 0.5 mMol), 2-fluoro-4-hydroxypyridine (62 mg, 0.55 mmol), and $K_2CO_3$ (84 mg, 0.61 mmol) were mixed in anhydrous acetone (5 mL). The reaction was heated in an oil bath (80° C.) for 24 h. The solvent was removed under vacuum. The crude product was purified by silica gel column chromatography (ethyl acetate: hexanes=1:1 to 2:1). A colorless liquid was obtained (113 mg, 80% yield).

$^1$H NMR (400 MHz, $CDCl_3$) δ 8.01 (d, J=5.9 Hz, 1H), 6.73 (ddd, J=5.9, 2.0, 1.1 Hz, 1H), 6.41 (d, J=2.1 Hz, 1H), 4.21-4.14 (m, 4H), 3.90-3.85 (m, 2H), 3.75-3.64 (m, 8H), 2.42 (t, J=2.4 Hz, 1H). $^{13}C^1\{H\}$ NMR (101 MHz, $CDCl_3$) δ 168.86 (d, J=11.6 Hz), 165.37 (d, J=235.1 Hz), 148.15 (d, J=18.6 Hz), 109.60 (d, J=3.9 Hz), 94.85 (d, J=41.8 Hz), 79.72, 74.69, 71.05, 70.79, 70.62, 69.31, 69.22, 68.14, 58.55. $^{19}$F NMR (377 MHz, $CDCl_3$) δ −66.8 (s). MS (ESI+): m/z calculated for $[M+H]^+$ 284.1, found 284.2. MS (ESI+):

m/z calculated for $[M+H]^+$ 284.1, found 284.2. ESI-HRMS (+) m/z calculated for $C_{14}H_{19}FNO_4^+$ $[M+H]^+$ 284.1293, found 284.1303.

N$^1$-Methyl-N$^2$-Methyl-N$^2$-4-hydroxybenzoyl-1,2-ethylenediamine

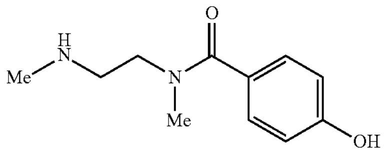 [SMILES: CNCCN(C)C(=O)c1ccc(O)cc1]

A mixture of 4-acetoxybenzoic acid (77 mg, 0.427 mmol) and thionyl chloride (286 μL, 3.84 mmol) was heated at 85° C. in a OH, pressure tube for 1 h. The mixture was cooled to room temperature. Excess thionyl chloride was removed under vacuum to afford crude 4-(chlorocarbonyl)phenyl acetate as a colorless oil. The crude 4-(chlorocarbonyl) phenyl acetate was dissolved in anhydrous $CH_2Cl_2$ (2 mL). To this mixture, t-butyl methyl(2-ethyl)carbamate (755 μL, 3.84 mmol) was added. The reaction was stirred at room temperature for 12 h before the addition of water (20 mL). The mixture was then extracted with $CH_2Cl_2$ (15 mL×3). The combined organic phase was dried over $Na_2SO_4$. The solvent was removed under vacuum. The crude product was passed through a pad of silica gel with ethyl acetate as the eluent to afford t-butyl (2-(4-hydroxy-N-methylbenzamido) ethyl)(methyl)-carbamate as a viscous colorless oil (121 mg, 85% yield). A portion of oil (100 mg, 0.32 mmol) was mixed with $CH_2Cl_2$ (2.5 mL) and trifluoroacetic acid (2.5 mL). After 30 min, the solvent and trifluoroacetic acid were removed under vacuum. A slightly yellow solid was obtained (76.2 mg as a trifluoroacetic acid salt) and used in the next step without further purification.

$^1$H NMR (400 MHz, MeOD) δ 7.41 (d, J=8.5 Hz, 2H), 6.88-6.82 (m, 2H), 3.80 (t, J=5.7 Hz, 2H), 3.28 (t, J=5.7 Hz, 2H, partially overlapping with $CD_2HOD$), 3.10 (s, 3H), 2.76 (s, 3H). $^{13}C^{1}\{H\}$ NMR (101 MHz, MeOD) δ 175.36, 160.99, 130.75, 126.82, 116.07, 48.46 (partially overlapping with $CD_3OD$), 46.15 (br), 38.58 (br), 34.04. MS (ESI+): m/z calculated for $M^+$ 209.1, found 209.3.

N$^1$-Methyl-N-5-carbonyltetramethylrhodamine-N$^2$-methyl-N$^2$-4-hydroxybenzoyl-1,2-ethylenediamine

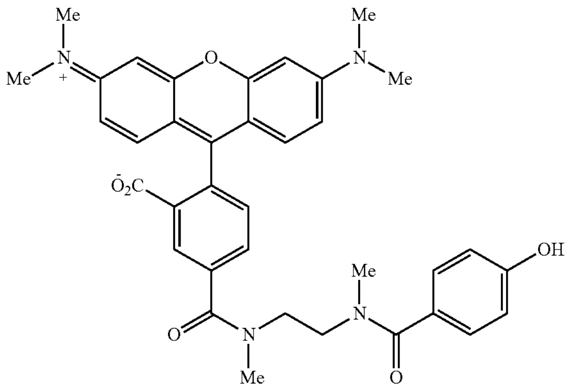

To a stirred mixture of 5-carboxytetramethylrhodamine (14.2 mg, 0.03 mmol) in DMF (100 μL), HATU (19.5 mg, 0.05 mmol) and N,N-diisopropylethylamine (50 μL, 0.3 mmol) were added at room temperature. After 5 min, a solution of N$^1$-Methyl-N$^2$-Methyl-N$^2$-4-hydroxybenzoyl-1,2-ethylenediamine (7.4 mg, 0.04 mmol) in DMF (40 μL) was added to the above mixture. The reaction was stirred at room temperature for 2 h. The reaction mixture was purified by preparative HPLC using solvent gradient 1 (Table 3, $T_R$=19.55 min) to obtain a dark purple solid (5.2 mg as a mixture with trifluoroacetic acid). Analytical HPLC using solvent gradient 11, $T_R$=18.08 min. MS (ESI+): m/z calculated for $[M+H]^+$ 621.3, found 621.5. ESI-HRMS(+) m/z calculated for $C_{36}H_{37}N_4O_6^+$ $[M+H]^+$ 621.2708, found 621.2733.

N$^1$-Methyl-N-biotin-N$^2$-methyl-N$^2$-4-hydroxybenzoyl-1,2-ethylenediamine

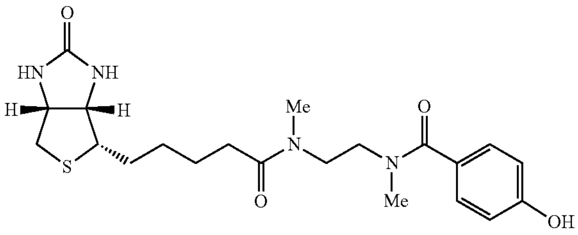 [SMILES: CN(CCN(C)C(=O)c1ccc(O)cc1)C(=O)CCCC[C@@H]1SC[C@@H]2NC(=O)N[C@@H]21]

To a stirred mixture of biotin (32 mg, 0.13 mmol) in DMF (300 μL), HATU (65.7 mg, 0.17 mmol) and N,N-diisopropyl-ethylamine (150 μL, 0.9 mmol) were added at room temperature. After 5 min, a solution of N$^1$-Methyl-N$^2$-Methyl-N$^2$-4-hydroxybenzoyl-1,2-ethylenediamine (39 mg, 0.19 mmol) in DMF (150 μL) was added to the above mixture. The reaction was stirred at room temperature for 1 h. The reaction mixture was purified by column chromatography ($CH_2C_{12}$:MeOH:$Et_3N$=8:1:0.2). The purified product was dried under vacuum to give a white solid (11.9 mg, 21% yield).

MS (ESI−): m/z calculated for $[M-H]^-$ 433.2, found 433.3. ESI-HRMS(+) m/z calculated for $C_{21}H_{31}N_4O_4S^+$ $[M+H]^+$ 435.2061, found 435.2064.

6-Chloro-6'-(methylsulfonyl)-3,3'-bipyridine

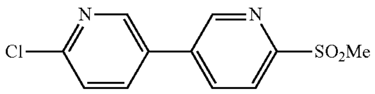 [SMILES: CS(=O)(=O)c1ccc(-c2ccc(Cl)nc2)cn1]

A mixture of THF and water (10 mL, 3:1, v/v) was added to a Schlenk flask containing 6-chloro-3-pyridinylboronic acid (47.2 mg, 0.3 mmol) and $K_2CO_3$ (82.9 mg, 0.6 mmol). The mixture was degassed with $N_2$ for 15 minutes before adding tetrakis(triphenylphosphine)palladium (57.8 mg, 0.05 mmol) and a solution of 5-iodo-2-(methylsulfonyl) pyridine (99.1 mg, 0.35 mmol) in THF (1 mL). The reaction mixture was degassed for additional two min. Under positive $N_2$ flow, the septum was replaced with a condenser. The stirred reaction mixture was heated to reflux for 15 hours under $N_2$. The reaction mixture was cooled to room temperature and filtered through a layer of diatomaceous earth (Celite®, commercially available from MilliporeSigma, Burlington, MA). THF was removed under vacuum. The resulting mixture was extracted with ethyl acetate (30 mL×4). The combined organic phase was dried over $MgSO_4$. The crude product was purified by column chromatography (ethyl acetate:hexanes=1:1) to afford a yellow crystalline solid (58.1 mg, 72% yield).

$^1H$ NMR (400 MHz, $CDCl_3$) δ 8.99-8.86 (m, 1H), 8.66 (d, J=2.6 Hz, 1H), 8.27-8.18 (m, 1H), 8.13 (dd, J=8.1, 2.1 Hz, 1H), 7.90 (dt, J=8.3, 1.8 Hz, 1H), 7.52 (d, J=8.3 Hz, 1H), 3.28 (d, J=1.0 Hz, 3H). $^{13}C\{^1H\}$ NMR (101 MHz, $CDCl_3$) δ 157.75, 152.71, 148.23, 148.13, 137.36, 136.43, 136.23, 130.76, 124.96, 121.45, 40.11. ESI-HRMS(+) m/z calculated for $C_{11}H_{10}ClN_2O_2S^+$ $[M+H]^+$ 269.0147, found 269.0137.

2-Chloro-2'-(methylsulfonyl)-4,4'-bipyridine

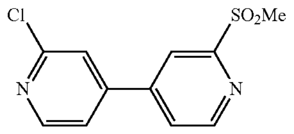 [SMILES: CS(=O)(=O)c1cc(-c2ccnc(Cl)c2)ccn1]

A mixture of THF and water (10 mL, 3:1, v/v) was added to a Schlenk flask containing 2-chloro-4-pyridinylboronic acid (39.4 mg, 0.25 mmol) and $K_2CO_3$ (82.9 mg, 0.6 mmol). The mixture was degassed with $N_2$ for 15 minutes before adding tetrakis(triphenylphosphine)palladium (57.8 mg, 0.05 mmol) and a solution of 4-iodo-2-(methylsulfonyl) pyridine (84.9 mg, 0.3 mmol) in THF (1 mL). The reaction mixture was degassed for additional two min. Under positive $N_2$ flow, the septum was replaced with a condenser. The stirred reaction mixture was heated to reflux for 15 hours under $N_2$. It was subsequently cooled to room temperature and filtered through a layer of Celite®. THF was removed under vacuum. The resulting mixture was extracted with ethyl acetate (30 mL×4). The combined organic phases were dried over $MgSO_4$. The crude product was purified by column chromatography (ethyl acetate:hexanes=2:1) to afford a yellow crystalline powder (35 mg, 42% yield).

$^1H$ NMR (400 MHz, $CDCl_3$) δ 8.87 (d, J=5.0 Hz, 1H), 8.58 (d, J=5.2 Hz, 1H), 8.31 (d, J=1.7 Hz, 1H), 7.77 (dd, J=5.0, 1.8 Hz, 1H), 7.63 (d, J=1.6 Hz, 1H), 7.51 (dd, J=5.2, 1.6 Hz, 1H), 3.30 (s, 3H). $^{13}C\{^1H\}$ NMR (101 MHz, $CDCl_3$) δ 159.59, 153.19, 151.26, 151.08, 147.19, 146.97, 125.07, 122.31, 120.31, 118.94, 40.10. ESI-HRMS(+) m/z calculated for $C_{11}H_{10}ClN_2O_2S^+$ $[M+H]^+$ 269.0147, found 269.0137.

2-Chloro-2'-(methylsulfonyl)-3,3'-bipyridine

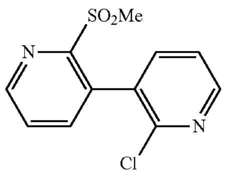 [SMILES: CS(=O)(=O)c1ncccc1-c1cccnc1Cl]

A mixture of THF and water (10 mL, 3:1, v/v) was added to a Schlenk flask containing 2-chloro-3-pyridinylboronic acid (47.2 mg, 0.3 mmol) and $K_2CO_3$ (82.9 mg, 0.6 mmol). The mixture was degassed with $N_2$ for 15 minutes before adding tetrakis(triphenylphosphine)palladium (57.8 mg, 0.05 mmol) and a solution of 3-iodo-2-(methylsulfonyl) pyridine (99.1 mg, 0.35 mmol) in THF (1 mL). Under positive $N_2$ flow, the septum was replaced with a condenser. The stirred reaction mixture was heated to reflux for 15 hours under $N_2$. The reaction mixture was cooled to room temperature and filtered through a layer of Celite©. THF was removed under vacuum. The resulting mixture was extracted with ethyl acetate (30 mL×4). The combined organic phase was dried over $MgSO_4$. The crude product was purified by column chromatography (ethyl acetate: hexanes=1.5:1 to 2:1) to afford a yellow crystalline solid (46.1 mg, 57% yield).

$^1H$ NMR (400 MHz, $CDCl_3$) δ 8.74 (dd, J=4.6, 1.6 Hz, 1H), 8.49 (dd, J=4.8, 1.9 Hz, 1H), 7.79 (ddd, J=11.6, 7.7, 1.8 Hz, 2H), 7.64 (dd, J=7.8, 4.7 Hz, 1H), 7.36 (dd, J=7.6, 4.8 Hz, 1H), 3.31 (s, 3H). $^{13}C\{^1H\}$ NMR (101 MHz, $CDCl_3$) δ 155.86, 149.96, 149.55, 148.90, 141.22, 140.14, 131.73, 131.01, 126.63, 121.92, 40.34. ESI-MS(+) m/z calculated for $[M+H]^+$ 269.0, found 269.1. ESI-HRMS(+) m/z calculated for $C_{11}H_{10}ClN_2O_2S^+$ $[M+H]^+$ 269.0147, found 269.0135.

5-Iodo-2-(methylsulfonyl)pyridine

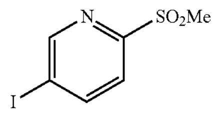 [SMILES: CS(=O)(=O)c1ccc(I)cn1]

An aliquot of $H_2O_2$(50 mM, 30 wt % in water, 5.11 mL) was added dropwise to a stirred mixture of 5-iodo-2-(methylthio)pyridine (251 mg, 1 mmol), sodium tungstate dihydrate (132 mg, 0.4 mmol), water (4 mL), and ethyl acetate (6 mL) at room temperature. The progress of the reaction was monitored by TLC. Upon the completion, the reaction mixture was cooled to 0° C. and quenched with solid $Na_2SO_3$ (0.5 g). The aqueous layer was separated from the organic phase and extracted with ethyl acetate (30 mL×3). The combined organic phase was dried over $MgSO_4$. The solvents were removed under vacuum. The crude product was purified by column chromatography (ethyl acetate: hexanes=1:1). A colorless crystals were obtained (235 mg, 83%).

$^1H$ NMR (400 MHz, $CDCl_3$) δ 8.93 (d, J=2.0 Hz, 1H), 8.31 (dd, J=8.2, 2.0 Hz, 1H), 7.85 (dd, J=8.1, 0.8 Hz, 1H), 3.21 (s, 3H). $^{13}C\{^1H\}$ NMR (101 MHz, $CDCl_3$) δ 157.08, 156.26, 146.75, 122.65, 98.57, 40.19. ESI-HRMS(+) m/z calculated for $C_6H_7INO_2S^+$ $[M+H]^+$ 283.9237, found 283.9217.

4-Iodo-2-(methylsulfonyl)pyridine

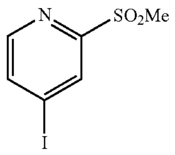 [SMILES: CS(=O)(=O)c1cc(I)ccn1]

An aliquot of $H_2O_2$ (36.5 mM, 30 wt % in water, 3.73 mL) was added dropwise to a stirred mixture of 4-iodo-2-(methylthio)pyridine (204 mg, 0.81 mmol), sodium tungstate dihydrate (17.2 mg, 0.052 mmol), water (3 mL), and ethyl acetate (6 mL) at room temperature. The progress of the reaction was monitored by TLC. Upon the completion, the reaction mixture was cooled to 0° C. and quenched with solid $Na_2SO_3$ (0.5 g). The aqueous layer was separated from the organic phase and extracted with ethyl acetate (30 mL×3). The combined organic phase was dried over $MgSO_4$. The solvents were removed under vacuum. The crude product was purified by column chromatography (ethyl acetate:hexanes=1:1). Colorless crystals were obtained (187 mg, 82% yield).

$^1H$ NMR (400 MHz, $CDCl_3$) δ 8.45 (d, J=1.5 Hz, 1H), 8.37 (d, J=5.0 Hz, 1H), 7.95 (dt, J=5.1, 1.3 Hz, 1H), 3.23 (s, 3H). $^{13}C\{^1H\}$ NMR (101 MHz, $CDCl_3$) δ 158.38, 150.27, 136.86, 130.41, 107.18, 40.13. ESI-MS(+) m/z calculated for $[M+H]^+$ 283.9, found 284.0. ESI-HRMS(+) m/z calculated for $C_6H_7INO_2S^+$ $[M+H]^+$ 283.9237, found 283.9217.

3-Iodo-2-(methylsulfonyl)pyridine

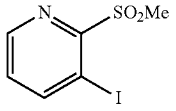 [SMILES: CS(=O)(=O)c1ncccc1I]

An aliquot of $H_2O_2$ (70 mM, 30 wt % in water, 7.15 mL) was added dropwise to a stirred mixture of 4-iodo-2-(methylthio)pyridine (251 mg, 1 mmol), sodium tungstate dihydrate (33 mg, 0.1 mmol), water (4 mL), and ethyl acetate (6 mL) at room temperature. The progress of the reaction was monitored by TLC. Upon the completion, the reaction mixture was cooled to 0° C. and quenched with solid $Na_2SO_3$ (0.5 g). The aqueous layer was separated from the organic phase and extracted with ethyl acetate (30 mL×3). The combined organic phase was dried over $MgSO_4$. The solvents were removed under vacuum. The crude product was purified by column chromatography (ethyl acetate: hexanes=1:1). Colorless crystals were obtained (209 mg, 74% yield).

$^1H$ NMR (400 MHz, $CDCl_3$) δ 8.57 (dd, J=4.7, 1.4 Hz, 1H), 8.40 (dt, J=8.0, 1.2 Hz, 1H), 7.25-7.18 (m, 1H), 3.44 (d, J=0.9 Hz, 3H). $^{13}C^1\{H\}$ NMR (101 MHz, $CDCl_3$) δ 158.19, 150.71, 147.07, 127.42, 85.05, 39.54. ESI-HRMS(+) m/z calculated for $C_6H_7INO_2S^+$ $[M+H]^+$ 283.9237, found 283.9229.

5-Iodo-2-(methylthio)pyridine

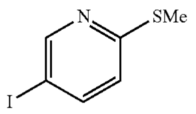

A portion of 2-fluoro-5-iodopyridine (446 mg, 2 mmol) and sodium thiomethoxide (147 mg, 2.1 mmol) were mixed in anhydrous THF (2 mL) in a vial in the glovebox. The reaction stirred at room temperature for 15 h. The solvent was removed under vacuum. The crude product was purified by column chromatography (hexanes:ethyl acetate=97:3) to give a white solid (495 mg, 99%).

$^1H$ NMR (400 MHz, $CDCl_3$) δ 8.62 (d, J=1.9 Hz, 1H), 7.72 (dd, J=8.5, 2.2 Hz, 1H), 6.99 (d, J=8.5 Hz, 1H), 2.53 (s, 3H). $^{13}C\{^1H\}$ NMR (101 MHz, $CDCl_3$) δ 159.36, 155.17, 143.58, 123.22, 86.92, 13.28. ESI-HRMS(+) m/z calculated for $C_6H_7INS^+$ $[M+H]^+$ 251.9338, found 251.9333.

4-Iodo-2-(methylthio)pyridine

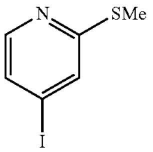

A portion of 2-fluoro-4-iodopyridine (446 mg, 2 mmol) and sodium thiomethoxide (147 mg, 2.1 mmol) were mixed in anhydrous THF (2 mL) in a vial in the glovebox. The reaction stirred at room temperature for 15 h. The solvent was removed under vacuum. The crude product was purified by column chromatography (hexanes:ethyl acetate=95:5) to give a white solid (435 mg, 87% yield).

$^1H$ NMR (400 MHz, $CDCl_3$) δ 8.07 (d, J=5.3 Hz, 1H), 7.57 (d, J=1.5 Hz, 1H), 7.33 (dd, J=5.3, 1.5 Hz, 1H), 2.54 (s, 3H). $^{13}C\{^1H\}$ NMR (101 MHz, $CDCl_3$) δ 161.67, 149.55, 130.15, 128.30, 105.08, 13.43, 0.14. ESI-HRMS(+) m/z calculated for $C_6H_7INS^+$ $[M+H]^+$ 251.9338, found 251.9325.

2-Fluoro-6-(methylthio)pyridine

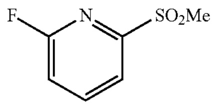

An aliquot of $H_2O_2$ (12 mM, 30 wt % in water, 1.23 mL) was added dropwise to a stirred mixture of 2-fluoro-6-(methylthio)pyridine (572 mg, 4 mmol), sodium tungstate dihydrate (132 mg, 0.4 mmol), water (1 mL), and ethyl acetate (8 mL) at room temperature. The progress of the reaction was monitored by TLC. After three hours, the reaction mixture was cooled to 0° C. and quenched with solid $Na_2SO_3$ (0.6 g). The aqueous layer was separated from the organic phase and extracted with ethyl acetate (30 mL×3). The combined organic phase was dried over $Na_2SO_4$. The solvents were removed under vacuum. The crude product was purified by column chromatography (ethyl acetate:hexanes=1:1). A slightly yellow oil was obtained (625 mg, 89%).

$^1H$ NMR (400 MHz, $CDCl_3$) δ 8.09 (dd, J=15.5, 7.4 Hz, 1H), 8.00 (ddd, J=7.4, 1.9, 0.6 Hz, 1H), 7.23 (ddd, J=8.2, 2.5, 0.5 Hz, 1H), 3.23 (s, 3H). $^{13}C\{^1H\}$ NMR (101 MHz, $CDCl_3$) δ 162.79 (d, J=250.0 Hz), 156.06 (d, J=11.8 Hz), 143.48 (d, J=7.9 Hz), 118.84 (d, J=4.1 Hz), 114.73 (d, J=35.4 Hz), 39.96 (s). ESI-HRMS(+) m/z calculated for $C_6H_7FNO_2S^+$ $[M+H]^+$ 176.0177, found 176.0162.

1-Azido-9-(4-methylthio-2-pyridyl)-3,6,9-trioxanonane

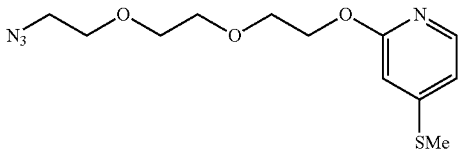 [SMILES: CSc1ccnc(OCCOCCOCCN=[N+]=[N-])c1]

A portion of sodium hydride (7.2 mg, 0.3 mmol) was added to a solution of 2-[2-(2-azidoethoxy)ethoxy]ethanol (43.8 mg, 38.6 μL, 0.25 mmol) in anhydrous 1,4-dioxane (1 mL) in a vial in the glovebox. A portion of 2-chloro-4-(methylthio)pyridine (47.9 mg, 0.3 mmol) was added to this mixture. The vial was transferred out of the glovebox and the reaction was heated at 100° C. for 1.5 h. The reaction was cooled to room temperature and quenched with MeOH (10 μL) under $N_2$ atmosphere. The solvent was removed under vacuum. The crude product was purified by column chromatography (ethyl acetate:hexanes=1:3 to 1:2 to 1:1). A colorless oil was obtained (51.4 mg, 69% yield).

$^1$H NMR (400 MHz, $CDCl_3$) δ 7.90 (d, J=5.6 Hz, 1H), 6.71 (dd, J=5.6, 1.6 Hz, 1H), 6.56 (d, J=1.4 Hz, 1H), 4.48-4.44 (m, 2H), 3.86-3.82 (m, 2H), 3.74-3.64 (m, 6H), 3.37 (t, J=5.1 Hz, 2H), 2.44 (s, 3H). $^{13}$C NMR (101 MHz, $CDCl_3$) δ 163.71, 153.08, 145.41, 114.55, 106.04, 70.82 (2C), 70.19, 69.91, 65.54, 50.79, 13.89. ESI-HRMS(+) m/z calculated for $C_{12}H_{19}N_4O_3S^+$ [M+H]$^+$ 299.1173, found 299.1186.

1-Azido-9-(4-methylsulfonyl-2-pyridyl)-3,6,9-trioxanonane

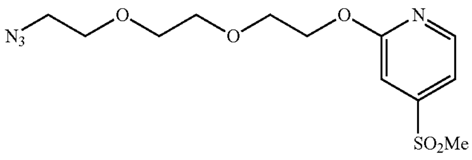 [SMILES: CS(=O)(=O)c1ccnc(OCCOCCOCCN=[N+]=[N-])c1]

An aliquot of $H_2O_2$ (4.08 mM, 30 wt % in water, 417 μL) was added dropwise to a stirred mixture of 1-azido-9-(4-methylthio-2-pyridyl)-3,6,9-trioxanonane (50.7 mg, 0.17 mmol), sodium tungstate dihydrate (5.6 mg, 0.017 mmol), water (213 μL), and ethyl acetate (1.7 mL) at room temperature. The progress of the reaction was monitored by TLC. After 12 h, the reaction mixture was cooled to 0° C. and quenched with solid $Na_2SO_3$ (0.5 g). The aqueous layer was separated from the organic phase and extracted with ethyl acetate (30 mL×3). The combined organic phase was dried over $Na_2SO_4$. The solvents were removed under vacuum. The crude product was purified by column chromatography (ethyl acetate: hexanes=1:1). A slightly yellow oil was obtained (49.2 mg, 88%).

$^1$H NMR (400 MHz, $CDCl_3$) δ 8.37 (d, J=5.3 Hz, 1H), 7.32 (dd, J=5.3, 1.4 Hz, 1H), 7.29 (s, 1H), 4.56-4.51 (m, 2H), 3.90-3.85 (m, 2H), 3.75-3.65 (m, 6H), 3.38 (t, J=5.0 Hz, 2H), 3.05 (s, 3H). $^{13}$C NMR (101 MHz, $CDCl_3$) δ 164.53, 150.90, 148.99, 113.16, 109.71, 70.89, 70.85, 70.23, 69.59, 66.35, 50.79, 43.80. ESI-MS(+) m/z calculated for [M+H]$^+$ 331.1, found 331.2. ESI-HRMS(+) m/z calculated for $C_{12}H_{19}N_4O_5S^+$ [M+H]$^+$ 331.1071, found 331.1059.

1-Azido-9-(2-methylthio-4-pyridyl)-3,6,9-trioxanonane

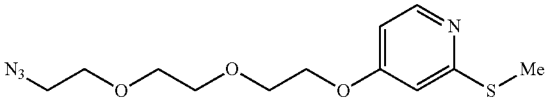 [SMILES: CSc1cc(OCCOCCOCCN=[N+]=[N-])ccn1]

Sodium thiomethoxide (30.8 mg, 0.44 mmol) was suspended in anhydrous THF (0.8 mL). A portion of 1-azido-9-(2-fluoro-4-pyridyl)-3,6,9-trioxanonane (108 mg, 0.4 mmol) in anhydrous THF (0.8 mL) was added to this mixture dropwise at 0° C. The reaction was gradually warmed to r.t. and stirred for 24 h. The solvents were evaporated and purified by column chromatography (ethyl acetate:hexanes=1:1). A colorless liquid was obtained (102 mg, 85% yield).

$^1$H NMR (400 MHz, $CDCl_3$) δ 8.24 (d, J=5.9 Hz, 1H), 6.71 (d, J=2.2 Hz, 1H), 6.58 (dd, J=5.8, 2.2 Hz, 1H), 4.17-4.13 (m, 2H), 3.87-3.84 (m, 2H), 3.74-3.64 (m, 6H), 3.37 (t, J=5.0 Hz, 2H), 2.55 (s, 3H). $^{13}$C NMR (101 MHz, $CDCl_3$) δ 165.13, 161.46, 149.93, 107.64, 106.76, 71.03, 70.84, 70.24, 69.48, 67.52, 50.77, 13.70. ESI-HRMS(+) m/z calculated for $C_{12}H_{19}N_4O_3S^+$ [M+H]$^+$ 299.1173, found 299.1166.

1-Azido-9-(2-methylsulfonyl-4-pyridyl)-3,6,9-trioxanonane

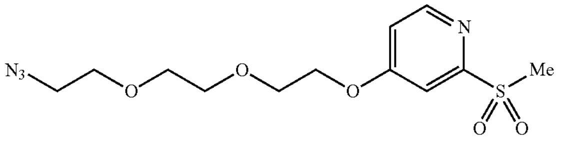 [SMILES: CS(=O)(=O)c1cc(OCCOCCOCCN=[N+]=[N-])ccn1]

An aliquot of $H_2O_2$ (2 mM, 30 wt % in water, 204 μL) was added in two portions dropwise to a stirred mixture of 1-azido-9-(2-methylthio-4-pyridyl)-3,6,9-trioxanonane (149 mg, 0.5 mMol), sodium tungstate dihydrate (16.5 mg, 0.05 mmol), water (3 mL), and ethyl acetate (6 mL) at room temperature. The progress of the reaction was monitored by TLC. The reaction mixture was cooled to 0° C. and quenched with solid $Na_2SO_3$ (0.5 g). The aqueous layer was separated from the organic phase and extracted with ethyl acetate (30 mL×3). The combined organic phase was dried over $Na_2SO_4$. The solvents were removed under vacuum. The crude product was purified by column chromatography (ethyl acetate:hexanes=3:1 to 1:0). A slightly yellow oil was obtained (116 mg, 70%).

$^1$H NMR (400 MHz, $CDCl_3$) δ 8.50 (t, J=9.2 Hz, 1H), 7.62 (d, J=2.4 Hz, 1H), 7.04 (dd, J=5.6, 2.5 Hz, 1H), 4.30-4.25 (m, 2H), 3.93-3.88 (m, 2H), 3.70 (ddd, J=10.3, 7.3, 4.1 Hz, 6H), 3.38 (t, J=5.0 Hz, 2H), 3.21 (s, 3H). $^{13}$C NMR (101 MHz, $CDCl_3$) δ 166.69, 159.66, 151.33, 114.28, 107.71, 71.12, 70.86, 70.29, 69.36, 68.47, 50.80, 40.13. ESI-MS(+) m/z calculated for [M+Na]$^+$ 353.1, found 353.2.

Example 1-a: N-methyl-2-fluoropyridinium iodide (CAP1-a)

In a 50 mL pressure tube, o-fluoropyridine (583 mg, 516 μL, 6 mmol) and methyl iodide (1.7 g, 747 μL, 12 mmol)

were mixed and heated at 80° C. A bright yellow solid was formed after 24 h and another portion of methyl iodide (1.7 g, 747 μL, 12 mmol) was added. The reaction was heated at 80° C. for an additional 72 h and then cooled to rt. The resultant solid was collected by suction filtration and washed with a small amount of cold MeCN (−20° C.). A slightly yellow solid was obtained (1.08 g, 75%). Crystallization was achieved by layering a solution of the solid in MeCN (about 6 mL) with dry $Et_2O$ (about 40 mL). White needles were formed after 24 h and collected after seven days (723 mg, 50%). The brown mother liquor (about 6 mL) was layered with $Et_2O$ (about 40 mL). White needles formed after 24 h and were collected after three days (101 mg, 7%). The overall yield was 57%. See Table 1 above for structure of CAP1-a as well as structures of CAP1-b, 1F, 1-$N_3$, 1-CCH, and 2-27.

$^1H$ NMR (400 MHz, $D_2O$) δ 8.79-8.59 (m, 2H), 7.99-7.80 (m, 2H), 4.28 (d, J=3.8 Hz, 3H). $^{19}F$ NMR (376 MHz, $D_2O$) δ −77.80 (s). MS (ESI+): m/z calculated for $M^+$ 112.1, found 112.5. ESI-HRMS(+) m/z calculated for $C_6H_7FN^+$ $[M]^+$ 112.0558, found 112.0555.

Example 1-b: N-methyl-2-fluoropyridinium tetrafluoroborate (CAP1-b)

In a 50 mL pressure tube, o-fluoropyridine (583 mg, 516 μL, 6 mmol) and methyl iodide (1.7 g, 747 μL, 12 mmol) were mixed and heated at 80° C. A bright yellow solid formed after 24 h and another portion of methyl iodide (1.7 g, 747 μL, 12 mmol) was added. The reaction was heated at 80° C. for an additional 72 h. The reaction was cooled to rt. The solid was collected by suction filtration and washed with a small amount of cold MeCN (−20° C.). A slightly yellow solid was obtained (1.08 g, 75%). Crystallization was achieved by layering a solution of the solid in MeCN (about 6 mL) with dry $Et_2O$ (about 40 mL). White needles formed after 24 h and were collected after seven days (723 mg, 50%). The brown mother liquor (about 6 mL) was layered with $Et_2O$ (about 40 mL). White needles formed after 24 h and were collected after three days (101 mg, 7%). The overall yield was 57%.

$^1H$ NMR (400 MHz, $D_2O$) δ 8.79-8.59 (m, 2H), 7.99-7.80 (m, 2H), 4.28 (d, J=3.8 Hz, 3H). $^{19}F$ NMR (376 MHz, $D_2O$) δ −77.80 (s). −151.87 (s, $^{10}BF_4^-$), −151.92 (s, $^{11}BF_4^-$).

Example 1-F: 2,6-Difluoro-N-methylpyridinium tetrafluoroborate (CAP1-F)

In a glovebox, 2,6-difluoropyridine (1.72 g, 1.35 mL, 14.9 mmol) and trimethyloxonium tetrafluoroborate (651 mg, 4.4 mmol) were added to a vial. The mixture was stirred. A brown slurry formed after 48 h. The mixture was diluted with anhydrous MeCN (about 4 mL) and layered with anhydrous $Et_2O$ (about 30 mL). Colorless needles formed after several days. The crystals were collected and washed with anhydrous $Et_2O$ and dried under vacuum (871 mg, 91% yield).

$^1H$ NMR (400 MHz, $CD_3CN$) δ 8.75 (tt, J=8.6, 6.8 Hz, 1H), 7.72 (d, J=8.6 Hz, 2H), 4.04 (t, J=3.1 Hz, 3H). $^{13}C^1\{H\}$ NMR (101 MHz, $CD_3CN$) δ 158.20 (d, J=282.2 Hz), 154.90 (t, J=12.1 Hz), 111.26-110.79 (m), 35.33 (t, J=6.2 Hz). $^{19}F$ NMR (377 MHz, $CD_3CN$) δ −79.54 (2F), −151.89 (s, $^{10}BF_4^-$), −151.94 (s, $^{11}BF_4^-$). ESI-HRMS(+) m/z calculated for $C_6H_6F_2N^+$ $[M]^+$ 130.0463, found 130.0463.

Example 1-$N_3$: 1-ethyl-4-(9-azido-1,4,7-trioxanonanyl)-2-fluoro-4-pyridinium tetrafluoroborate (CAP1-$N_3$)

In a glovebox, $Et_3OBF_4$ crystals (0.105 mmol, 20 mg) were added to 1-azido-9-(2-fluoro-4-pyridyl)-3,6,9-trioxanonane (27 mg, 0.1 mmol) in $CH_2Cl_2$ (400 μL). The reaction was stirred at r.t. for 24 h. The solvent was removed under vacuum. A sticky liquid was obtained (38.2 mg, 99%).

$^1H$ NMR (400 MHz, $CD_3CN$) δ 8.30 (dd, J=7.3, 5.9 Hz, 1H), 7.30 (dd, J=7.3, 2.7 Hz, 1H), 7.26 (dd, J=7.1, 2.7 Hz, 1H), 4.48-4.44 (m, 2H), 4.39 (qd, J=7.3, 2.3 Hz, 2H), 3.88-3.85 (m, 2H), 3.66-3.58 (m, 6H), 3.35 (t, J=4.9 Hz, 2H), 1.49 (t, J=7.3 Hz, 3H). $^{13}C^1\{H\}$ NMR (101 MHz, $CD_3CN$) δ 175.56 (d, J=14.0 Hz), 161.03 (d, J=272.7 Hz), 144.07 (d, J=4.7 Hz), 113.25 (d, J=1.4 Hz), 100.06 (d, J=24.7 Hz), 72.57 (s), 71.41 (s), 71.03 (s), 70.54 (s), 69.25 (s), 51.46 (s), 50.66 (d, J=4.5 Hz), 15.00 (s). $^{19}F$ NMR (377 MHz, $CD_3CN$) δ −82.57−−82.60 (m, 1F), −151.62 (s, $^{10}BF_4^-$), −151.67 (s, $^{11}BF_4^-$). MS (ESI+): m/z calculated for $[M]^+$ 299.2, found 299.2. MS (ESI+): m/z calculated for $[M]^+$ 299.2, found 299.2. ESI-HRMS(+) m/z calculated for $C_{13}H_{20}FN_4O_3^+$ $[M]^+$ 299.1514, found 299.1519).

Example 1-CCH: 1-Ethyl-4-(10-propargyl-1,4,7,10-tetraoxadecaneyl)-2-fluoro-4-pyridinium tetrafluoroborate (CAP1-CCH)

In a glovebox, $Et_3OBF_4$ crystals (0.105 mmol, 20 mg) were added to a solution of 1-(2-fluoro-4-pyridyl)-10-propargyl-1,4,7,10-tetraoxadecane (28.3 mg, 0.1 mmol) in $CH_2Cl_2$ (400 μL). The reaction was stirred at r.t. for 24 h. The solvent was removed under vacuum. A sticky liquid was obtained (39.5 mg, 99%).

$^1H$ NMR (400 MHz, $CD_3CN$) δ 8.31 (dd, J=7.2, 5.9 Hz, 1H), 7.32 (dd, J=7.3, 2.7 Hz, 1H), 7.26 (dd, J=7.1, 2.7 Hz, 1H), 4.49-4.44 (m, 2H), 4.40 (qd, J=7.3, 2.3 Hz, 2H), 4.14 (d, J=2.4 Hz, 2H), 3.89-3.84 (m, 2H), 3.65-3.53 (m, 8H), 2.71 (t, J=2.4 Hz, 1H), 1.50 (t, J=7.3 Hz, 3H). $^{13}C^1\{H\}$ NMR (101 MHz, $CD_3CN$) δ 175.55 (d, J=14.0 Hz), 161.03 (d, J=272.3 Hz) 144.12 (d, J=4.8 Hz), 113.26 (d, J=2.0 Hz), 100.10 (d, J=24.3 Hz), 80.94, 75.76, 72.58, 71.43, 71.03, 70.92, 69.93, 69.22, 58.69, 50.67 (d, J=4.8 Hz), 15.02. $^{19}F$ NMR (376 MHz, $CD_3CN$) δ −82.54-82.58 (m, 1F), −151.58 (s, $^{10}BF_4^-$), −151.63 (s, $^{11}BF_4^-$). MS (ESI+): m/z calculated for $M^+$ 312.4, found 312.2. MS (ESI+): m/z calculated for $M^+$ 312.4, found 312.2. ESI-HRMS(+) m/z calculated for $C_{16}H_{23}FNO_4^+$ $[M]^+$ 312.1606, found 312.1602.

Example 2: 2-Chloro-1,3-dimethyl-1H-benzimidazol-3-ium tetrafluoroborate (CAP2)

In a glovebox, 2-chloro-1-methyl-benzimidazole (666 mg, 4 mmol) and trimethyloxonium tetrafluoroborate (651 mg, 4.4 mmol) were mixed with anhydrous MeCN (4 mL). The mixture was stirred for 24 h. The mixture was filtered through a cotton plug and diluted with anhydrous MeCN (about 4 mL) and layered with anhydrous $Et_2O$ (about 30 mL). After seven days, formed colorless needles were collected and washed with anhydrous $Et_2O$ (953 mg, 89% yield).

$^1H$ NMR (400 MHz, $CD_3CN$) δ 7.88-7.82 (m, 2H), 7.75-7.69 (m, 2H), 4.02 (s, 6H). $^{13}C^1\{H\}$ NMR (101 MHz, $CD_3CN$) δ 141.93, 132.56, 128.36, 118.36, 113.93, 33.75. MS (ESI+): m/z calculated for $M^+$ 181.1, found 181.6. ESI-HRMS(+) m/z calculated for $C_9H_{10}ClN_2$+$[M]^+$ 181.0528, found 181.0528.

Example 3: N-Methyl-4-(methylsulfonyl)pyridinium tetrafluoroborate (CAP3)

In a glovebox, 4-(methylsulfonyl)pyridine (157 mg, 1 mmol) and trimethyloxonium tetrafluoroborate (177 mg, 1.2 mmol) were mixed in anhydrous $MeNO_2$ (200 μL). The reaction was stirred at rt for 36 h, which led to the formation of a large amount white solid. The reaction mixture was dissolved MeCN (10 mL) and filtered through a cotton plug. Diethyl ether was diffused into the filtrate. After a week, colorless crystals formed. The crystals were collected after seven days (235 mg, 91% yield).

$^1$H NMR (400 MHz, $CD_3CN$) δ 8.95 (d, J=6.2 Hz, 2H), 8.44 (dt, J=6.4, 2.6 Hz, 2H), 4.42 (s, 3H), 3.28 (s, 3H). $^{13}C\{^1H\}$ NMR (101 MHz, $CD_3CN$) δ 155.92 (t, J=3.3 Hz), 148.86 (t, J=9.5 Hz), 126.98, 50.17 (t, J=5.1 Hz), 43.35. $^{19}$F NMR (376 MHz, $CD_3CN$) δ −151.49 (s, $^{10}BF_4$), −151.55 (s, $^{11}BF_4^-$). MS (ESI+): m/z calculated for $M^+$ 172.2, found 172.2. ESI-HRMS(+) m/z calculated for $C_7H_{10}NO_2S^+$ $[M]^+$ 172.0427, found 172.0443.

Example 4: N-methyl-2-(methylsulfonyl)pyridinium tetrafluoroborate (CAP4)

In a glovebox, $Me_3OBF_4$ (222 mg, 1.5 mmol) was mixed with the o-(methyl-sulfonyl)pyridine (157 mg, 1 mmol). A portion of anhydrous $MeNO_2$ (100 μL) was added. The reaction was stirred at room temperature for 36 h, during which the white solid slowly dissolved. The reaction mixture was then dissolved in anhydrous MeCN (4 mL) and filtered through a 0.2 μm PTFE syringe filter. Diethyl ether was diffused into the filtrate at −35° C. After 24 h, additional diethyl ether (30 mL) was added to the top of the mixture. Colorless crystals were collected after a week (231 mg, 89% yield).

$^1$H NMR (400 MHz, $D_2O$) δ 9.13 (d, J=6.0 Hz, 1H), 8.87 (td, J=7.9, 1.1 Hz, 1H), 8.81 (dd, J=8.0, 1.6 Hz, 1H), 8.37 (ddd, J=7.7, 6.1, 1.6 Hz, 1H), 4.74 (s, 3H), 3.64 (s, 3H). $^{13}C^1\{H\}$ NMR (101 MHz, $D_2O$) δ 150.52, 148.30, 132.09, 130.32, 47.82, 42.95. ESI-HRMS(+) m/z calculated for $C_7H_{10}NO_2S^+$ $[M]^+$ 172.0427, found 172.0442.

Example 5: 2-Chloro-1-methyl-6-(methylsulfonyl) pyridin-1-ium tetrafluoroborate (CAP5)

A portion of 2-chloro-6-(methylsulfonyl)pyridine (96 mg, 0.5 mmol) and trimethyloxonium tetrafluoroborate (89 mg, 0.6 mmol) were mixed with anhydrous $CH_3NO_2$ (185 μL) in a vial in the glovebox. The reaction was stirred at room temperature for 36 hours. The reaction mixture was diluted with anhydrous $CH_3CN$ (4 mL) and filtered through a cotton plug. The filtrate was diffused with anhydrous $Et_2O$. Colorless crystals formed after seven days. The crystals were washed with $Et_2O$ and dried under vacuum (32 mg, 22%).

$^1$H NMR (400 MHz, $CD_3CN$) δ 8.79-8.62 (m, 2H), 8.42 (dd, J=7.8, 2.1 Hz, 1H), 4.61 (s, 3H), 3.52 (s, 3H). $^{13}C\{^1H\}$ NMR (101 MHz, $CD_3CN$) δ 154.18, 153.94, 149.28, 135.48, 130.13, 45.40, 44.50.

Example 6: 6-Chloro-1,1'-dimethyl-6'-(methylsulfonyl)-[3,3'-bipyridine]-1,1'-diium bis(tetrafluoroborate) (CAP6)

A portion of 6-chloro-6'-(methylsulfonyl)-3,3'-bipyridine (20 mg, 0.074 mmol) and trimethyloxonium tetrafluoroborate (46.1 mg, 0.312 mmol) were mixed with anhydrous $CH_3NO_2$ (200 μL) in a vial in the glovebox. The reaction was stirred at room temperature for 36 hours. The reaction mixture was diluted with anhydrous $CH_3CN$ (3 mL) and filtered through a cotton plug. The filtrate was diffused with anhydrous $CH_2Cl_2$. After six days, the off-white crystals were collected, washed with anhydrous $Et_2O$, and dried under vacuum (26 mg, 74%).

$^1$H NMR (400 MHz, $CD_3CN$) δ 9.31 (d, J=2.0 Hz, 1H), 9.23 (d, J=2.2 Hz, 1H), 9.06 (dd, J=8.4, 2.0 Hz, 1H), 8.86 (d, J=8.4 Hz, 1H), 8.82 (dd, J=8.7, 2.3 Hz, 1H), 8.37 (d, J=8.7 Hz, 1H), 4.74 (s, 3H), 4.43 (s, 3H), 3.55 (s, 3H). $^{13}C\{^1H\}$ NMR (101 MHz, $CD_3CN$) δ 151.93, 150.88, 150.29, 148.05, 147.33, 146.65, 137.59, 132.01, 131.84, 131.61, 49.47, 49.29, 44.46. ESI-HRMS(+) m/z calculated for $C_{13}H_{15}ClN_2O_2S^{2+}$ $[M]^{2+}$ 149.0266, found 149.0236.

Example 7: 2-Chloro-1,1'-dimethyl-2'-(methylsulfonyl)-[4,4'-bipyridine]-1,1'-diium bis(tetrafluoroborate) (CAP7)

A portion of 2-chloro-2'-(methylsulfonyl)-4,4'-bipyridine (26.9 mg, 0.1 mmol) and trimethyloxonium tetrafluoroborate (35.9 mg, 0.243 mmol) were mixed with anhydrous $CH_3NO_2$ (100 μL) in a vial in the glovebox. The reaction was stirred at room temperature for 24 hours. The reaction mixture was diluted with anhydrous $CH_3CN$ (2 mL) and filtered through a cotton plug. The filtrate was diffused with anhydrous $Et_2O$. After ten days, an off-white crystalline powder was collected, washed with anhydrous $Et_2O$, and dried under vacuum (20 mg, 42%).

$^1$H NMR (400 MHz, $CD_3CN$) δ 9.13 (d, J=6.3 Hz, 1H), 9.02-8.94 (m, 2H), 8.67 (q, J=3.0 Hz, 2H), 8.41 (dd, J=6.6, 2.2 Hz, 1H), 4.71 (s, 3H), 4.40 (s, 3H), 3.57 (s, 3H). $^{13}C\{^1H\}$ NMR (101 MHz, $CD_3CN$) δ 152.58, 152.49, 152.14, 150.86, 150.06, 149.78, 131.50, 130.33, 130.01, 126.05, 49.25, 48.92, 44.35. ESI-HRMS(+) m/z calculated for $C_{13}H_{15}ClN_2O_2S^{2+}$ $[M]^{2+}$ 149.0266, found 149.0223.

Example 8: 2-Chloro-1,1'-dimethyl-2'-(methylsulfonyl)-[3,3'-bipyridine]-1,1'-diium bis(tetrafluoroborate) (CAP8)

A portion of 2-chloro-2'-(methylsulfonyl)-3,3'-bipyridine (134 mg, 0.5 mmol) and trimethyloxonium tetrafluoroborate (178 mg, 1.2 mmol) were mixed with anhydrous $CH_3NO_2$ (330 μL) in a vial in the glovebox. The reaction was stirred at room temperature for 24 hours. The reaction mixture was diluted with anhydrous $CH_3CN$ (3 mL) and filtered through a cotton plug. The filtrate was diffused with anhydrous $CH_2Cl_2$. After seven days, an oil residue formed. This oil residue was separated from the solvents and dissolved in anhydrous $CH_3CN$ (5 mL) and diffused with $CH_2Cl_2$. After ten days, a white crystalline powder was collected, washed with anhydrous $Et_2O$, and dried under vacuum (183 mg, 77%).

$^1$H NMR (400 MHz, $CD_3CN$) δ 9.14 (d, J=6.0 Hz, 1H), 8.90 (d, J=6.3 Hz, 1H), 8.58 (d, J=8.3, Hz, 1H), 8.53-8.39 (m, 2H), 8.10 (dd, J=8.1, 6.2 Hz, 1H), 4.77 (s, 3H), 4.41 (s, 3H), 3.51 (s, 3H). $^{13}C\{^1H\}$ NMR (101 MHz, $CD_3CN$) δ 154.00, 151.84, 149.99, 149.57, 147.59, 147.24, 137.67, 137.40, 133.31, 127.02, 51.30, 49.80, 45.93. ESI-HRMS(+) m/z calculated for $C_{13}H_{15}ClN_2O_2S^{2+}$ $[M]^{2+}$ 149.0266, found 149.0234.

Example 9: N-Methyl-2-fluoro-6-(methylsulfonyl)pyridinium tetrafluoroborate (CAP9)

A portion of 2-fluoro-6-(methylsulfonyl)pyridine (175 mg, 1 mmol) and trimethyloxonium tetrafluoroborate (222 mg, 1.5 mmol) were mixed in anhydrous $CH_3NO_2$ (100 μL) in a glovebox. The reaction was stirred at room temperature for 36 h. The reaction mixture was diluted with anhydrous MeCN (4 mL) and filtered through a 0.2 μm PTFE syringe filter. The filtrate was layered with $Et_2O$ (25 mL) at −35° C. After seven days, the white crystals were collected and washed with $Et_2O$ (232 mg, 65% yield).

$^1$H NMR (400 MHz, $CD_3CN$) δ 8.87 (td, J=8.3, 5.8 Hz, 1H), 8.57 (d, J=7.9 Hz, 1H), 8.14 (dd, J=8.7, 4.4 Hz, 1H), 4.45 (d, J=4.2 Hz, 3H), 3.51 (s, 3H). $^{13}$C{$^1$H} NMR (101 MHz, $CD_3CN$) δ 161.54 (d, J=286.6 Hz), 153.44 (d, J=13.6 Hz), 149.86 (d, J=7.9 Hz), 128.06 (d, J=2.0 Hz), 120.80 (d, J=22.7 Hz), 44.52 (s), 39.75 (d, J=8.7 Hz). $^{19}$F NMR (377 MHz, $CD_3CN$) δ −68.44-68.55 (m, 1F), −151.89 (s, $^{10}BF_4^-$), −151.94 (s, $^{11}BF_4^-$). ESI-HRMS(+) m/z calculated for $C_7H_9FNO_2S^+$ $[M]^+$ 190.0333, found 190.0330.

Example 10: 6,6'-Difluoro-1,1'-dimethyl-[3,3'-bipyridine]-1,1'-diium bis(tetrafluoroborate) (CAP10)

In a glovebox, 6,6'-difluoro-3,3'-bipyridine (192 mg, 1 mmol) and trimethyloxonium tetrafluoroborate (325 mg, 2.2 mmol) were mixed in anhydrous MeCN (6 mL). The reaction was stirred at rt for 24 h, which led to the formation of a large amount white solid. The reaction mixture was dissolved in MeCN (8 mL) and filtered through a cotton plug. The filtrate was layered with $Et_2O$ (25 mL). After a week, colorless crystals formed. After seven days, the crystals were collected and washed with anhydrous $Et_2O$ (281 mg, 71% yield).

$^1$H NMR (400 MHz, $CD_3CN$) δ 8.95-8.87 (m, 4H), 8.02 (dd, J=8.7, 3.8 Hz, 2H), 4.29 (d, J=3.8 Hz, 6H). $^{13}$C$^1${H} NMR (101 MHz, $CD_3CN$) δ 160.61 (d, J=282.5 Hz), 150.88 (d, J=12.2 Hz), 144.58 (d, J=6.7 Hz), 130.62 (d, J=3.8 Hz), 116.28 (d, J=21.2 Hz), 43.43 (d, J=5.2 Hz). $^{19}$F NMR (377 MHz, $CD_3CN$) δ −77.00 (dt, J=7.7, 3.9 Hz, 2F), −151.45 (s, $^{10}BF_4^-$), −151.50 (s, $^{11}BF_4^-$).

Example 11: 6,6'-Difluoro-1,1'-dimethyl-[2,2'-bipyridine]-1,1'-diium bis(tetrafluoroborate) (CAP11)

In a glovebox, 6,6'-difluoro-2,2'-bipyridine (67 mg, 0.35 mmol) and trimethyloxonium tetrafluoroborate (123 mg, 2.4 mmol) were mixed in anhydrous $MeNO_2$ (150 μL). The reaction was stirred at rt for 36 h. The reaction mixture was dissolved in MeCN (10 mL) and filtered through a cotton plug. Anhydrous $Et_2O$ was diffused into the filtrate. After a week, colorless crystals formed. After seven days, the crystals were collected and washed with anhydrous $Et_2O$ (61.9 mg, 45% yield).

$^1$H NMR (400 MHz, $CD_3CN$) δ 8.89 (td, J=8.2, 6.0 Hz, 2H), 8.18 (ddd, J=8.8, 4.3, 0.8 Hz, 2H), 8.11 (d, J=7.7 Hz, 2H), 3.97 (d, J=4.1 Hz, 6H). $^{13}$C NMR (101 MHz, $CD_3CN$) δ 161.77 (d, J=284.8 Hz), 153.53 (d, J=13.6 Hz), 141.22 (d, J=7.4 Hz), 129.29 (d, J=2.7 Hz), 119.43 (d, J=21.6 Hz), 40.85 (d, J=7.1 Hz).

Example 12: 6,6'-Dimethylsulfonyl-1,1'-dimethyl-[3,3'-bipyridine]-1,1'-diium bis(tetrafluoroborate) (CAP12)

In a glovebox, 6,6'-dimethylsulfonyl-3,3'-bipyridine (250 mg, 0.8 mmol) and trimethyloxonium tetrafluoroborate (355 mg, 2.4 mmol) were mixed in anhydrous $CH_3NO_2$ (380 μL). The reaction was stirred at rt for 72 h to form a white slurry. The slurry was washed with anhydrous MeCN (1 mL×5) and anhydrous $Et_2O$ (1 mL). The solid was dried under vacuum to give a white powder (117 mg, 28% yield).

$^1$H NMR (400 MHz, $CD_3CN$) δ 9.35 (d, J=1.4 Hz, 2H), 9.12 (dd, J=8.4, 1.8 Hz, 2H), 8.91 (d, J=8.4 Hz, 2H), 4.76 (s, 6H), 3.57 (s, 6H). $^{13}$C NMR (101 MHz, $CD_3CN$) δ 152.57, 150.66, 148.00, 137.07, 132.23, 49.66, 44.55.

Example 13: 1-Methyl-2-(((trifluoromethyl)sulfonyl)oxy)pyridin-1-ium tetrafluoroborate (CAP13)

In a glovebox, 2-pyridyl trifluoromethanesulfonate (909 mg, 615 μL, 4 mmol) and trimethyloxonium tetrafluoroborate (592 mg, 4 mmol) were added to a vial. The reaction was stirred at rt for 48 h. The formed slurry was dissolved in MeCN (6 mL) and filtered through a cotton plug. The filtrate was layered with $Et_2O$ (25 mL). After ten days, colorless needles formed along with fine amorphous opaque material. The crystals were washed with $Et_2O$. The amorphous material was removed by pipetting. The crystals were collected and dried under vacuum (894 mg, 68% yield).

$^1$H NMR (400 MHz, $CD_3CN$) δ 8.80-8.66 (m, 2H), 8.14-7.98 (m, 2H), 4.25 (s, 3H). $^{13}$C$^1${H} NMR (101 MHz, $CD_3CN$) δ 151.81 (s), 150.85 (s), 148.51 (s), 127.92 (s), 120.43 (s), 119.36 (q, J=320.6 Hz), 45.32 (s). $^{19}$F NMR (376 MHz, $CD_3CN$) δ −72.91 (s, 3F), −151.89 (s, $^{10}BF_4^-$), −151.94 (s, $^{11}BF_4^-$).

Example 14: N-Methyl-2-fluoro-5-nitropyridinium tetrafluoroborate (CAP14)

In a glovebox, 2-fluoro-5-nitropyridine (284 mg, 2 mmol) and $Me_3OBF_4$ (311 mg, 2.1 mmol) were mixed in anhydrous MeCN (4 mL). The reaction was stirred at room temperature for 48 h. The reaction mixture was filtered through a cotton plug and diluted with MeCN (6 mL). The filtrate was layered with $Et_2O$ (about 25 mL). After seven days, colorless needles were collected and washed with $Et_2O$ (145 mg, 30% yield).

$^1$H NMR (400 MHz, $CD_3CN$) δ 9.52 (pseudo t, J=3.2 Hz, 1H), 9.29 (ddd, J=9.3, 4.5, 2.8 Hz, 1H), 8.05 (dd, J=9.4, 3.5 Hz, 1H), 4.29 (d, J=3.9 Hz, 1H). $^{13}$C$^1${H}NMR (101 MHz, $CD_3CN$) δ 162.72 (d, J=289.9 Hz), 146.68 (d, J=13.7 Hz), 144.16 (d, J=3.6 Hz), 143.52 (d, J=5.2 Hz), 116.75 (d, J=22.6 Hz), 44.24 (d, J=5.1 Hz). $^{19}$F NMR (377 MHz, $CD_3CN$) δ-68.65 (ddq, J=7.6, 3.8, 3.8 Hz, 1F), −151.91 (s, $^{10}BF_4^-$), −151.96 (s, $^{11}BF_4^-$).

Example 15: N-Methyl-2-chloro-5-nitropyridinium tetrafluoroborate (CAP15)

In a glovebox, 2-chloro-5-nitropyridine (634 mg, 4 mmol) and $Me_3OBF_4$ (651 mg, 4.4 mmol) were mixed in anhydrous MeCN (4 mL). The reaction was stirred at room temperature for 24 h. The reaction mixture was filtered through a cotton plug and diluted with MeCN (4 mL). The filtrate was layered with $Et_2O$ (about 30 mL). After seven days, slightly brown needles were collected and washed with $Et_2O$ (724 mg, 70% yield).

$^1$H NMR (400 MHz, $CD_3CN$) δ 9.70 (d, J=2.5 Hz, 1H), 9.12 (dd, J=9.0, 2.5 Hz, 1H), 8.37 (d, J=9.1 Hz, 1H), 4.43 (s, 3H). $^{13}$C$^1${H} NMR (101 MHz, CD3CN) δ 154.83 (s), 146.03 (s), 145.86 (s), 142.09 (s), 131.99 (s), 49.92 (s).

Example 16: 3,6-Dichloro-1-methylpyridazin-1-ium tetrafluoroborate (CAP16)

In a glovebox, 3,6-dichloropyridazine (447 mg, 3 mmol) and $Me_3OBF_4$ (887 mg, 6 mmol) were mixed in anhydrous MeCN (2 mL). The reaction was stirred at room temperature for 24 h. The reaction mixture was filtered through a cotton plug and diluted with MeCN (4 mL). The filtrate was layered with $Et_2O$ (about 25 mL). After seven days, a mixture of brown oil and colorless crystals formed. The oil was carefully removed using a pipette. The remaining oil on the crystals were quickly washed away using a small amount of anhydrous acetone (2 mL×2). The crystals were then washed with anhydrous $Et_2O$ (3 mL×4) and dried under vacuum. Colorless blocks were obtained (294 mg, 39% yield).

$^1$H NMR (400 MHz, $CD_3CN$) δ 8.53 (d, J=9.1 Hz, 1H), 8.46 (dq, J=9.1, 0.5 Hz, 1H), 4.56 (s, 3H). $^{13}C^1\{H\}$ NMR (101 MHz, $CD_3CN$) δ 157.42 (s), 156.05 (s), 140.90 (s), 140.42 (s), 52.85 (s). $^{19}$F NMR (376 MHz, $CD_3CN$) δ −152.05 (s, $^{10}BF_4^-$), −152.10 (s, $^{11}BF_4^-$).

Example 17: 2-Chloro-1,3-dimethylpyrimidine-1,3-diium bis(tetrafluoroborate) (CAP17)

In a glovebox, 2-chloropyrimidine (115 mg, 1 mmol) and $Me_3OBF_4$ (325 mg, 2.2 mmol) were mixed in anhydrous $MeNO_2$ (100 μL). The reaction was stirred at room temperature for 72 h. The reaction mixture was diluted with anhydrous MeCN (8 mL) and filtered through a cotton plug. The filtrate was layered with $Et_2O$ (about 25 mL). After seven days, a mixture of orange oil and colorless crystals formed. The oil was separated from the crystals using a pipette. The crystals, contaminated with a small amount of the orange oil, were dissolved in anhydrous MeCN and crystalized by diffusing $Et_2O$ into this solution. After seven days, colorless crystals formed along with a small amount of oil on the surface. The crystals were collected and dissolved in anhydrous MeCN. $Et_2O$ was diffused into this solution. After seven days, formed slightly yellow crystals were collected and washed with anhydrous $Et_2O$ (41 mg, blocks, 13% yield).

$^1$H NMR (400 MHz, $CD_3CN$) δ 8.63 (d, J=6.3 Hz, 1H), 6.84 (t, J=6.3 Hz, 1H), 3.72 (s, 3H). $^{13}C^1\{H\}$ NMR (101 MHz, $CD_3CN$) δ 161.47 (s), 148.99 (s), 104.46 (s), 41.56 (s). $^{19}$F NMR (376 MHz, $CD_3CN$) δ −151.80 (s, $^{10}BF_4$), −151.85 (s, $^{11}BF_4^-$).

Example 18: N-Methyl-2,4-difluoropyridinium tetrafluoroborate (CAP18)

In a glovebox, 2,4-difluoropyridine (230 mg, 182 μL, 2 mmol) and $Me_3OBF_4$ (443.7 mg, 3 mmol) were mixed in anhydrous MeCN (500 μL). The reaction was stirred at room temperature for 24 h. The reaction mixture was diluted with anhydrous MeCN (4 mL) and filtered through a cotton plug. The filtrate was layered with $Et_2O$ (25 mL) and stored at −40° C. After seven days, colorless blocks formed and were collected. The crystals were washed with $Et_2O$ (4 mL×3) and dried under vacuum (420 mg, 91% yield).

$^1$H NMR (400 MHz, $CD_3CN$) δ 8.61 (dd, J=12.9, 5.7 Hz, 1H), 7.75-7.63 (m, 2H), 4.13 (d, J=3.8 Hz, 3H). $^{13}$C NMR (101 MHz, $CD_3CN$) δ 176.15 (dd, J=280.5, 14.2 Hz), 162.22 (dd, J=277.6, 18.8 Hz), 148.51 (br dd, J=13.5, 5.6 Hz), 114.58 (dd, J=22.8, 3.0 Hz), 104.45 (dd, J=26.7, 24.5 Hz), 42.54 (d, J=5.1 Hz). $^{19}$F NMR (377 MHz, $CD_3CN$) δ −72.81 (dtq, J=30.0, 8.0, 3.9 Hz), −75.86 (dq, J=29.6, 6.3 Hz), −151.78 (s, $^{10}BF_4^-$), −151.83 (s, $^{11}BF_4^-$).

Example 19: N-Ethyl-2,4-difluoropyridinium tetrafluoroborate (CAP19)

In a glovebox, 2,4-difluoropyridine (230 mg, 182 μL, 2 mmol) and $Et_3OBF_4$ (399 mg, 2.1 mmol) were mixed in anhydrous $CH_2Cl_2$ (1 mL). The reaction was stirred at room temperature for 24 h. A large amount of white solid formed. The solvent was removed by pipette. The solid was dissolved in anhydrous MeCN (4 mL) and filtered through a cotton plug. The filtrate was layered with $Et_2O$ (25 mL). After three days, a small amount of crystals formed along with a large amount of colorless oil. The mixture was stored at −40° C. for four hours. The oil solidified. The solvents were quickly removed by pipette. The white crystalline solid was washed with anhydrous $Et_2O$ and dried under vacuum (356 mg, 77% yield).

$^1$H NMR (400 MHz, $CD_3CN$) δ 8.65 (dt, J=6.9, 5.6 Hz, 1H), 7.76-7.65 (m, 2H), 4.55 (qd, J=7.3, 2.5 Hz, 2H), 1.55 (t, J=7.3 Hz, 3H). $^{13}$C NMR (101 MHz, $CD_3CN$) δ 176.13 (dd, J=279.5, 13.3 Hz), 161.98 (br d, J=277.2 Hz), 147.32 (dd, J=13.1, 5.1 Hz), 115.09 (dd, J=22.8, 3.0 Hz), 104.90 (dd, J=26.8, 24.9 Hz), 52.52 (d, J=4.5 Hz), 14.81 (s). $^{19}$F NMR (377 MHz, $CD_3CN$) δ −75.31 (dtt, J=29.6, 4.8, 2.2 Hz, 1F), −75.87 (pseudo dq, J=29.6, 6.2 Hz, 1F), −151.79 (s, $^{10}BF_4^-$), −151.84 (s, $^{11}BF_4^-$).

Example 20: 2-Chloro-3-methylbenzothiazol-3-ium tetrafluoroborate (CAP20)

In a glovebox, 2-chlorobenzothiazole (678 mg, 4 mmol) and $Me_3OBF_4$ (651 mg, 4.4 mmol) were mixed in anhydrous MeCN (4 mL). The reaction was stirred at room temperature for 24 h. The reaction mixture was diluted with anhydrous MeCN (4 mL) and filtered through a cotton plug. The filtrate was layered with $Et_2O$ (30 mL). After seven days, the white crystals were collected and washed with $Et_2O$ (815 mg, 75% yield).

$^1$H NMR (400 MHz, $CD_3CN$) δ 8.26 (ddd, J=8.2, 1.2, 0.6 Hz, 1H), 8.11 (d, J=8.4 Hz, 1H), 7.95 (ddd, J=8.6, 7.4, 1.2 Hz, 1H), 7.87 (ddd, J=8.4, 7.4, 1.1 Hz, 1H), 4.24 (s, 3H). $^{13}C^1\{H\}$ NMR (101 MHz, $CD_3CN$) δ 165.40 (s), 141.44 (s), 131.53 (s), 130.66 (s), 130.00 (s), 125.15 (s), 118.14 (s), 38.47 (s). $^{19}$F NMR (377 MHz, $CD_3CN$) δ −151.70 (s, $^{10}BF_4^-$), −151.75 (s, $^{11}BF_4^-$).

Example 21:1-Ethyl-2-(9-azido-1,4,7-trioxanonanyl)-4-methylsulfonyl pyridinium tetrafluoroborate (CAP21)

A portion of triethyloxonium tetrafluoroborate (16 mg, 0.084 mmol) were added to a solution of 1-azido-9-(4-methylsulfonyl-2-pyridyl)-3,6,9-trioxanonane (26.4 mg, 0.080 mmol) in $CH_2Cl_2$ (320 μL). The reaction was stirred at r.t. for 24 h. The solvent was removed under vacuum. A sticky liquid was obtained (35.3 mg, 99%).

$^1$H NMR (400 MHz, $CD_2Cl_2$) δ 8.58 (d, J=6.6 Hz, 1H), 7.99 (d, J=5.3 Hz, 1H), 7.84 (dd, J=6.6, 1.4 Hz, 1H), 4.87-4.71 (m, 2H), 4.54 (q, J=7.2 Hz, 2H), 4.05-3.94 (m, 2H), 3.77-3.54 (m, 6H), 3.37-3.30 (m, 2H), 3.25 (s, 3H), 1.55 (t, J=7.3 Hz, 3H). $^{13}$C NMR (101 MHz, $CD_2Cl_2$) δ 161.44, 157.43, 144.85, 116.65, 111.98, 73.99, 71.06, 70.73, 70.18, 68.91, 52.47, 51.04, 43.22, 14.29. ESI-MS(+) m/z calculated for $[M+H]^+$ 359.1, found 359.2. ESI-HRMS(+) m/z calculated for $C_{14}H_{23}N_4O_5S^+$ $[M]^+$ 359.1384, found 359.1378.

Example 22:1-Ethyl-4-(9-azido-1,4,7-trioxanonanyl)-2-methylsulfonyl pyridinium tetrafluoroborate (CAP22)

A portion of triethyloxonium tetrafluoroborate (20 mg, 0.105 mmol) were added to a solution of 1-azido-9-(2- methylsulfonyl-4-pyridyl)-3,6,9-trioxanonane (33 mg, 0.1 mmol) in $CH_2Cl_2$ (400 μL). The reaction was stirred at r.t. for 24 h. The solvent was removed under vacuum. A sticky liquid was obtained (44.1 mg, 99%).

$^1H$ NMR (400 MHz, $CD_2Cl_2$) δ 8.71 (d, J=7.1 Hz, 1H), 8.07 (d, J=2.8 Hz, 1H), 7.66 (dd, J=7.1, 2.8 Hz, 1H), 4.83 (q, J=7.1 Hz, 2H), 4.60-4.56 (m, 2H), 3.96-3.92 (m, 2H), 3.70-3.60 (m, 6H), 3.46 (s, 3H), 3.35 (t, J=4.8 Hz, 2H), 1.64 (t, J=7.1 Hz, 3H). $^{13}C$ NMR (101 MHz, $CD_2Cl_2$) δ 172.66, 152.15, 150.42, 118.68, 116.47, 72.10, 71.15, 70.76, 70.21, 69.09, 55.04, 51.07, 44.68, 17.26. ESI-MS(+) m/z calculated for $[M+H]^+$ 359.1, found 359.3. ESI-HRMS(+) m/z calculated for $C_{14}H_{23}N_4O_5S^+$ $[M]^+$ 359.1384, found 359.1393.

Example 23: 1,3-dimethyl-2-(methylsulfonyl)-1H-benzo[d]imidazol-3-ium tetrafluoroborate (CAP23)

A portion of N-methyl-2-methylsulfonebenzoimidazole (52.6 mg, 0.25 mmol) was mixed with trimethyloxonium tetrafluoroborate (44.3, 0.3 mmol) in anhydrous nitromethane (25 μL) in a glovebox. The mixture was stirred at r.t. for 24 h, diluted with anhydrous acetonitrile (3 mL), and filtered through a cotton plug. The desired product was crystallized by diffusing anhydrous $Et_2O$ into the above filtrate. After seven days, clear crystals were obtained (47.6 mg, 61%).

1H NMR (400 MHz, D2O) δ 8.08–7.98 (m, 2H), δ 7.92–7.85 (m, 2H), 4.41 (s, 6H), 3.75 (s, 3H). The compound exhibits moderate stability in $D_2O$ and completely hydrolyzes at r.t. after 12 h.]

Example 24: 1,1'-(1,4-phenylenebis(methylene))bis(3-fluoropyridin-1-ium) diiodide (CAP24)

A mixture of 3-fluoropyridine (258 μL, 3 mmol) and 1,4-bis(bromomethyl)-benzene (264 mg, 1 mmol) in anhydrous acetonitrile (1 mL) was heated at 80° C. for 72 h. The formed solid was suspended in MeCN (2 mL) and stirred for 30 min. The solid was isolated by suction filtration and washed with MeCN. The product was dried under vacuum to give a white solid (450 mg, 98% yield).

$^1H$ NMR (400 MHz, $D_2O$) δ 9.11-8.99 (m, 2H), 8.87 (d, J=6.0 Hz, 2H), 8.51-8.36 (m, 2H), 8.20-8.07 (m, 2H), 7.57 (d, J=0.4 Hz, 4H), 5.90 (s, 4H). $^{19}F$ NMR (376 MHz, $D_2O$) δ −114.7 (ddd, J=7.1, 5.4, 3.4 Hz).

Example 25: N-Methyl-3-(methylsulfonyl)pyridinium tetrafluoroborate (CAP25)

3-(Methylsulfonyl)pyridinium tetrafluoroborate is synthesized by methylating known compound 3-(methylsulfonyl) pyridine with trimethyloxonium tetrafluoroborate in anhydrous nitromethane. The reaction is carried out under conditions similar to that for preparing pyridinium salts described above.

Example 26: N-Methyl-3-(N',N'-dimethylphenylsulfoximinium) pyridinium bis(tetrafluoroborate) (CAP26)

CAP26 is synthesized via two steps starting with a known compound, 3-(phenylsulfoximine) pyridine (see *Org. Lett.* 2020, 22, 2776). The imine nitrogen of 3-(phenylsulfoximine)pyridine is methylated with trimethyloxonium tetrafluoroborate to give 3-(N'-methylphenylsulfoximine)pyridine (see *J. Fluorine Chem.* 2011, 132, 792). This synthetic intermediate, 3-(N'-methylphenylsulfoximine)pyridine, is further methylated with excess trimethyloxonium tetrafluoroborate in anhydrous nitromethane under conditions similar to those for preparing pyridinium salts described above, generating the desired dicationic salt.

Following a similar procedure, CAP27 can also be prepared using commercially available reagents.

Example 27: Labeling Glutathione (GSH) Using CAP1-a

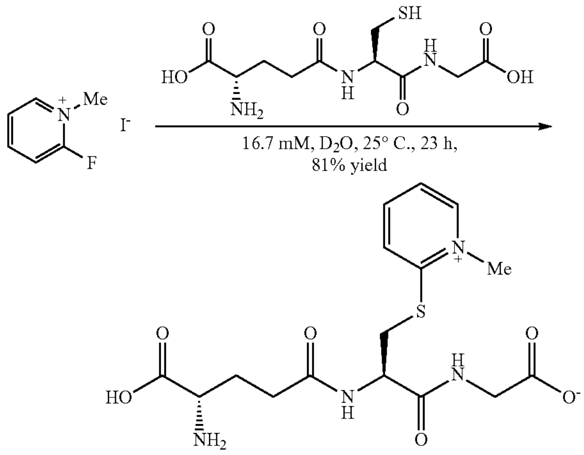

A stock solution of CAP1-a (2.39 mg, 0.01 mmol) in $D_2O$ (300 μL, 33.3 mM) and GSH (3.09 mg, 0.01 mM) in $D_2O$ (300 μL, 33.3 mM) were mixed and kept at 25° C. The progress of the reaction was monitored by $^1H$ NMR spectroscopy at 25° C. According to the $^1H$ NMR integration, the GSH-CAP1-a was obtained in 81% yield after 23 h.

$^1H$ NMR (400 MHz, $D_2O$) δ 8.68 (dd, J=6.7, 5.8 Hz, 1H), 8.32 (dt, J=7.4, 1.3 Hz, 1H), 8.04 (d, J=8.2 Hz, 1H), 7.69 (ddd, J=7.6, 6.4, 1.2 Hz, 1H), 4.85 (dd, J=7.9, 5.6 Hz, 1H), 4.19 (s, 3H), 3.98 (s, 1H), 3.97 (s, 1H), 3.91 (dd, J=14.2, 5.6 Hz, 1H), 3.86 (t, J=6.5 Hz, 1H), 3.70 (dd, J=14.2, 8.0 Hz, 1H), 2.51 (dd, J=8.9, 6.3 Hz, 2H), 2.23-2.07 (m, 2H). $^{13}C^1\{H\}$ NMR (101 MHz, $D_2O$) δ 174.44, 172.87, 171.94, 171.06, 158.43, 146.85, 143.72, 125.50, 123.02, 52.56, 51.62, 46.21, 41.23, 33.62, 30.96, 25.47. MS (ESI+): m/z calculated for $M^+$ 399.1, found 399.1.

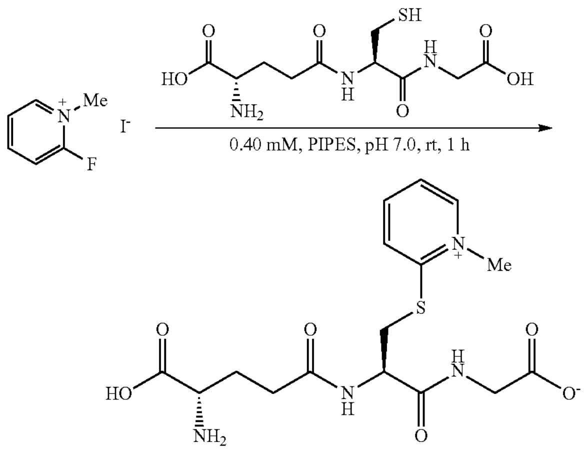

The reaction was performed again under the procedure as follows. To a mixture of 50 mM PIPES buffer (40 μL, pH 7) and water (355 μL), an aliquot of GSH (1.6 μL, 100 mM in $H_2O$) was added. To this mixture, CAP1-a (3.2 μL, 50 mM in $H_2O$) was added. The mixture was kept at room temperature for 1 h and then purified by HPLC using solvent gradient 2 (Table 3, semi prep HPLC $T_R$=12.31 min) to obtain a white solid as a trifluoroacetic acid salt. Analytical HPLC using solvent gradient 11, $T_R$=3.37 min.

MS (ESI+): m/z calculated for M+ 399.1, found 399.1. ESI-HRMS(+) m/z calculated for $C_{16}H_{23}N_4O_6S^+$ $M^+$ 399.1333, found 399.1320. The structure of the product was also confirmed by tandem MS study.

Example 28: Labeling GSH Using CAP1-$N_3$

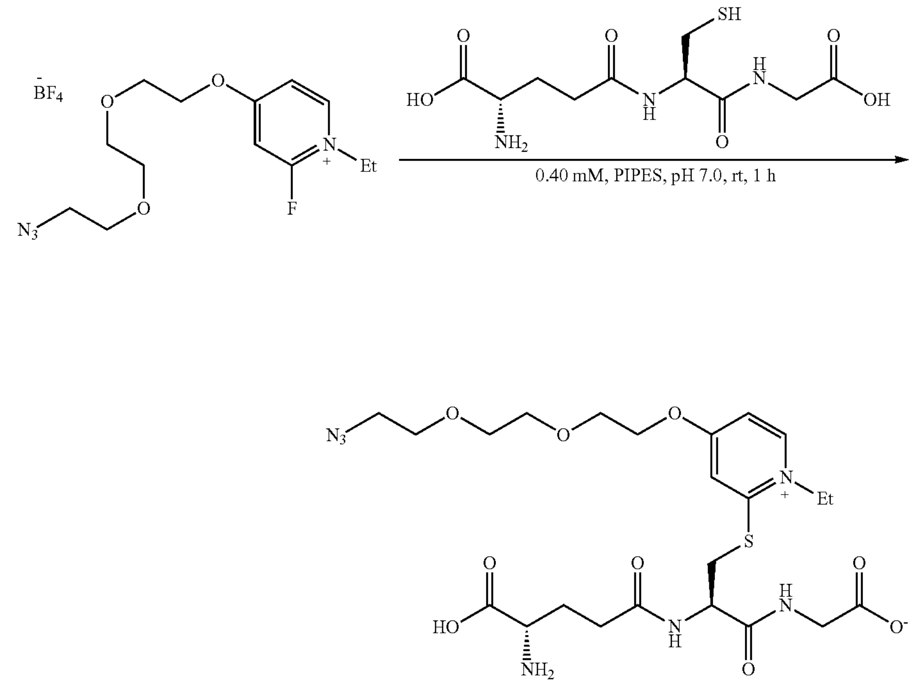

To a mixture of 50 mM PIPES buffer (40 μL, pH 7) and water (355 μL), an aliquot of GSH (1.6 μL, 100 mM in $H_2O$) was added. To this mixture, CAP1-$N_3$ (3.2 μL, 50 mM in $H_2O$) was added. The mixture was kept at room temperature for 1 h. The reaction mixture was purified by HPLC using solvent gradient 3 (Table 3, semi prep HPLC $T_R$=8.48 min) to obtain a white solid as a trifluoroacetic acid salt. Analytical HPLC using solvent gradient 11, $T_R$=11.97 min.

MS (ESI+): m/z calculated for $M^+$ 586.2, found 586.4. ESI-HRMS(+) m/z calculated for $C_{23}H_{36}N_7O_9S^+$ $M^+$ 586.2290, found 586.2276. The structure of the product was also confirmed by tandem MS study.

Example 29: Labeling GSH Using CAP1-CCH

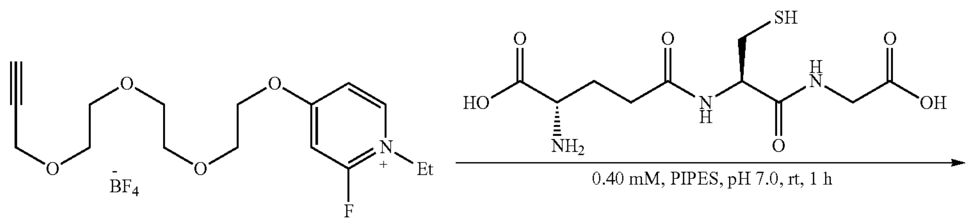

-continued

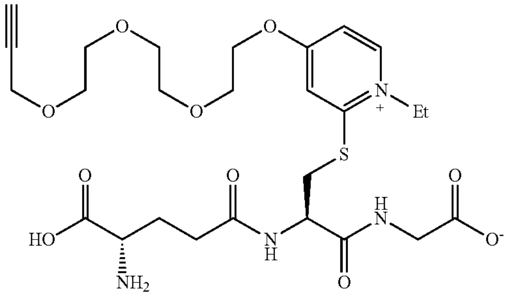

To a mixture of 50 mM PIPES buffer (40 μL, pH 7) and water (355 μL), an aliquot of GSH (1.6 μL, 100 mM in $H_2O$) was added. To this mixture, CAP1-CCH (3.2 μL, 50 mM in $H_2O$) was added. The mixture was kept at room temperature for 1 h. The reaction mixture was purified by HPLC using solvent gradient 3 (Table 3, semi prep HPLC $T_R$=8.50 min) to obtain a white solid as a trifluoroacetic acid salt. Analytical HPLC using solvent gradient 11, $T_R$=11.99 min.

MS (ESI+): m/z calculated for $M^+$ 599.2, found 599.4. ESI-HRMS(+) m/z calculated for $C_{26}H_{39}N_4O_{10}S^+$ $M^+$ 599.2382, found 599.2372. The structure of the product was also confirmed by tandem MS study.

Example 30: One-Pot Two-Step Labeling of GSH Using CAP1-F and Phenol in PIPES Buffer To a mixture of PIPES buffer (31.6 μL, pH 7) and PhOH (4 μL, 100 mM in MeCN), an aliquot of CAP1-F (4.4 μL, 100 mM in MeCN) was added. This mixture was kept at room temperature for 15 min. An aliquot of this reaction mixture (16 μL) was added to a mixture of GSH (1.6 μL, 100 mM in $H_2O$), 50 mM PIPES buffer (40 μL, pH 7), and water (342 μL). The mixture was kept at room temperature for 1 h. The reaction mixture was purified by HPLC using solvent gradient 4 (Table 3, semi prep HPLC $T_R$=8.67 min) to obtain a white solid as a trifluoroacetic acid salt. Analytical HPLC using solvent gradient 11, $T_R$=11.94 min.

MS (ESI+): m/z calculated for $M^+$ 491.2, found 491.2. ESI-HRMS(+) m/z calculated for $C_{22}H_{27}N_4O_7S^+$ $M^+$ 491.1595, found 491.1606. The structure of the product was also confirmed by tandem MS study.

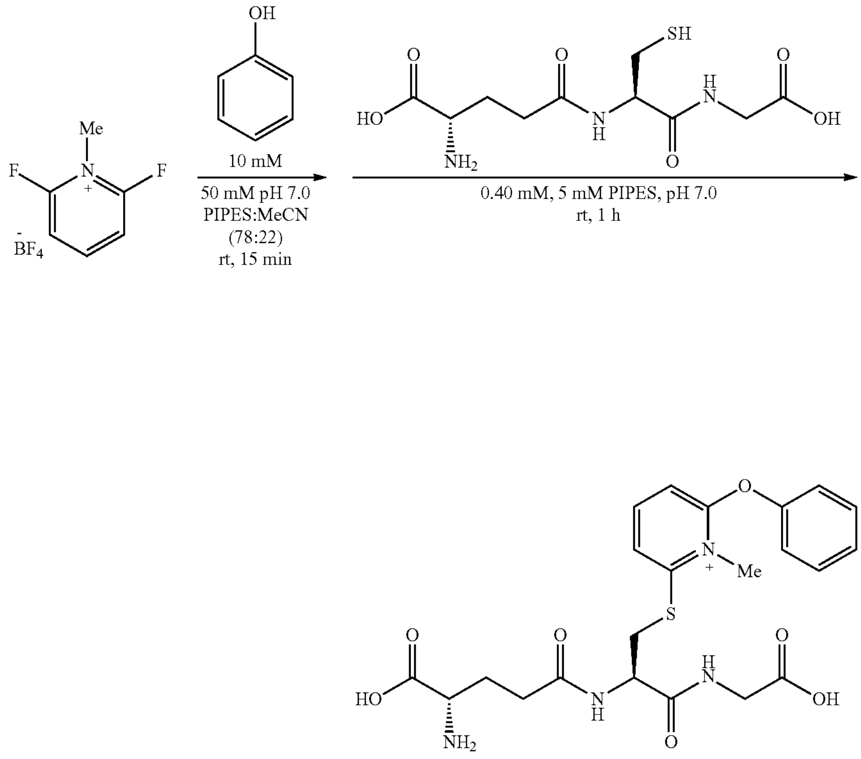

Example 31: One-Pot Two-Step Labeling of GSH Using CAP1-F and Phenol with DIPEA in MeCN and then in PIPES Buffer

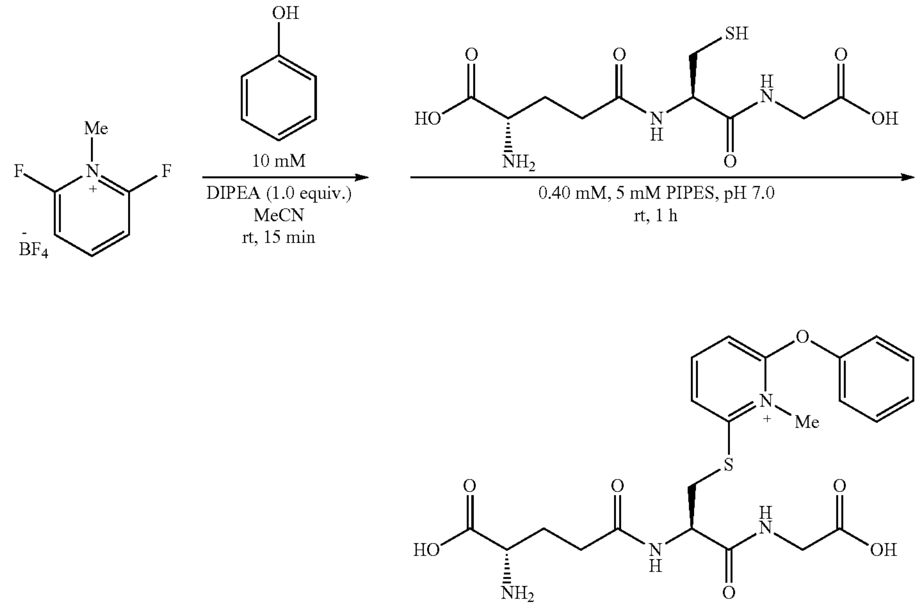

To a mixture of DIPEA (50 μL, 100 mM in MeCN) and PhOH (50 μL, 100 mM in MeCN) in MeCN (350 μL), an aliquot of CAP1-F (50 μL, 100 mM in MeCN) was added. This mixture was kept at room temperature for 20 min. An aliquot of this reaction mixture (16 μL) was added to 50 mM PIPES buffer (40 μL). The mixture was diluted with water (342 μL). An aliquot of GSH (1.6 μL, 100 mM in $H_2O$) was then added to this mixture. The mixture was kept at room temperature for 1 h. The reaction mixture was purified by HPLC using solvent gradient 4 (Table 3, semi prep HPLC $T_R$=8.67 min) to obtain a white solid as a trifluoroacetic acid salt. MS (ESI+): m/z calculated for $M^+$ 491.2, found 491.2.

Example 32: One-Pot Two-Step Labeling of GSH Using CAP1-F and Phenol with DIPEA in MeCN and DMF and then in PIPES Buffer

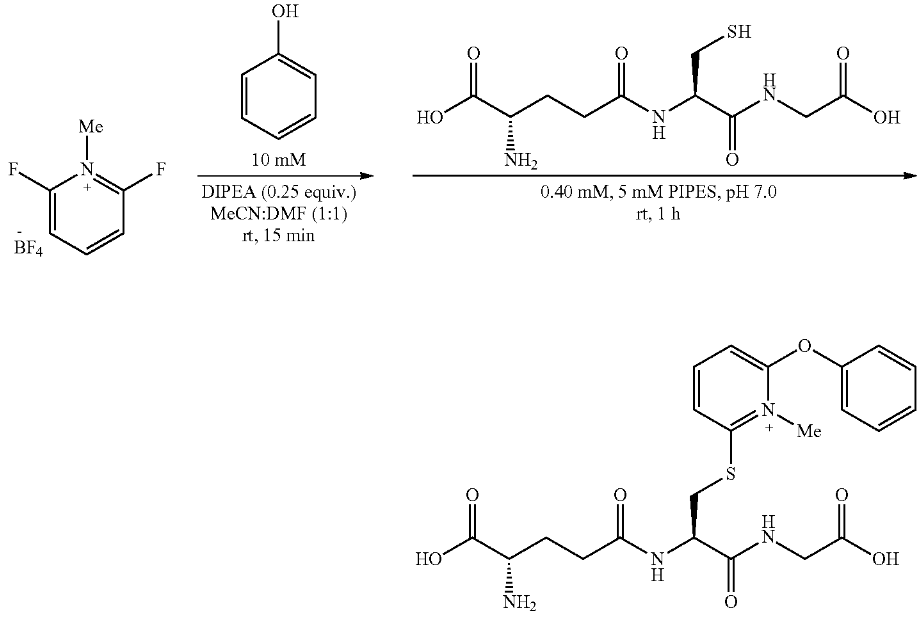

To a mixture of DIPEA (12.5 μL, 100 mM in MeCN) and PhOH (50 μL, 100 mM in MeCN) in MeCN (137.5 μL) and DMF (250 μL), an aliquot of CAP1-F (50 μL, 100 mM in MeCN) was added. This mixture was kept at room temperature for 20 min. An aliquot of this reaction mixture (16 μL) was added to 50 mM PIPES buffer (40 μL). The mixture was diluted with water (342 μL). An aliquot of GSH (1.6 μL, 100 mM in $H_2O$) was then added to this mixture. The mixture was kept at room temperature for 1 h. The reaction mixture was purified by HPLC using solvent gradient 4 (Table 3, semi prep HPLC $T_R$=8.67 min) to obtain a white solid as a trifluoroacetic acid salt. MS (ESI+): m/z calculated for $M^+$ 491.2, found 491.2.

Example 33: One-Pot Two-Step Labeling of GSH Using CAP1-F and Tetramethylrhodamine Phenol Derivative in PIPES Buffer

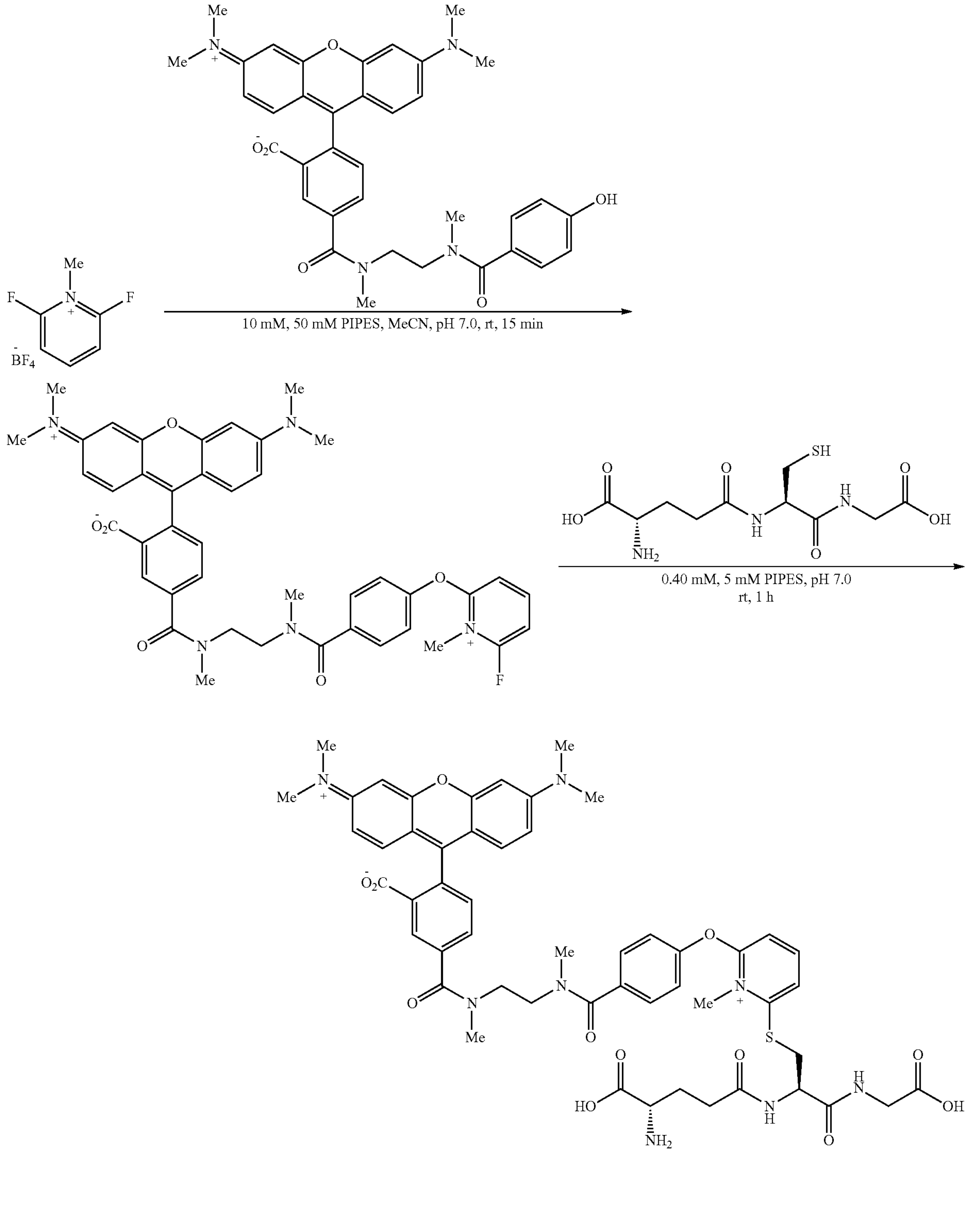

To a mixture of PIPES buffer (24.2 μL, pH 7) and tetramethylrhodamine phenol derivative (11.4 μL, 35 mM in MeCN), an aliquot of CAP1-F (4.4 μL, 100 mM in MeCN) was added. This mixture was kept at room temperature for 15 min. An aliquot of this reaction mixture (16 μL) was added to a mixture of GSH (1.6 μL, 100 mM in $H_2O$), 50 mM PIPES buffer (40 μL, pH 7), and water (342 μL). The reaction mixture was purified by HPLC using solvent gradient 5 (Table 3, semi prep HPLC $T_R$=12.13 min) to obtain a purple solid as a trifluoroacetic acid salt. Analytical HPLC using solvent gradient 11, $T_R$=18.08 min.

MS (ESI+): m/z calculated for $[M+H]^{2+}$ 509.2, found 509.6. ESI-HRMS(+) m/z calculated for $C_{52}H_{58}N_8O_{12}S^{2+}$ $M^+$ 509.1942, found 509.1931. The structure of the product was also confirmed by tandem MS study.

Example 34: One-Pot Two-Step Labeling of GSH Using CAP1-F and Biotin Phenol Derivative in PIPES Buffer To a mixture of PIPES buffer (27.6 μL, pH 7) and biotin phenol derivative (8 μL, 50 mM in MeCN), an aliquot of CAP1-F (4.4 μL, 100 mM in MeCN) was added. This mixture was kept at room temperature for 15 min. An aliquot of this reaction mixture (16 μL) was added to a mixture of GSH (1.6 μL, 100 mM in $H_2O$), 50 mM PIPES buffer (40 μL, pH 7), and water (342 μL). The reaction mixture was purified by HPLC using solvent gradient 6 (Table 3, semi prep HPLC $T_R$=12.96 min) to obtain a white solid as a trifluoroacetic acid salt. Analytical HPLC using solvent gradient 11, $T_R$=12.38 min.

MS (ESI+): m/z calculated for $[M+H]^{2+}$ 416.1, found 416.4. ESI-HRMS(+) m/z calculated for $C_{37}H_{52}N_8O_{10}S^{2+}$ $M^+$ 416.1619, found 416.1612. The structure of the product was also confirmed by tandem MS study.

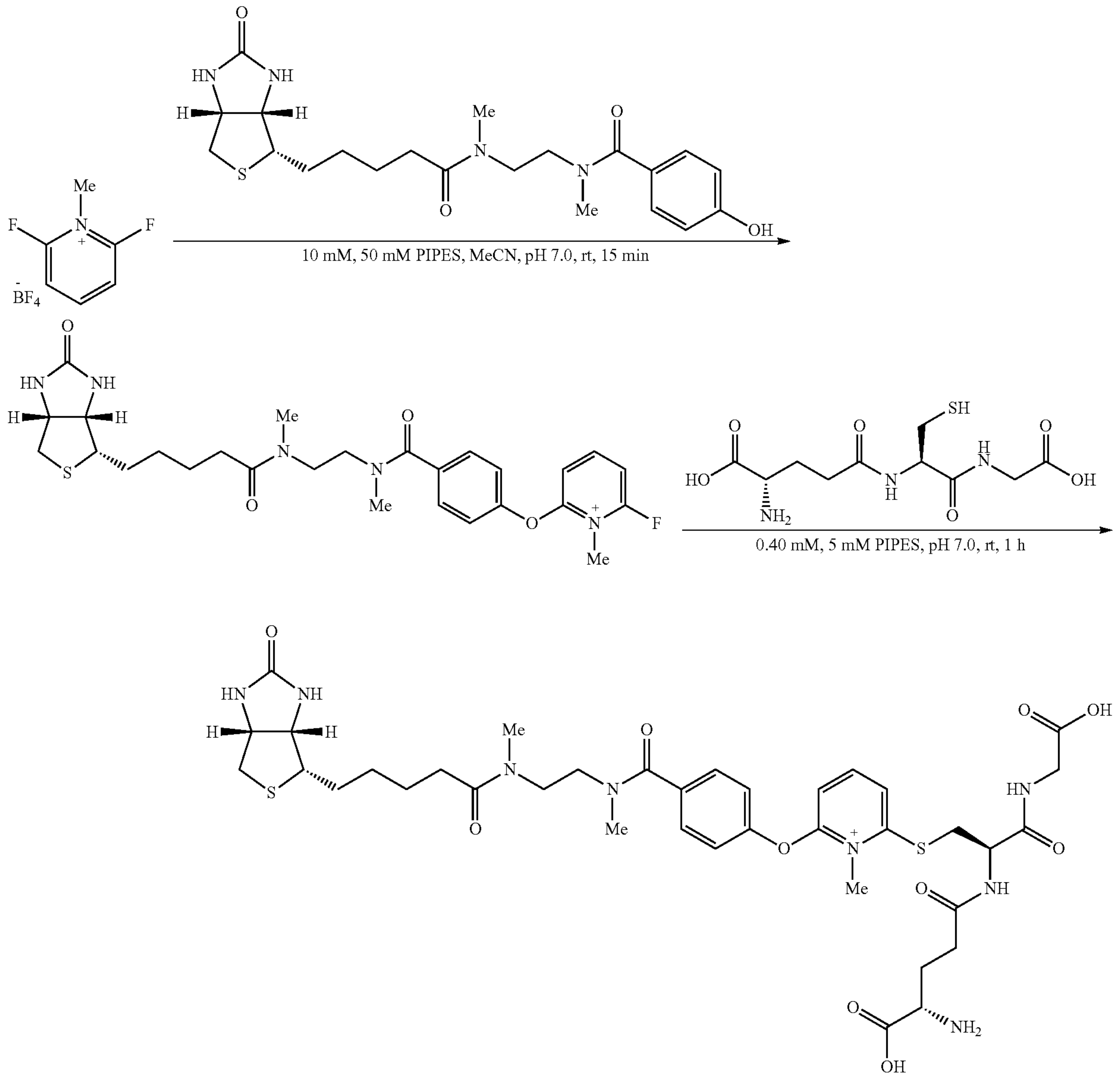

Example 35: Labeling GSH Using CAP2

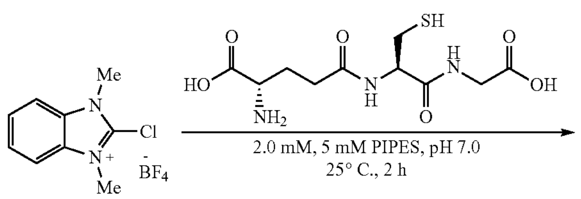

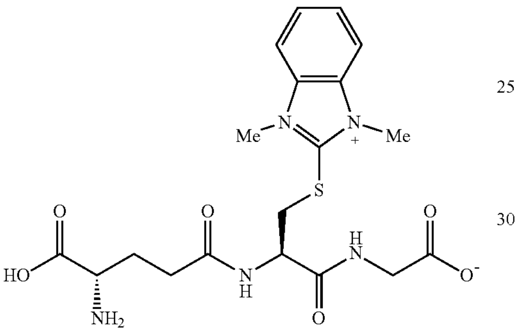

To a mixture of 50 mM PIPES buffer (40 μL, pH 7) and water (336 μL), an aliquot of GSH (8 μL, 100 mM in $H_2O$) was added. To this mixture, CAP2 (16 μL, 50 mM in $H_2O$) was added. The reaction mixture was purified by HPLC using solvent gradient 7 (Table 3, semi prep HPLC $T_R$=8.86 min) to obtain a white solid as a trifluoroacetic acid salt. Analytical HPLC using solvent gradient 11, $T_R$=6.22 min. to obtain a white solid as a trifluoroacetic acid salt.

MS (ESI+): m/z calculated for $[M]^+$ 452.2, found 226.6. ESI-HRMS(+) m/z calculated for $C_{19}H_{26}N_5O_6S^+$ $M^+$ 452.1599, found 452.1603. The structure of the product was also confirmed by tandem MS study.

Example 36: Labeling Reduced Oxytocin Using CAP1

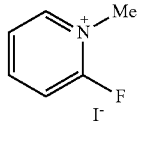

+

-continued

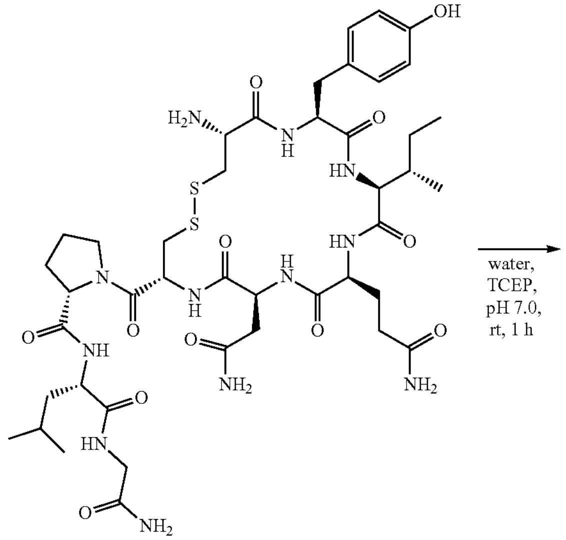

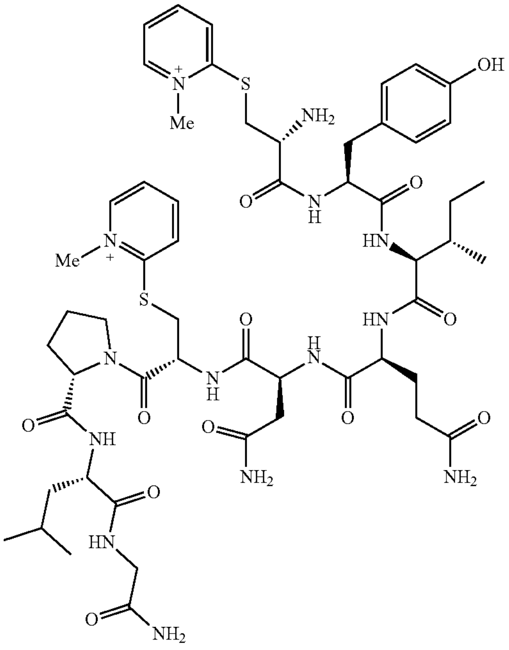

A stock solution of oxytocin (8 μL, 20 mM in water) was mixed with TCEP (4 μL, 0.5 M, pH 7) and then diluted with water (228 μL). After 5 min, an aliquot of CAP1 (160 μL, 5 mM) was added to the above mixture. The mixture was kept at room temperature for 1 h. The reaction mixture was purified by HPLC using solvent gradient 8 (Table 3, semi prep HPLC $T_R$=12.96 min) to obtain a white solid as a trifluoroacetic acid salt. Analytical HPLC using solvent gradient 11, $T_R$=12.03 min.

MS (ESI+): m/z calculated for $M^{2+}$ 596.3, found 596.6. ESI-HRMS(+) m/z calculated for $C_{55}H_{80}N_{14}O_{12}S_2^{2+}$ $M^{2+}$ 596.2756, found 596.2714. The structure of the product was also confirmed by tandem MS study.

Example 37: Labeling Reduced Oxytocin Using CAP10

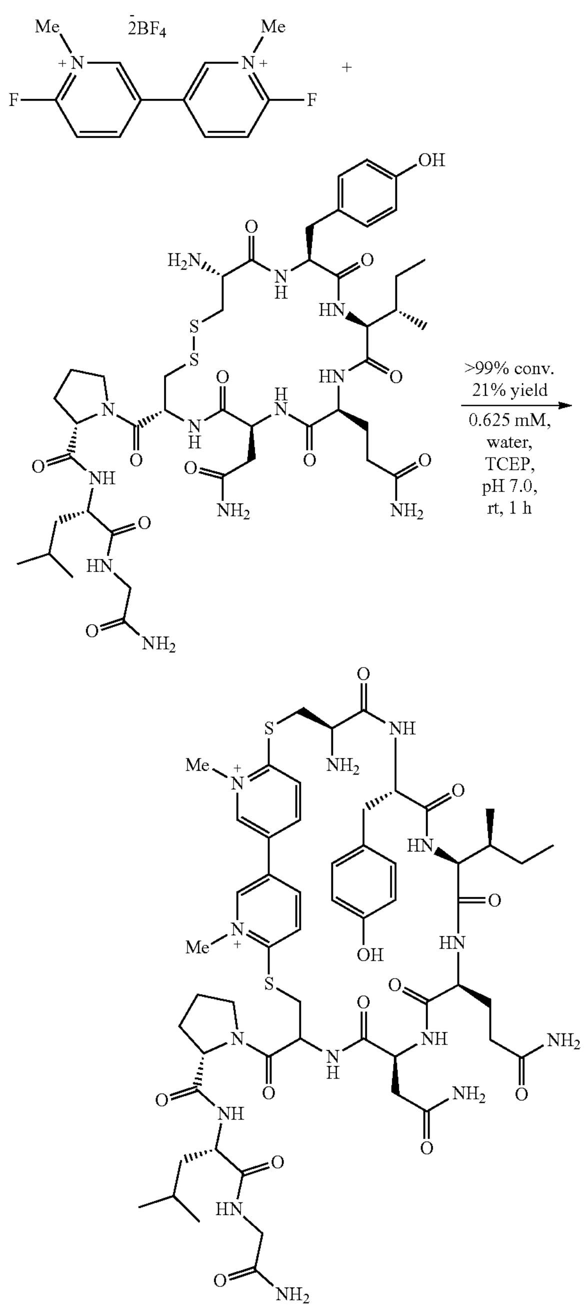

A stock solution of oxytocin (8 μL, 20 mM in water) was mixed with TCEP (4 μL, 0.5 M, pH 7) and then diluted with water (228 μL). After 5 min, an aliquot of CAP10 (16 μL, 10 mM) was added to the above mixture. The mixture was kept at room temperature for 1 h. The reaction mixture was purified by HPLC using solvent gradient 9 (Table 3, semi prep HPLC $T_R$=29.22 min) to obtain a white solid as a trifluoroacetic acid salt. Analytical HPLC using solvent gradient 11, $T_R$=13.75 min. MS (ESI+): m/z calculated for $M^{2+}$ 595.2, found 595.8.

Example 38: Labeling Cysteine Residues of Reduced Oxytocin Using CAP2

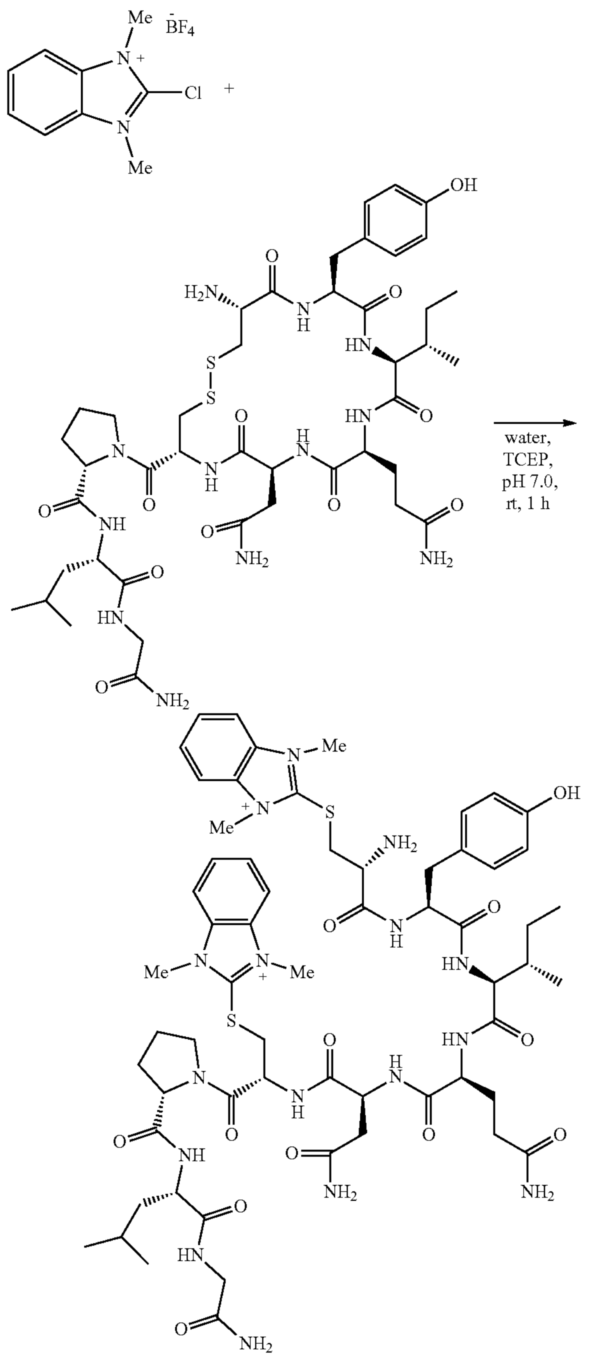

A stock solution of oxytocin (8 μL, 20 mM in water) was mixed with TCEP (4 μL, 0.5 M, pH 7) and then diluted with water (308 μL). After 5 min, an aliquot of CAP2 (80 μL, 5 mM) was added to the above mixture. The mixture was kept at room temperature for 1 h. The reaction mixture was purified by HPLC using solvent gradient 10 (Table 3, semi prep HPLC $T_R$=28.6 min) to obtain a white solid as a trifluoroacetic acid salt. Analytical HPLC using solvent gradient 11, $T_R$=13.43 min.

MS (ESI+): m/z calculated for $M^{2+}$ 649.3, found 649.7. ESI-HRMS(+) m/z calculated for $C_{61}H_{86}N_{16}O_{12}S_2^{2+}$ $M^{2+}$ 649.3021, found 649.2945. The structure of this kinetic product was also confirmed by tandem MS study.

Example 39: Labeling Cysteine Side Chains and the N-Terminus of Reduced Oxytocin Using CAP2

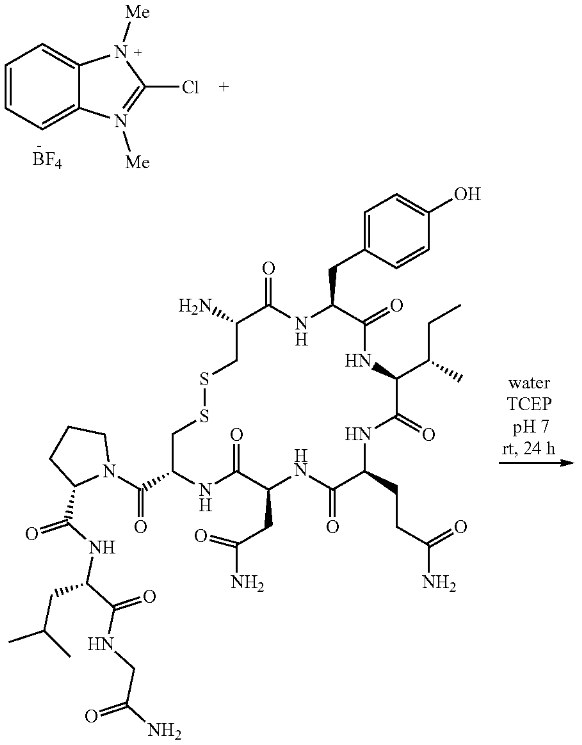

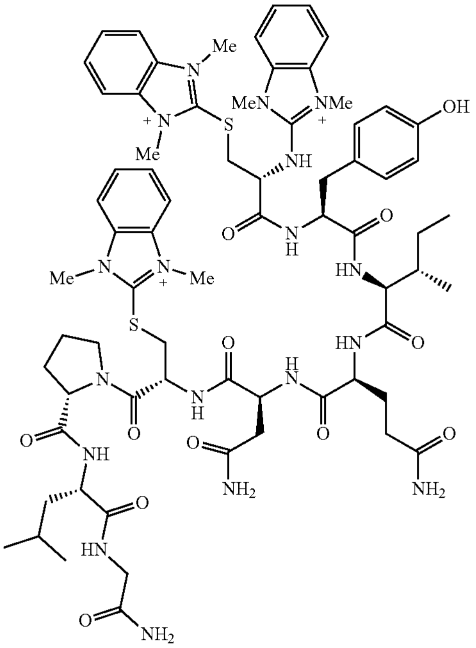

+

-continued

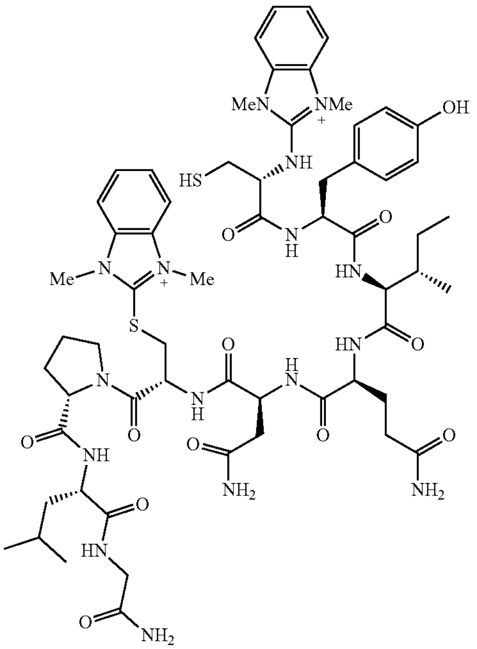

A stock solution of oxytocin (8 μL, 20 mM in water) was mixed with TCEP (4 μL, 0.5 M, pH 7) and then diluted with water (308 μL). After 5 min, an aliquot of CAP2 (80 μL, 5 mM) was added to the above mixture. The mixture was kept at room temperature for 24 h. The reaction mixture was purified by HPLC using solvent gradient 10 (Table 3). Two products were obtained as white solids. The product at $T_R$=38.4 min was functionalized by CAP2 on the N-terminus and $Cys^6$ side chain. The structure of this thermodynamic product was also confirmed by tandem MS study. This product was converted from $Cys^1$,$Cys^6$ doubly sulfur labeled oxytocin, which underwent the intramolecular CAP2 transfer from $Cys^1$ side chain to the N-terminus. Analytical HPLC using solvent gradient 11, $T_R$=15.07 min. MS (ESI+): m/z calculated for $M^{2+}$ 649.3, found 649.7. The product at $T_R$=35.6 min was functionalized by CAP2 on $Cys^1$ side chain, $Cys^6$ side chain, and the N-terminus. This product formed from the above the N-terminus, $Cys^6$ doubly labeled oxytocin, the $Cys^1$ side chain of which further reacted with CAP2 in an intermolecular fashion. Analytical HPLC using solvent gradient 11, $T_R$=14.49 min.

MS (ESI+): m/z calculated for $[M-H]^{2+}$ 721.3, found 721.8. ESI-HRMS(+) m/z calculated for $C_{61}H_{86}N_{16}O_{12}S_2^{2+}$ $M^{2+}$ 649.3021, found 649.2945. The structure of this thermodynamic product was also confirmed by tandem MS study.

Example 40: Labeling the Cysteine Side Chain and the N-Terminus of Reduced $H_2N$—YC—$CONH_2$ Using CAP2

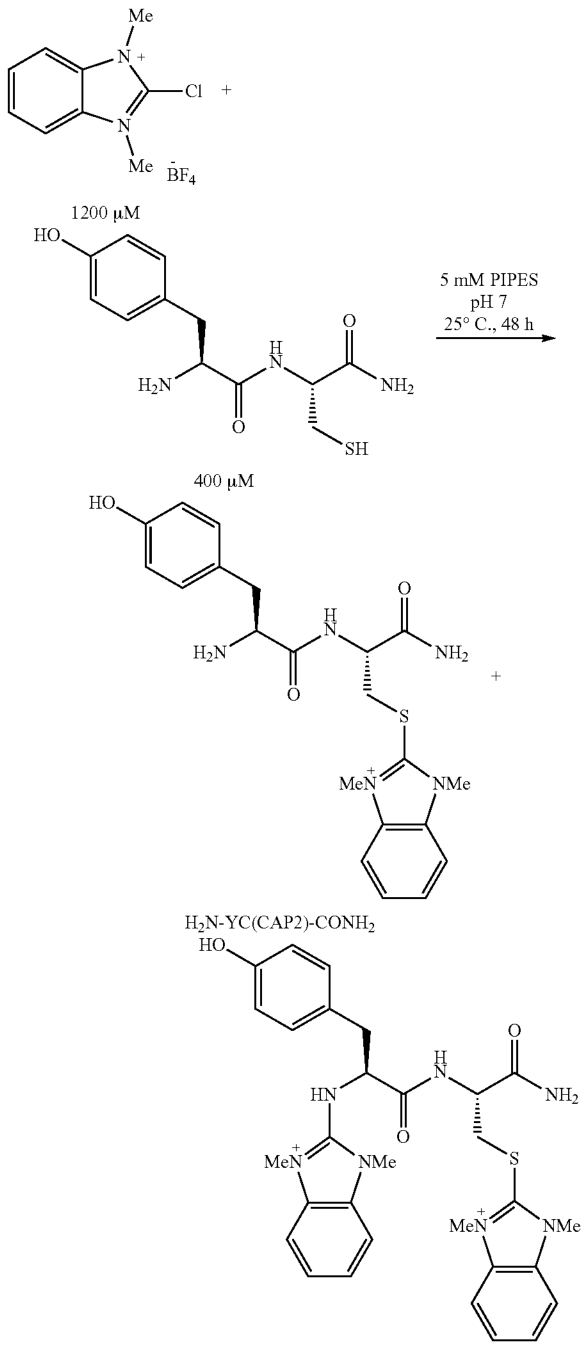

1200 μM

400 μM $H_2N$-YC(CAP2)-$CONH_2$

CAP2-HN-YC(CAP2)-$CONH_2$

A stock solution of $H_2N$—YC—$CONH_2$ (4.6 μL, 35 mM in water) was diluted with water (346 μL) and PIPES buffer (50 mM in water, pH 7, 40 μL). An aliquot of CAP2 (9.6 μL, 50 mM) was added to the above mixture. The mixture was kept at room temperature for 48 h. The reaction mixture was purified by HPLC using solvent gradient 12 (Table 3). Two products were obtained as white solids. The product at $T_R$=11.4 min was functionalized by CAP2 on the Cys side chain. MS (ESI+): m/z calculated for $[M-H]^{2+}$ 428.2, found 428.3. ESI-HRMS(+) m/z calculated for $C_{21}H_{26}N_5O_3S^+$ $M^+$ 428.1751, found 428.1717. The structure of this product was confirmed by tandem MS study. The doubly labeled product was functionalized by CAP2 on the Cys side chain and the N-terminus. Analytical HPLC using solvent gradient 11, $T_R$=14.7 min.

MS (ESI+): m/z calculated for $[M-H]^{2+}$ 286.6, found 286.8. ESI-HRMS(+) m/z calculated for $C_{30}H_{34}N_7O_3S^+$ $M^+$ 286.6256, found 286.6244. The structure of this product was confirmed by tandem MS study.

Example 41: Labeling the Cysteine Side Chain and the N-Terminus of Reduced $H_2N$—CY—$CONH_2$ Using CAP2

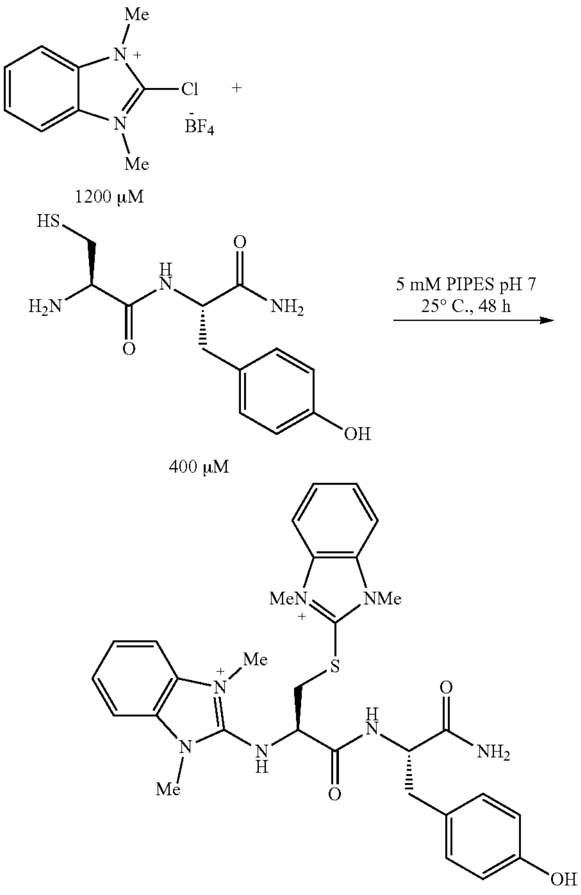

1200 μM

400 μM

CAP2-HN-C(CAP2)Y-$CONH_2$

A stock solution of $H_2N$—CY—$CONH_2$ (8.4 μL, 19 mM in water) was diluted with water (342 μL) and PIPES buffer (50 mM in water, pH 7, 40 μL). An aliquot of CAP2 (9.6 μL, 50 mM) was added to the above mixture. The mixture was kept at room temperature for 48 h. The reaction mixture was purified by HPLC using solvent gradient 12 (Table 3). The doubly labeled product was functionalized by CAP2 on the Cys side chain and the N-terminus. Analytical HPLC using solvent gradient 12, $T_R$=14.2 min.

MS (ESI+): m/z calculated for $[M-H]^{2+}$ 286.6, found 286.8. ESI-HRMS(+) m/z calculated for $C_{30}H_{34}N_7O_3S^+$ $M^+$ 286.6256, found 286.6246. The structure of this product was confirmed by tandem MS study.

Example 42: Labeling Cysteine Side Chain and Tyrosine Side Chain of N-AcYPPPC$NH_2$ Using CAP2

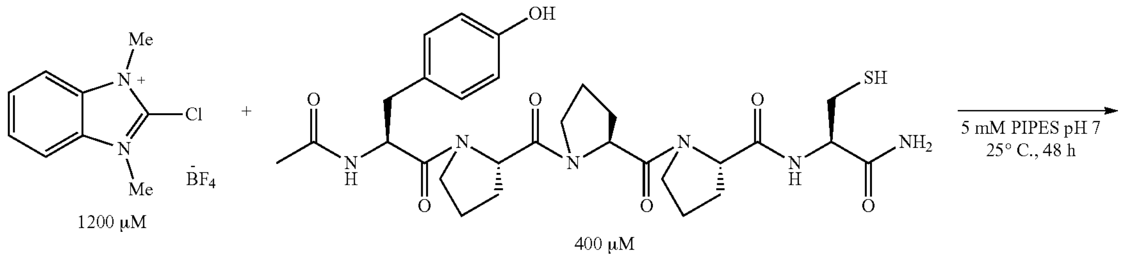

1200 μM

400 μM

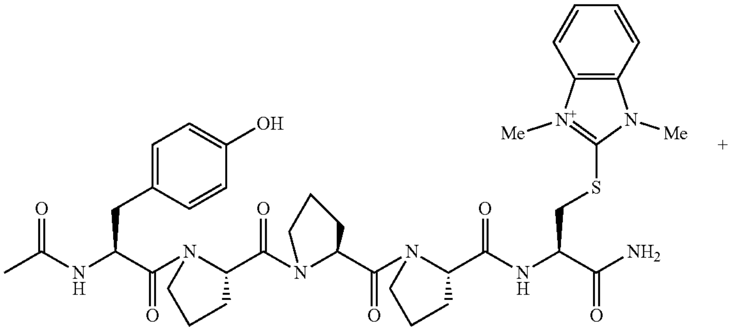

AcHN-YPPPC(CAP2)-$CONH_2$

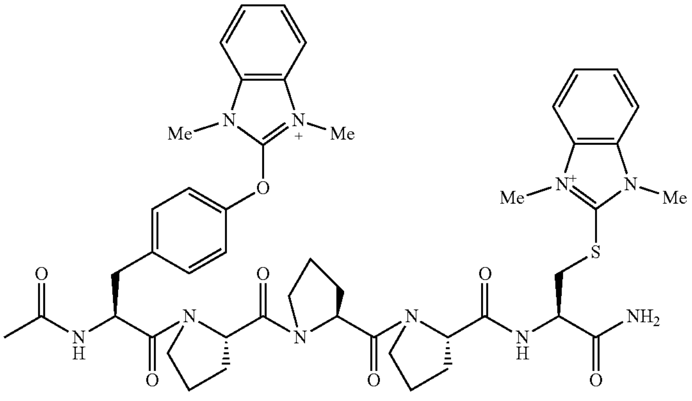

AcHN-Y(CAP2)PPPC(CAP2)-$CONH_2$

A stock solution of AcNH—YPPPC—$CONH_2$ (16 μL, 10 mM in water) was diluted with water (334 μL) and PIPES buffer (50 mM in water, pH 7, 40 μL). An aliquot of CAP2 (9.6 μL, 50 mM) was added to the above mixture. The mixture was kept at room temperature for 48 h. The reaction mixture was purified by HPLC using solvent gradient 13 (Table 3). Two products were obtained as white solids. The product at $T_R$=11.1 min was functionalized by CAP2 on the Cys side chain. MS (ESI+): m/z calculated for $[M-H]^{2+}$ 761.3, found 761.5. ESI-HRMS(+) m/z calculated for $C_{38}H_{49}N_8O_7S^+$ $M^+$ 761.3440, found 761.3394. The structure of this product was confirmed by tandem MS study. The doubly labeled product was functionalized by CAP2 on the Cys side chain and the Tyr side chain. Analytical HPLC using solvent gradient 13, $T_R$=12.4 min.

MS (ESI+): m/z calculated for $[M-H]^{2+}$ 453.2, found 453.5. ESI-HRMS(+) m/z calculated for $C_{47}H_{58}N_{10}O_7S^{2+}$ $M^{2+}$ 453.2100, found 453.2070. The structure of this product was confirmed by tandem MS study.

Example 43: Labeling GSH with CAP3

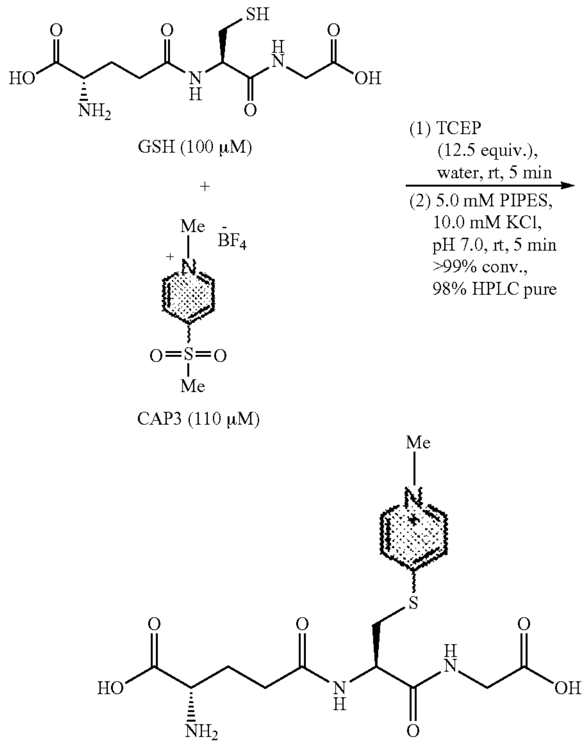

GSH (100 μM)

+

CAP3 (110 μM)

GSH-CAP3

A stock solution of GSH (1.6 μL, 50 mM in water) was mixed with water (717 μL) and PIPES buffer (80 μL, pH 7, 50 mM PIPES, 100 mM KCl). An aliquot of CAP3 (1.76 μL, 50 mM in water) was added to this mixture. The reaction was kept at room temperature for 5 min. The crude product was purified by HPLC using solvent gradient 14 (Table 3, semi prep HPLC $T_R$=13.72 min, conversion 97.6%) to obtain a white solid as a trifluoroacetic acid salt. Analytical HPLC using solvent gradient 6, $T_R$=3.36 min.

MS (ESI+): m/z calculated for $M^+$ 399.1, found 399.2. ESI-HRMS(+) m/z calculated for $C_{16}H_{23}N_4O_6S^+$ $M^+$ 399.1333, found 399.1325.

Example 44: Labeling GSH with CAP4

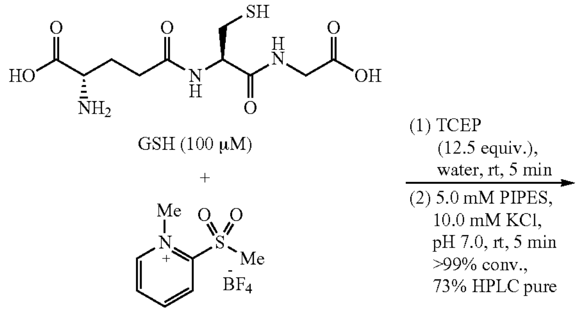

GSH (100 μM)

+

CAP4 (110 μM)

-continued

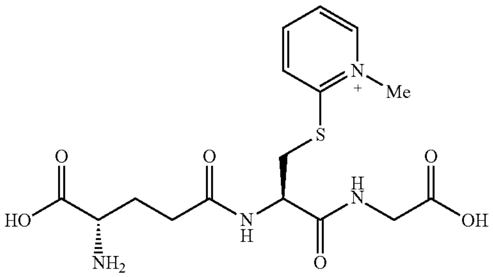

GSH-CAP4

A stock solution of GSH (1.6 μL, 50 mM in water) was mixed with water (717 μL) and PIPES buffer (80 μL, pH 7, 50 mM PIPES, 100 mM KCl). An aliquot of CAP3 (1.76 μL, 50 mM in water) was added to this mixture. The reaction was kept at room temperature for 5 min. The crude product was purified by HPLC using solvent gradient 14 (Table 3, semi prep HPLC $T_R$=13.36 min, conversion 73.1%) to obtain a white solid as a trifluoroacetic acid salt. Analytical HPLC using solvent gradient 6, $T_R$=3.35 min. ESI-HRMS (+) m/z calculated for $C_{16}H_{23}N_4O_6S^+$ $M^+$ 399.1333, found 399.1345.

Example 45: Labeling Reduced Somatostatin with CAP3

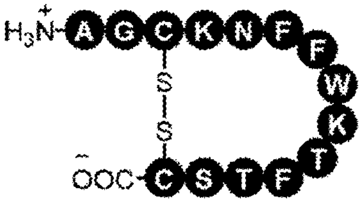

somatostatin
(100 μM)

+

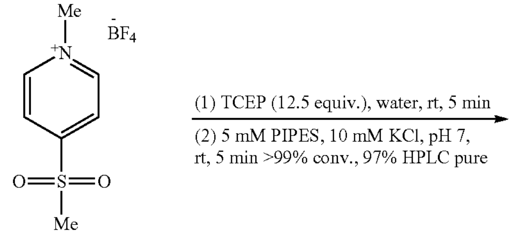

CAP3
(210 μM)

-continued

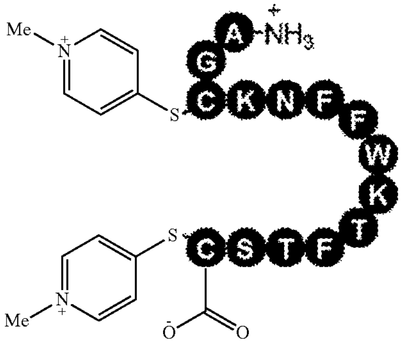

somatostatin-(CAP3)$_2$

A stock solution of somatostatin (4.59 μL, 4.36 mM in water) was mixed with TCEP (0.5 μL, 0.5 M, pH 7). After 5 min, the mixture was diluted with water (173 μL) and PIPES buffer (20 μL, pH 7, 50 mM PIPES, 100 mM KCl). An aliquot of CAP4 (0.84 μL, 50 mM in water) was added to this mixture. The reaction was kept at room temperature for 5 min. The crude product was purified by HPLC using solvent gradient 15 (Table 3, semi prep HPLC $T_R$=10.69 min, conversion 96.5%) to obtain a white solid as a trifluoroacetic acid salt. Analytical HPLC using solvent gradient 6, $T_R$=14.29 min.

MS (ESI+): m/z calculated for $[M+H]^{3+}$ 608.3, found 608.5. ESI-HRMS(+) m/z calculated for $C_{88}H_{118}N_{20}O_{19}S_2^{2+}$ $M^{2+}$ 911.4157, found 911.4141.

Example 46: Labeling Reduced Somatostatin with CAP4

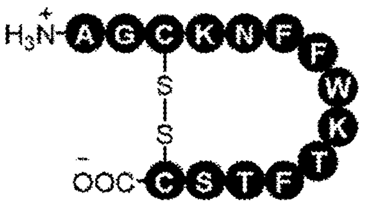

somatostatin
(100 μM)

+

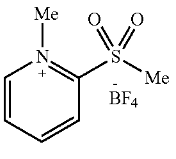

CAP4
(210 μM)

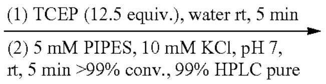

-continued

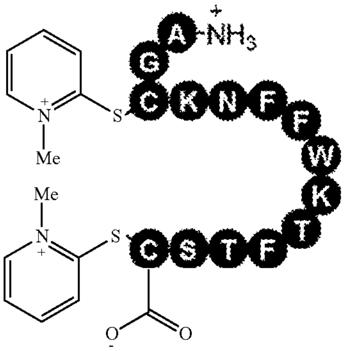

somatostatin-(CAP4)$_2$

A stock solution of somatostatin (5.62 μL, 3.56 mM in water) was mixed with TCEP (0.5 μL, 0.5 M, pH 7). After 5 min, the mixture was diluted with water (173 μL) and PIPES buffer (20 μL, pH 7, 50 mM PIPES, 100 mM KCl). An aliquot of CAP4 (0.84 μL, 50 mM in water) was added to this mixture. The reaction was kept at room temperature for 5 min. The crude product was purified by HPLC using solvent gradient 15 (Table 3, semi prep HPLC $T_R$=10.74 min, conversion 100%) to obtain a white solid as a trifluoroacetic acid salt. Analytical HPLC using solvent gradient 6, $T_R$=14.35 min.

ESI-HRMS(+) m/z calculated for $C_{88}H_{118}N_{20}O_{19}S_2^{2+}$ $M^{2+}$ 911.4157, found 911.4137.

Example 47: Labeling Reduced Oxytocin with CAP3

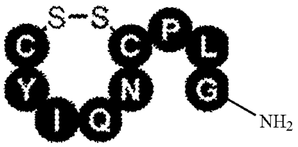

oxytocin
(100 μM)

+

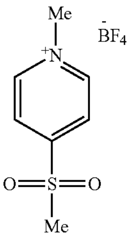

CAP3
(210 μM)

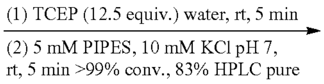

-continued

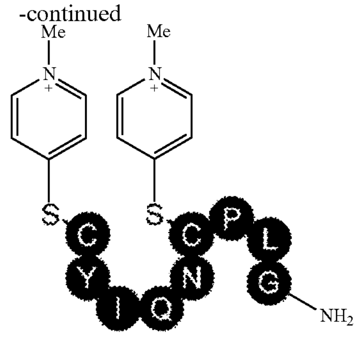

oxytocin-$(CAP3)_2$

A stock solution of oxytocin (4 µL, 20 mM in water) was mixed with TCEP (2 µL, 0.5 M, pH 7). After 5 min, the mixture was diluted with water (711 µL) and PIPES buffer (80 µL, pH 7, 50 mM PIPES, 100 mM KCl). An aliquot of CAP3 (3.36 µL, 50 mM in water) was added to this mixture. The reaction was kept at room temperature for 5 min. The crude product was purified by HPLC using solvent gradient 10 (Table 3, semi prep HPLC $T_R$=23.14 min, conversion 82.6%) to obtain a white solid as a trifluoroacetic acid salt. Analytical HPLC using solvent gradient 6, $T_R$=12.10 min.

MS (ESI+): m/z calculated for $M^{2+}$ 596.3, found 596.8. ESI-HRMS(+) m/z calculated for $C_{55}H_{80}N_{14}O_{12}S_2^{2+}$ $M^{2+}$ 596.2756, found 596.2739.

Example 48: Labeling Reduced Oxytocin with CAP4

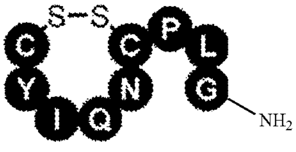

oxytocin
(100 µM)

+

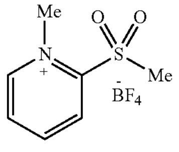

CAP4
(210 µM)

(1) TCEP (12.5 equiv.), water rt, 5 min
(2) 5.0 mM PIPES, 10.0 mM KCl, pH 7.0, rt, 5 min >99% conv., 96% HPLC pure

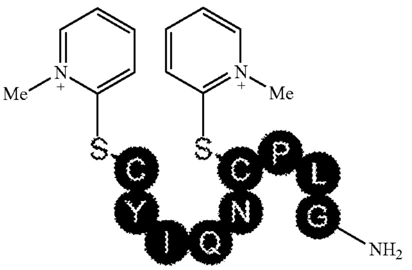

oxytocin-$(CAP4)_2$

A stock solution of oxytocin (4 µL, 20 mM in water) was mixed with TCEP (2 µL, 0.5 M, pH 7). After 5 min, the mixture was diluted with water (711 µL) and PIPES buffer (80 µL, pH 7, 50 mM PIPES, 100 mM KCl). An aliquot of CAP4 (3.36 µL, 50 mM in water) was added to this mixture. The reaction was kept at room temperature for 5 min. The crude product was purified by HPLC using solvent gradient 10 (Table 3, semi prep HPLC $T_R$=22.89 min, conversion 95.7%) to obtain white solid oxytocin-$(CAP4)_2$ as trifluoroacetic acid salt. Analytical HPLC using solvent gradient 6, $T_R$=12.15 min.

ESI-HRMS(+) m/z calculated for $C_{55}H_{80}N_{14}O_{12}S_2^{2+}$ $M^{2+}$ 596.2756, found 596.2718.

Example 49: Stapling Reduced Somatostatin with CAP5

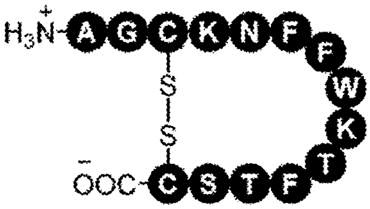

somatostatin
(200 µM)

+

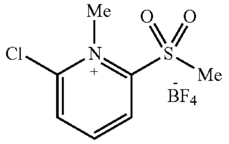

CAP5
(200 µM)

(1) TCEP (12.5 equiv.), water, rt, 5 min
(2) water, rt, 5 min 94% conv., 79% HPLC pure

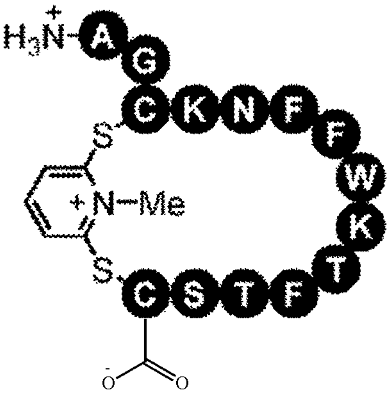

somatostatin-CAP5

A stock solution of somatostatin (11.24 µL, 3.56 mM in water) was mixed with TCEP (1 µL, 0.5 M, pH 7). After 5 min, the mixture was diluted with water (183.8 µL). An aliquot of freshly prepared CAP5 in MeCN (4 µL, 10 mM) was added to this mixture. The reaction was kept at room temperature for 5 min. The crude product was purified by HPLC using solvent gradient 16 (Table 3, semi prep HPLC $T_R$=12.63 min, conversion 78.6%) to obtain white solid somatostatin-CAP5 as a trifluoroacetic acid salt. Analytical HPLC using solvent gradient 6, $T_R$=14.68 min.

MS (ESI+): m/z calculated for $[M+H]^{2+}$ 864.9, found 865.6. ESI-HRMS(+) m/z calculated for $C_{82}H_{111}N_{19}O_{19}S_2^{2+}$ $[M+H]^{2+}$ 864.8867, found 864.8845.

Results obtained under different conditions are summarized in Table 4 below.

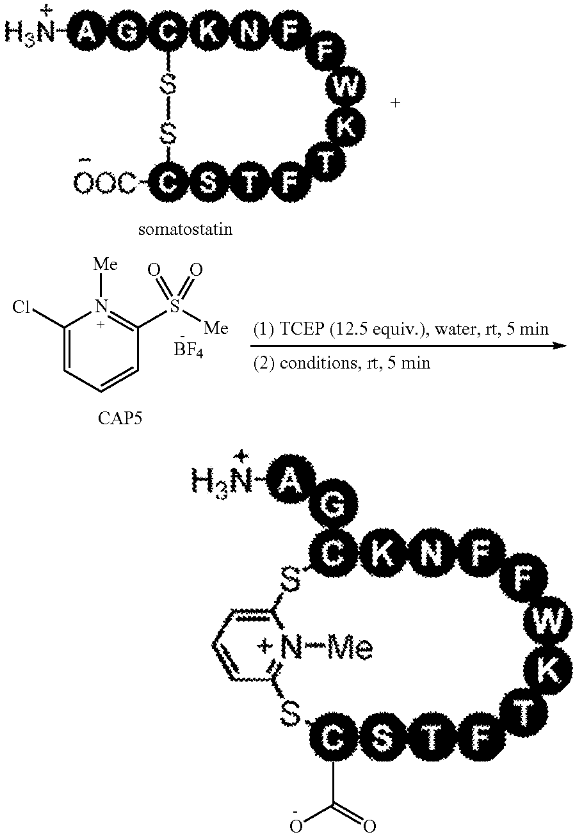

somatostatin

CAP5 somatostatin-CAP5

TABLE 4

| [Somatostatin] (μM) | [CAP5] (μM) | media | Conv. (%)[a] | Purity (%)[a] |
|---|---|---|---|---|
| 200 | 200 | Water, 25° C. | 94 | 79 |
| 100 | 100 | water, 25° C. | 93 | 82 |
| 200 | 200 | 5 mM PIPES, 10 mM KCl, pH 7, 25° C. | 96 | 84 |
| 100 | 100 | 5 mM PIPES, 10 mM KCl, pH 7, 25° C. | 96 | 87 |

[a]Based on HPLC chromatogram integration at 250 nm.

Example 50: Stapling Reduced Somatostatin with CAP6

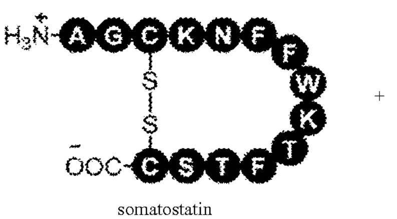

somatostatin (100 μM)

-continued

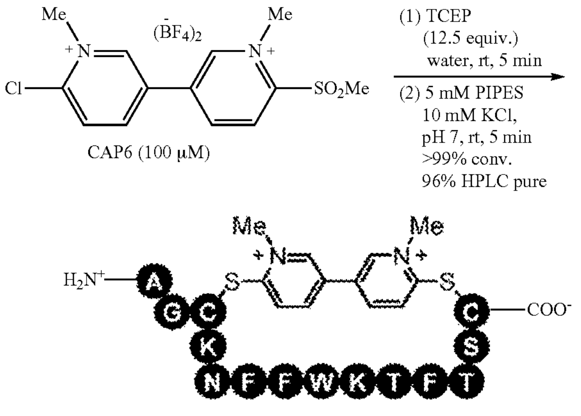

CAP6 (100 μM)

somatostatin-CAP6

A stock solution of somatostatin (5.62 μL, 3.56 mM in water) was mixed with TCEP (0.5 μL, 0.5 M, pH 7). After 5 min, the mixture was diluted with water (171.9 μL) and PIPES buffer (20 μL, pH 7, 50 mM PIPES, 100 mM KCl). An aliquot of freshly prepared CAP6 in MeCN (2 μL, 10 mM) was added to this mixture. The reaction was kept at room temperature for 5 min. The crude product was purified by HPLC using solvent gradient 16 (Table 3, semi prep HPLC $T_R$=10.35 min) to obtain a white solid as a trifluoroacetic acid salt. Analytical HPLC using solvent gradient 6, $T_R$=14.19 min.

MS (ESI+): m/z calculated for $[M+H]^{3+}$ 607.6, found 607.8. ESI-HRMS(+) m/z calculated for $C_{88}H_{117}N_{20}O_{19}S_2^{3+}$ $[M+H]^{3+}$ 607.2743, found 607.2757.

Results obtained under different conditions are summarized in Table 5 below.

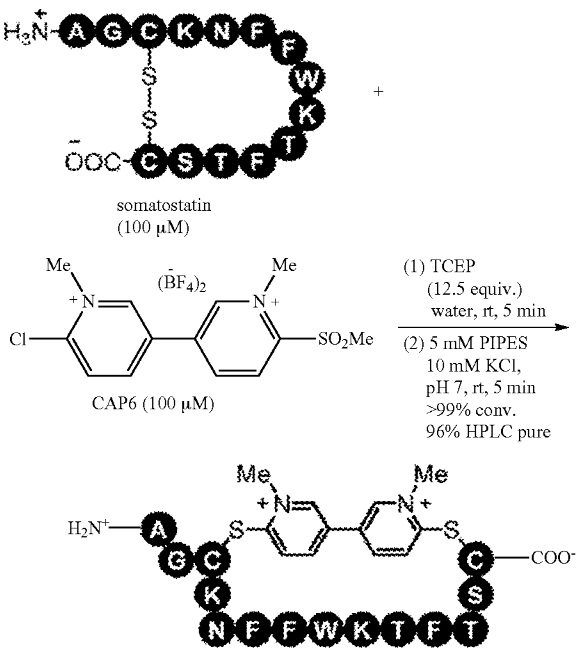

somatostatin (100 μM)

CAP6 (100 μM)

somatostatin-CAP6

TABLE 5

| [Somatostatin] (μM) | [CAP6] (μM) | media | Conv. (%)[a] | Purity (%)[a] |
|---|---|---|---|---|
| 100 | 100 | 5 mM PIPES, 10 mM KCl, pH 7, 25° C. | >99 | 96 |
| 100 | 100 | water, 25° C. | >99 | 83 |
| 50 | 50 | 5 mM PIPES, 10 mM KCl, pH 7, 25° C. | >99 | 87 |
| 25 | 25 | 5 mM PIPES, 10 mM KCl, pH 7, 25° C. | >99 | 92 |

[a]Based on HPLC chromatogram integration at 250 nm.

Example 51: Stapling Reduced Somatostatin with CAP7

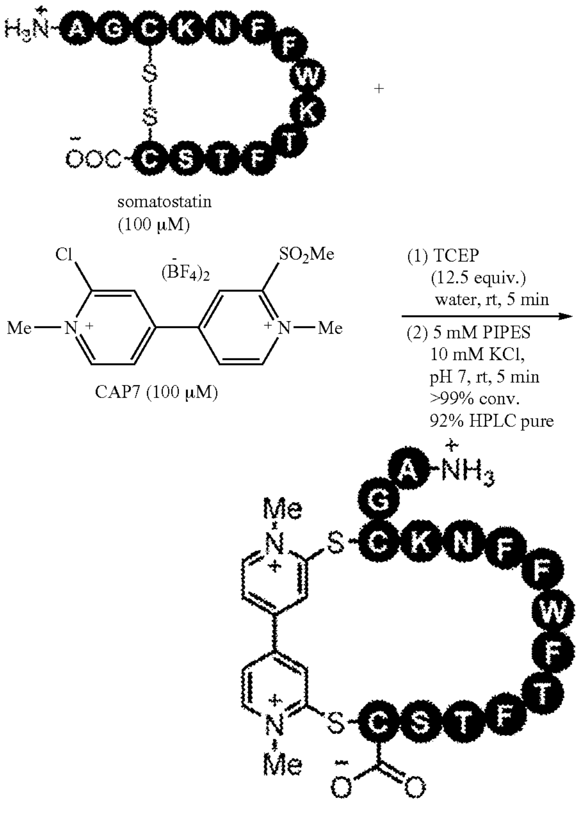

somatostatin (100 μM)

CAP7 (100 μM)

somatostatin-CAP7

A stock solution of somatostatin (5.62 μL, 3.56 mM in water) was mixed with TCEP (0.5 μL, 0.5 M, pH 7). After 5 min, the mixture was diluted with water (171.9 μL) and PIPES buffer (20 μL, pH 7, 50 mM PIPES, 100 mM KCl). An aliquot of freshly prepared CAP7 in MeCN (2 μL, 10 mM) was added to this mixture. The reaction was kept at room temperature for 5 min. The crude product was purified by HPLC using solvent gradient 16 (Table 3, semi prep HPLC $T_R$=11 min, conversion 91.5%) to obtain white solid somatostatin-CAP7 as a trifluoroacetic acid salt. Analytical HPLC using solvent gradient 6, $T_R$=14.55 min.

ESI-HRMS(+) m/z calculated for $C_{88}H_{117}N_{20}O_{19}S_2^{3+}$ $[M+H]^{3+}$ 607.2743, found 607.2780.

Example 52: Stapling Reduced Somatostatin with CAP8

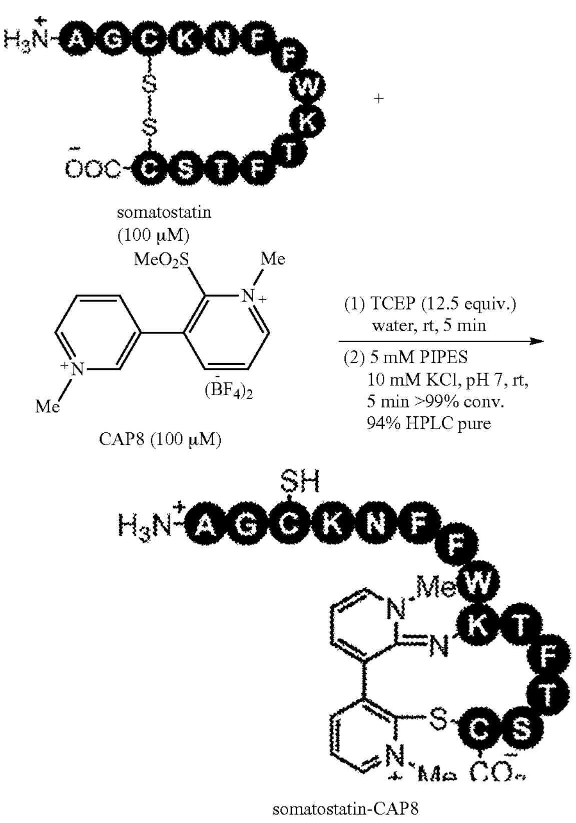

somatostatin (100 μM)

CAP8 (100 μM)

somatostatin-CAP8

A stock solution of somatostatin (5.62 μL, 3.56 mM in water) was mixed with TCEP (0.5 μL, 0.5 M, pH 7). After 5 min, the mixture was diluted with water (171.9 μL) and PIPES buffer (20 μL, pH 7, 50 mM PIPES, 100 mM KCl). An aliquot of freshly prepared CAP8 in MeCN (2 μL, 10 mM) was added to this mixture. The reaction was kept at room temperature for 5 min. The crude product was purified by HPLC using solvent gradient 16 (Table 3, semi prep HPLC $T_R$=11.1 min, conversion 93.6%) to obtain white solid somatostatin-CAP8 as a trifluoroacetic acid salt. Analytical HPLC using solvent gradient 6, $T_R$=14.66 min. ESI-HRMS(+) m/z calculated for $C_{88}H_{117}N_{20}O_{19}S_2^{3+}$ $[M+H]^{3+}$ 607.2743, found 607.2742.

Example 53: Stapling Reduced Oxytocin with CAP5

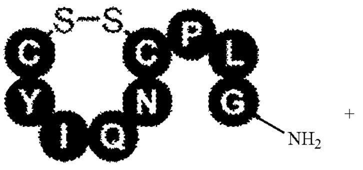

oxytocin (100 μM)

-continued

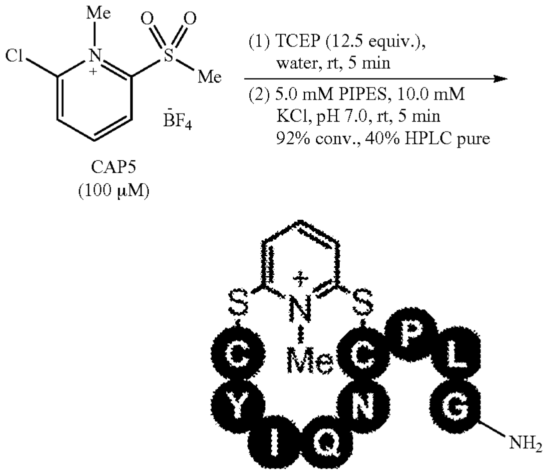

CAP5 (100 μM)

oxytocin-CAP5

A stock solution of oxytocin (4 μL, 20 mM in water) was mixed with TCEP (2 μL, 0.5 M, pH 7). After 5 min, the mixture was diluted with water (706 μL) and PIPES buffer (80 μL, pH 7, 50 mM PIPES, 100 mM KCl). An aliquot of freshly prepared CAP5 in MeCN (8 μL, 10 mM) was added to this mixture. The reaction was kept at room temperature for 5 min. The crude product was purified by HPLC using solvent gradient 10 (Table 3, semi prep HPLC $T_R$=26.26 min, conversion 43.6%) to obtain white solid oxytocin-CAP5 as a trifluoroacetic acid salt. Analytical HPLC using solvent gradient 6, $T_R$=12.91 min.

MS (ESI+): m/z calculated for $[M+H]^{2+}$ 1098.5, found 1098.7. ESI-HRMS(+) m/z calculated for $C_{49}H_{72}N_{13}O_{12}S_2^+$ $[M+H]^+$ 1098.4860, found 1098.4872.

Example 54: Stapling Reduced Oxytocin with CAP6

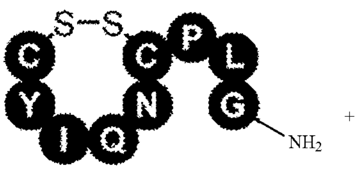

+ oxytocin (100 μM)

-continued

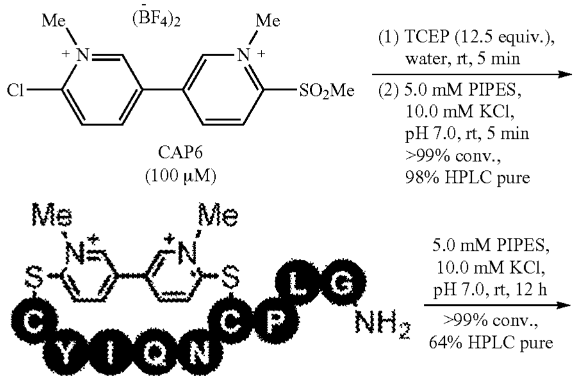

CAP6 (100 μM)

oxytocin-CAP6

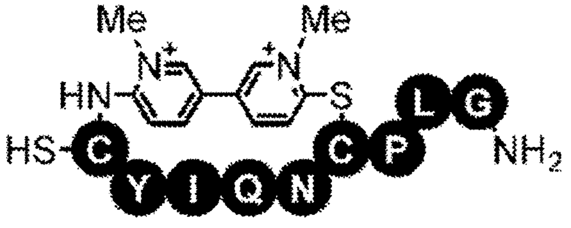

oxytocin-CAP6′

A stock solution of oxytocin (4 μL, 20 mM in water) was mixed with TCEP (2 μL, 0.5 M, pH 7). After 5 min, the mixture was diluted with water (706 μL) and PIPES buffer (80 μL, pH 7, 50 mM PIPES, 100 mM KCl). An aliquot of freshly prepared CAP6 in MeCN (8 μL, 10 mM) was added to this mixture. The reaction was kept at room temperature for 5 min. The crude product was purified by HPLC using solvent gradient 10 (Table 3, semi prep HPLC $T_R$=22.98 min, conversion 97.6%) to obtain white solid oxytocin-CAP6 as a trifluoroacetic acid salt. Analytical HPLC using solvent gradient 6, $T_R$=12.09 min.

MS (ESI+): m/z calculated for $M^{2+}$ 595.2, found 595.8. ESI-HRMS(+) m/z calculated for $C_{55}H_{78}N_{14}O_{12}S_2^{2+}$ $M^{2+}$ 595.2677, found 595.2674. The obtained cysteine-arylated product oxytocin-CAP6 isomerized through intramolecular S→N-terminus transfer after storing in pH 7 PIPES buffer at room temperature for 12 h. (Table 3, solvent gradient 3, semi prep HPLC $T_R$=30.25 min, conversion 64%) to obtain white solid oxytocin-CAP6 isomer as a trifluoroacetic acid salt. Analytical HPLC using solvent gradient 6, $T_R$=13.69 min.

MS (ESI+): m/z calculated for $M^{2+}$ 595.2, found 595.8. ESI-HRMS(+) m/z calculated for $C_{55}H_{78}N_{14}O_{12}S_2^{2+}$ $M^{2+}$ 595.2677, found 595.2686.

Example 55: One-Pot Two-Step Labeling of GSH with CAP9 and Phenol

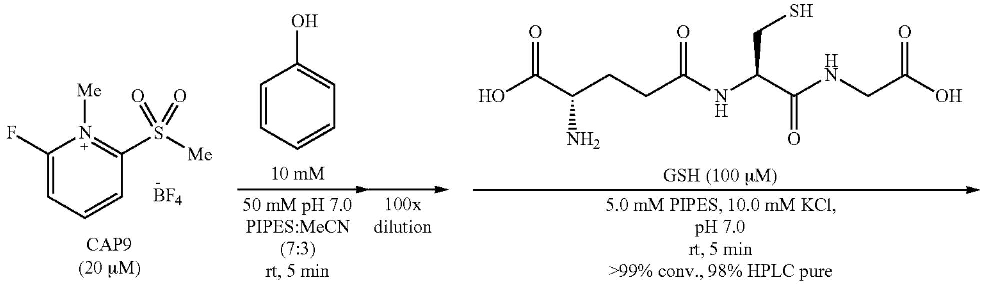

CAP9 (20 μM)

-continued

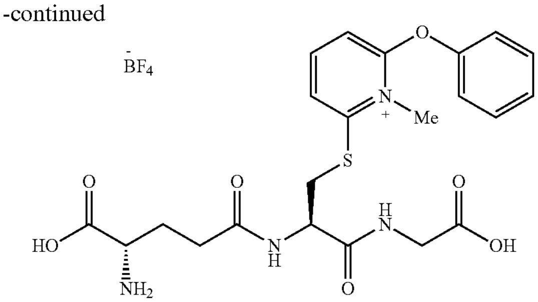

To a mixture of PIPES buffer (14 μL, pH 7) and PhOH (2 μL, 100 mM in MeCN), an aliquot of CAP9 (4 μL, 100 mM in MeCN) was added. The reaction was kept at room temperature for 5 min. An aliquot of this solution (4 μL) was added to a mixture of GSH (4 μL, 10 mM in water), PIPES buffer (40 μL, pH 7, 50 mM PIPES, 100 mM KCl), and water (352 μL). This reaction was kept at room temperature for 5 min. The crude product was purified by HPLC using solvent gradient 17 (Table 3, semi prep HPLC $T_R$=13.67 min) to obtain a white solid as a trifluoroacetic acid salt.

MS (ESI+): m/z calculated for $M^+$ 491.2, found 491.2. ESI-HRMS(+) m/z calculated for $C_{22}H_{27}N_4O_7S^+$ $M^+$ 491.1595, found 491.1586.

Example 56: Labeling Papain with CAP1 in PIPES Buffer and the Subsequent Kinetic Study

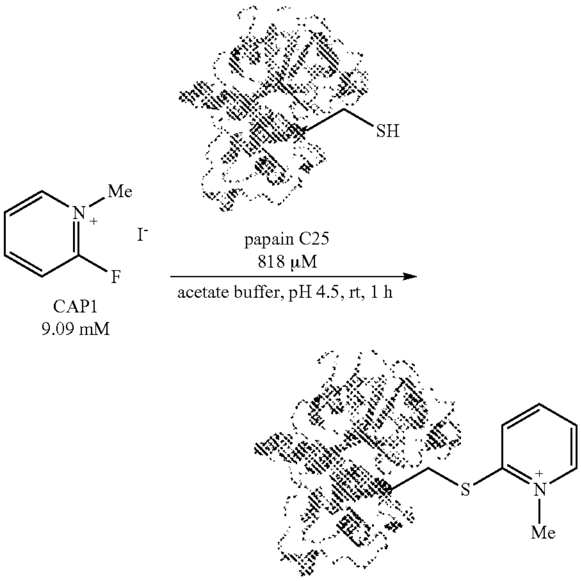

CAP1
9.09 mM papain-CAP1

An aliquot of papain (9 μL, 1 mM suspension in 50 mM sodium acetate, pH 4.5, containing 0.01% thymol) was mixed with 50 mM CAP1 (2 μL, in water). This solution was kept at room temperature for 40 min. A portion of this solution (9 μL) was added to a cuvette containing Nu-benzoyl-DL-arginine 4-nitroanilide hydrochloride (BAPNA, 3 mM in DMSO, 491 μL) and 20 mM PIPES buffer (2500 μL, pH 6.27) with 2 mM EDTA and 300 mM NaCl. The progress of BAPNA hydrolysis was monitored at 400 nm by UV-Vis spectroscopy with stirring at 25° C.

The control experiment was conducted under similar conditions. An aliquot of papain (9 μL, 1 mM suspension in 50 mM sodium acetate, pH 4.5, containing 0.01% thymol) was mixed with a 20 mM PIPES buffer (2 μL, pH 6.27) containing 2 mM EDTA and 300 mM NaCl. This solution was kept at room temperature for 40 min. A portion of this solution (9 μL) was added to a cuvette containing BAPNA (3 mM in DMSO, 491 μL) and 20 mM PIPES buffer (2500 μL, pH 6.27) with 2 mM EDTA and 300 mM NaCl. The progress of BAPNA hydrolysis was monitored at 400 nm by UV-Vis spectroscopy with stirring at 25° C., which revealed inhibited enzymatic activity of papain, in turn, suggesting the arylation of cysteine at the active site.

Example 57: Labeling BSA with CAP1 in PIPES Buffer

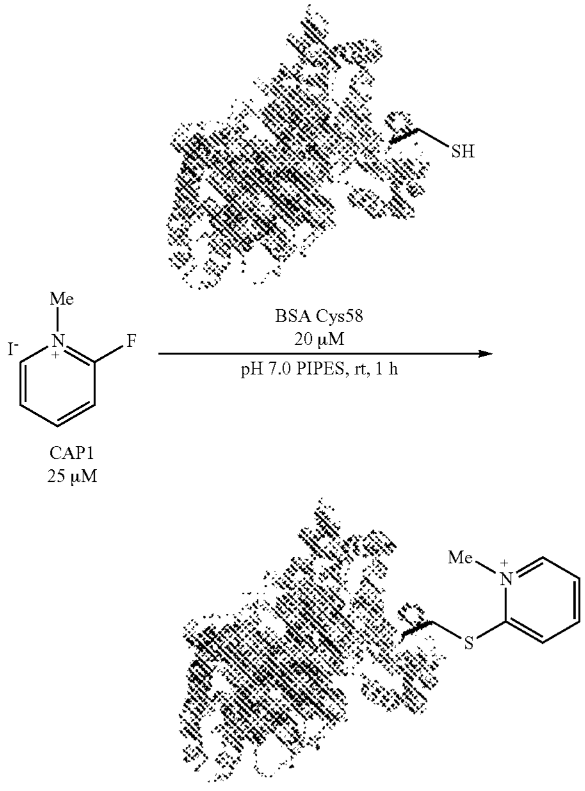

CAP1
25 μM

BSA-CAP1

The stock solution of bovine serum albumin (BSA) in 0.9% saline solution with 0.05% sodium azide (2 mg/mL, 30 μM, 20 μL) was mixed with pH 7 PIPES (8.5 μL). An aliquot of CAP1 in water (0.5 mM, 1.5 μL, 1.25 equiv.) was added to this mixture. The reaction was kept at room temperature for 1 h to generate a solution of BSA-CAP1.

This sample was digested using Trypsin Singles, Proteomic Grade Kit (Sigma-Aldrich, Catalog Number: T7575) according to the manufacturer's directions. Briefly, trypsin solubilizing reagent (1 µL) was added to a trypsin singles vial. For native protein digestion, BSA (2 mg/mL, 30 µM, 20 µL) and tris buffer (pH 10.4, 20 µL) were combined in a microcentrifuge tube and transferred to the trypsin singles vial. For arylated protein digestion, the sample from the previous step was added to the respective trypsin singles vial. In both cases, trypsin reaction buffer (49 µL, 40 mM $NH_4HCO_3$ aq. and 9% v/v $CH_3CN$) was transferred to each vial. The digestion mixture was vortexed and centrifuged before a 5 h incubation at 37° C. The samples were acidified with 10% v/v $CF_3CO_2H$ aq. (1.6 µL). The samples were diluted 1:10 with $CH_3CN$ and analyzed by MALDI-TOF spectrometry with α-cyano-4-hydroxycinnamic acid (CHCA) matrix. Mass data were compared to mass lists generated from Expasy PeptideMass database (ID: ALBU_BOV) and indicated the formation of desired BSA-CAP1.

Example 58: Labeling GFP V150C with CAP1-CCH in PIPES and Phosphate Buffer

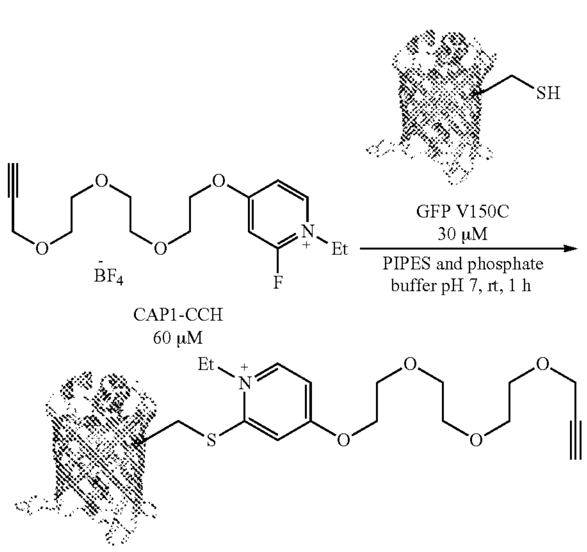

CAP1-CCH
60 µM

GFP V150C-CAP1-CCH

The stock solution of GFP V150C (10 µL, 60 µM in 50 mM phosphate buffer) was mixed with pH 7 PIPES (8.8 µL). An aliquot of CAP1-CCH in water (1 mM, 1.2 µL, 2 equiv.) was added to this mixture. The reaction was kept at room temperature for 1 h. The resulting mixture was analyzed with MALDI-MS using super-DHB matrix (Supelco). MS (MALDI+): m/z calculated for M+ 30120, found 30126.

Example 59

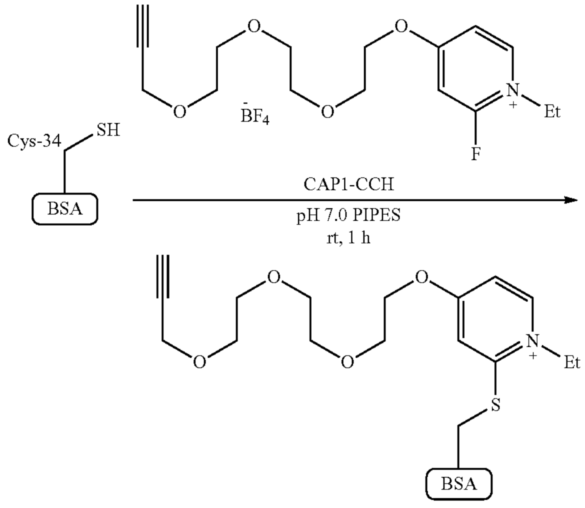

BSA-CAP1-CCH

A stock solution of BSA (2 mg/L, 30 µM, in 0.9% NaCl saline with $NaN_3$ inhibitor, 10 µL) was diluted with PIPES buffer (50 mM, pH 7, 8.8 µL). An aliquot of CAP1-CCH (1.2 µL, 1 mM in water, 4 equiv.) was added to the above mixture. The mixture was kept at room temperature for 1 h before MALDI analysis using sinapinic acid matrix.

MS (MALDI+): m/z calculated for $[BSA\text{-}CAP1\text{-}CCH]^+$ 66755, found 66755; m/z calculated for $[BSA\text{-}CAP1\text{-}CCH]^{2+}$ 33378, found 33378.

Example 60: Labeling Bovine Serum Albumin (BSA) with CAP1-CCH and 7-Azido-Methylcoumarin in PIPES Buffer Step One

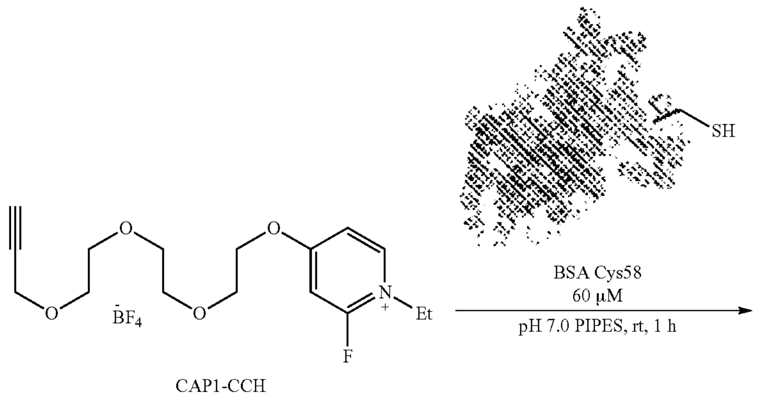

CAP1-CCH
120 µM

-continued

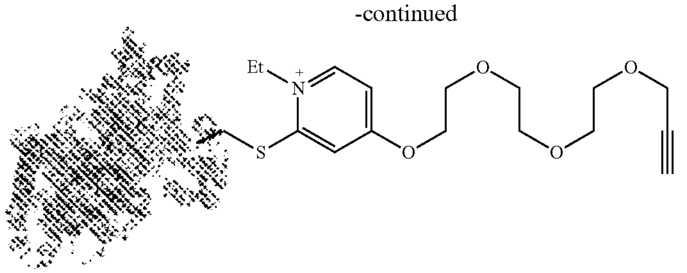

BSA-CAP1-CCH

Step Two

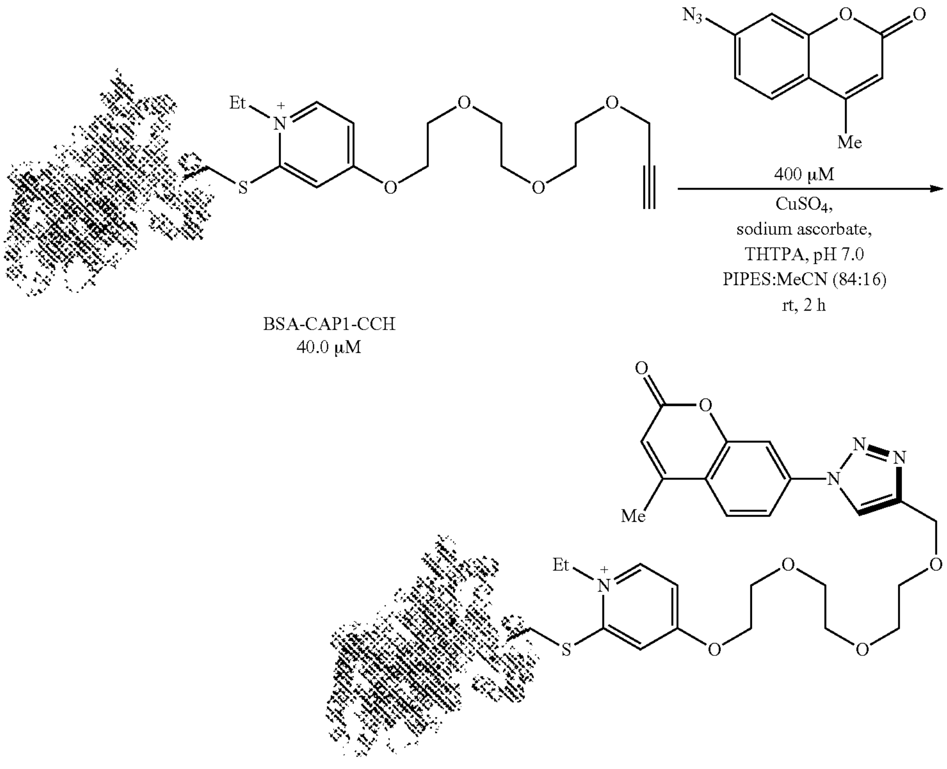

BSA-CAP1-triazole-coumarin

A stock solution of bovine serum albumin (BSA) was freshly prepared by dissolving lyophilized material (Fisher Scientific, catalog number BP671) in water. This solution (11.2 mg/mL, 169 μM, 3.56 μL) was mixed with pH 7 PIPES (5.24 μL). An aliquot of CAP1-CCH in water (1 mM, 1.2 μL, 2 equiv.) was added to this mixture. The reaction was kept at room temperature for 1 h to generate BSA-CAP1-CCH solution (60 μM). In a separate microcentrifuge tube, the catalyst solution was prepared by mixing $CuSO_4$ (80 mM, 1.25 μL, in water) with tris(3-hydroxypropyltriazolylmethyl)amine (THTPA, 50 mM, 10 μL, in water) and sodium ascorbate (100 mM, 6 μL, in water). After 5 min, this solution was diluted with pH 8 PBS (22.8 μL). Sodium ascorbate aq. (10 mM, 0.06 μL) was added to BSA-CAP1-CCH solution (60 μM, 6.7 μL), followed by the addition of the catalyst solution (1.6 μL), 7-azido-methylcoumarin in MeCN (2.5 mM, 1.6 μL, 10 equiv. relative to BSA-CAP1-CCH), and water (0.04 μL). The reaction was kept at room temperature for 2 h in the dark.

This sample was digested using Trypsin Singles, Proteomic Grade Kit (Sigma-Aldrich, Catalog Number: T7575) according to the manufacturer's directions. Briefly, trypsin solubilizing reagent (1 μL) was added to a trypsin singles vial. For native protein digestion, BSA (11.2 mg/mL, 169 μM, 3.56 μL), PIPES (pH 7, 5.24 μL), and water (1.2 μL) were combined in a microcentrifuge tube. An aliquot of this solution (6.7 μL) was mixed with water (3.3 μL) and transferred to the trypsin singles vial. This mixture was further diluted with water (20.1 μL). For arylated proteins, the sample from the previous step was mixed with water (20.1 μL) added to the respective trypsin singles vial. In both cases, trypsin reaction buffer (30.2 μL, 40 mM $NH_4HCO_3$ aq. and 9% v/v MeCN) was transferred to each vial. The digestion mixture was vortexed and centrifuged before a 5 h incubation at 37° C. The samples were diluted 1:10 with MeCN containing 0.1 v % $CF_3CO_2H$ and analyzed by MALDI-TOF spectrometry with α-cyano-4-hydroxycinnamic acid (CHCA) matrix. Mass data were compared to mass lists generated from Expasy PeptideMass database (ID: ALBU_BOV). A similar result was obtained using BSA:CAP1-CCH:7-azido-methylcoumarin:$CuSO_4$ in 1:10:50:10 ratio.

Example 61: One-Pot Two-Step Labeling of GFP V150C with CAP1-F and Tetramethylrhodamine Phenol Derivative
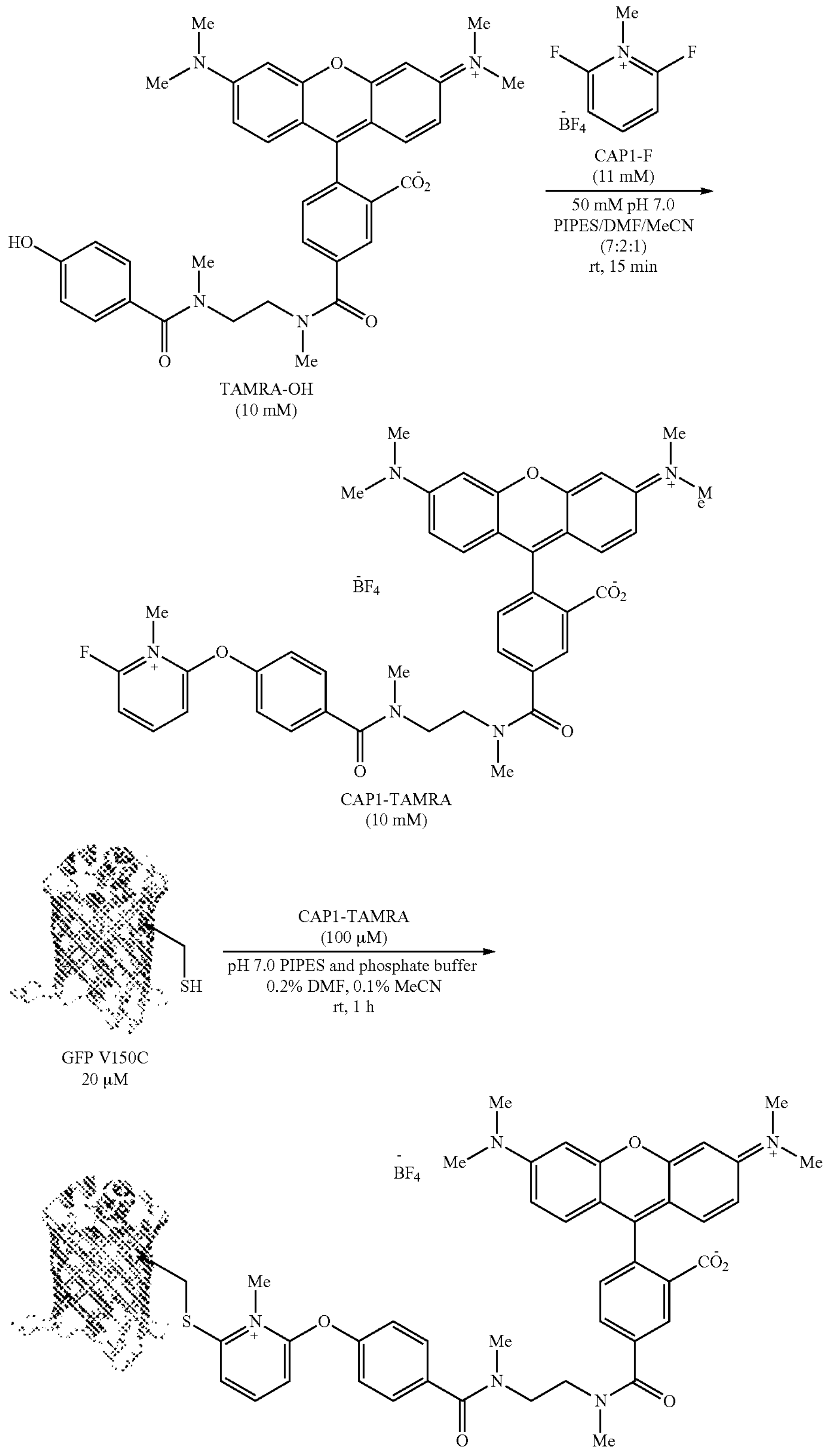
GFP-V150C-CAP9-TAMRA An aliquot of CAP1-F (2.2 μL, 100 mM in MeCN) was added to a mixture of PIPES buffer (13.5 μL, pH 7) and tetramethylrhodamine phenol derivative (4.26 μL, 47 mM in DMF). The reaction was kept at room temperature for 15 min. An aliquot of this solution (4 μL, 10 mM) was diluted with water (16 μL) to give a 2 mM CAP1-TAMRA solution. An aliquot of the CAP1-TAMRA solution (1 μL, 2 mM, 2 equiv.) was mixed with GFP V150C (16.6 μL, 60 μM in 50 mM phosphate buffer) in pH 7 PIPES (2.4 μL). The reaction mixture was analyzed by gel electrophoresis. Protein samples were loaded in 2× Laemmli sample buffer (Bio-Rad 1610737) and resolved by SDS-PAGE (Bio-Rad, Any kD™ mini-PROTEAN® TGX Stain-Free™ protein gels, 4568126). The gel was visualized with an Azure Sapphire Biomolecular Imager for GFP (excitation 488 nm; emission 518 nm) and TAMRA (excitation 520 nm; emission 565 nm), which confirmed the formation of the desired GFP-V150C-CAP1-TAMRA conjugate. Analogous results were obtained with 4 equiv. of CAP1-TAMRA under similar reaction conditions.

Example 62: Labeling BSA with CAP3 in PIPES Buffer

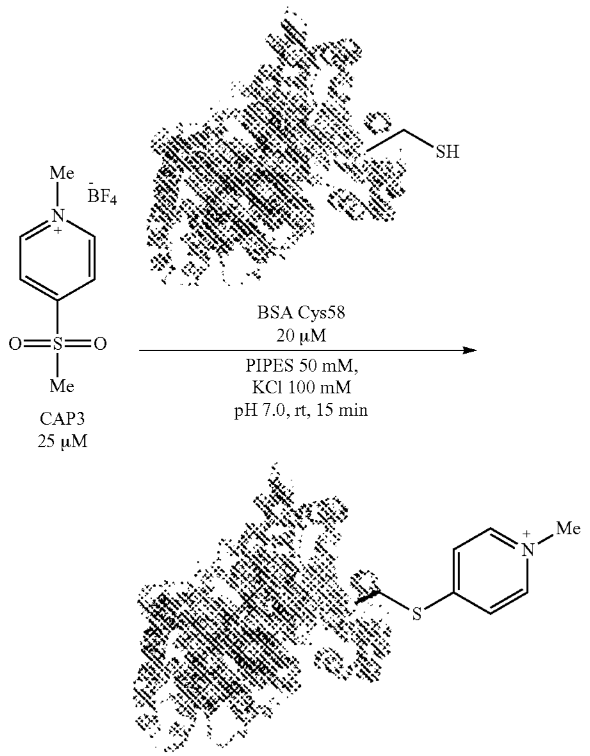

CAP3
25 μM

BSA-CAP3

The stock solution of bovine serum albumin (BSA) in water (11.2 mg/mL, 169 μM, 3.56 μL) was mixed with PIPES buffer (24.94 μL, pH 7, 50 mM PIPES, 100 mM KCl). An aliquot of CAP3 in water (0.5 mM, 1.5 μL, 1.25 equiv.) was added to this mixture. The reaction was kept at room temperature for 15 min to generate a solution of BSA-CAP3. This sample was digested using Trypsin Singles, Proteomic Grade Kit (Sigma-Aldrich, Catalog Number: T7575) according to the manufacturer's directions. Briefly, trypsin solubilizing reagent (1 μL) was added to a trypsin singles vial. For native protein digestion, BSA (2 mg/mL, 30 μM, 20 μL) and tris buffer (pH 10.4, 20 μL) were combined in a microcentrifuge tube and transferred to the trypsin singles vial. For arylated protein digestion, the sample from the previous step was added to the respective trypsin singles vial. In both cases, trypsin reaction buffer (49 μL, 40 mM $NH_4HCO_3$ aq. and 9% v/v $CH_3CN$) was transferred to each vial. The digestion mixture was vortexed and centrifuged before a 5 h incubation at 37° C. The samples were acidified with 10% v/v $CF_3CO_2H$ aq. (1.6 μL). The samples were diluted 1:10 with $CH_3CN$ and analyzed by MALDI-TOF spectrometry with α-cyano-4-hydroxycinnamic acid (CHCA) matrix. Mass data were compared to mass lists generated from Expasy PeptideMass database (ID: ALBU_BOV) and indicated the formation of desired BSA-CAP3.

Example 63: Labeling BSA with CAP4 in PIPES Buffer

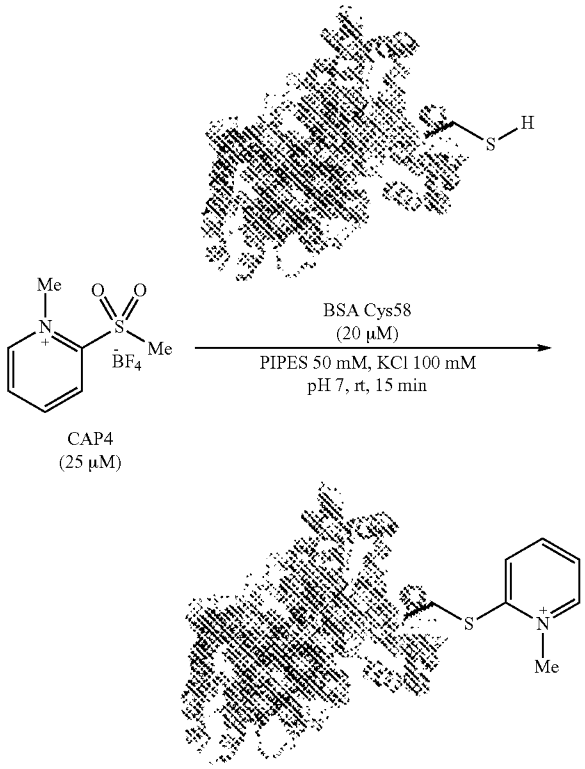

CAP4
(25 μM)

BSA-CAP4

The stock solution of bovine serum albumin (BSA) in water (11.2 mg/mL, 169 μM, 3.56 μL) was mixed with PIPES buffer (24.94 μL, pH 7, 50 mM PIPES, 100 mM KCl). An aliquot of CAP4 in water (0.5 mM, 1.5 μL, 1.25 equiv.) was added to this mixture. The reaction was kept at room temperature for 15 min to generate a solution of BSA-CAP4. This sample was digested using Trypsin Singles, Proteomic Grade Kit (Sigma-Aldrich, Catalog Number: T7575) according to the manufacturer's directions. Briefly, trypsin solubilizing reagent (1 μL) was added to a trypsin singles vial. For native protein digestion, BSA (2 mg/mL, 30 μM, 20 μL) and tris buffer (pH 10.4, 20 μL) were combined in a microcentrifuge tube and transferred to the trypsin singles vial. For arylated protein digestion, the sample from the previous step was added to the respective trypsin singles vial. In both cases, trypsin reaction buffer (49 μL, 40 mM $NH_4HCO_3$ aq. and 9% v/v $CH_3CN$) was transferred to each vial. The digestion mixture was vortexed and centrifuged before a 5 h incubation at 37° C. The samples were acidified with 10% v/v $CF_3CO_2H$ aq. (1.6 μL). The samples were diluted 1:10 with $CH_3CN$ and analyzed by MALDI-TOF spectrometry with α-cyano-4-hydroxycinnamic acid (CHCA) matrix. Mass data were compared to mass lists generated from Expasy PeptideMass database (ID: ALBU_BOV) and indicated the formation of desired BSA-CAP4.

Example 64: One-Pot Two-Step Labeling of BSA with CAP9 and Tetramethylrhodamine Phenol Derivative

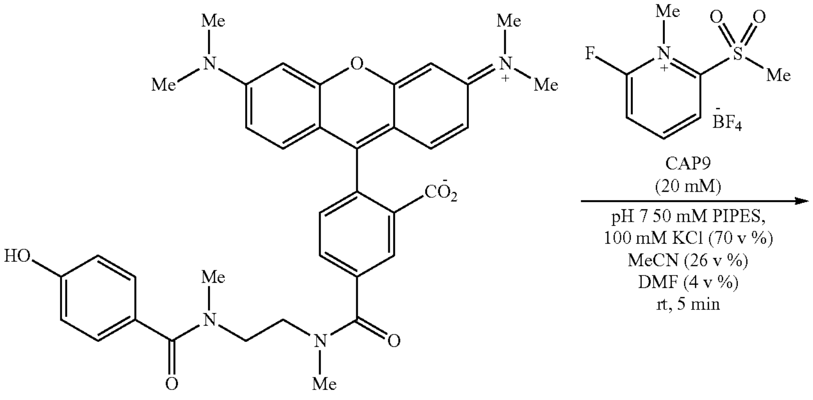

TAMRA-OH
(10 mM)

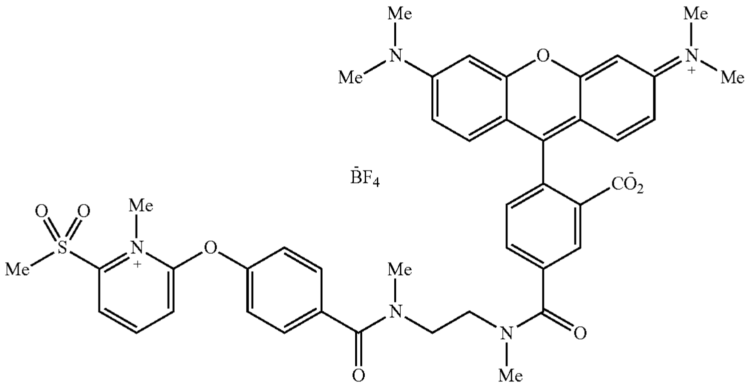

CAP9-TAMRA
(10 mM)

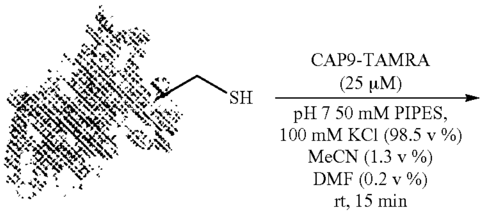

-continued

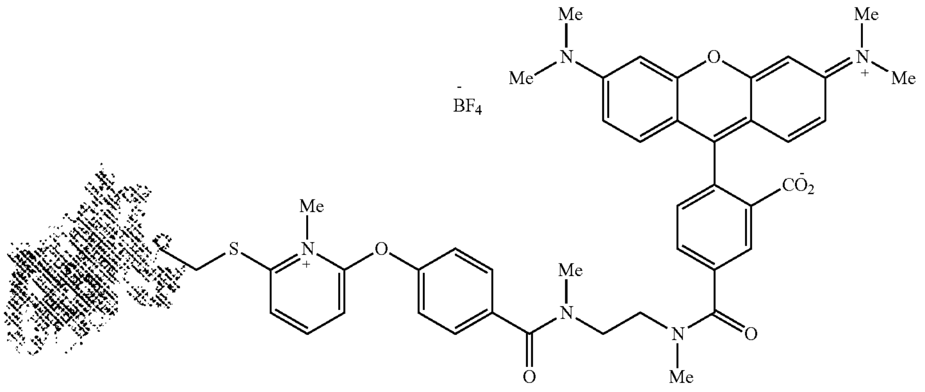

BSA-CAP9-TAMRA

An aliquot of freshly prepared CAP9 (2 μL, 100 mM in MeCN) was added to a mixture of PIPES buffer (7 μL, pH 7, 50 mM PIPES, 100 mM KCl) and tetramethyl rhodamine phenol derivative (1 μL, 100 mM in MeCN/DMF, 63:37 v:v). The reaction was kept at room temperature for 5 min. An aliquot of this solution (1 μL, 100 mM) was diluted with water (19 μL) to give a 10 mM CAP9-TAMRA solution. An aliquot of the above CAP9-TAMRA solution (1.5 μL, 0.5 mM, 1.25 equiv.) was mixed with BSA (3.56 μL, 169 μM in water) in PIPES buffer (24.94 μL, pH 7, 50 mM PIPES, 100 mM KCl). After 15 min, the reaction mixture was analyzed by gel electrophoresis. Protein samples were loaded in 2× Laemmli sample buffer (Bio-Rad 1610737) and resolved by SDS-PAGE (Bio-Rad, Any kD™ mini-PROTEAN® TGX Stain-Free™ protein gels, 4568126). The gel was visualized with an Azure Sapphire Biomolecular Imager for TAMRA (excitation 520 nm; emission 565 nm), which confirmed the formation of the desired BSA-CAP9-TAMRA conjugate. Analogous results were obtained with CAP9-TAMRA prepared with CAP9 and the TAMRA derivative in 4:1 molar ratio under similar reaction conditions.

Example 65: One-Pot Two-Step Labeling of GFP V150C with CAP9 and Tetramethyl Rhodamine Phenol Derivative

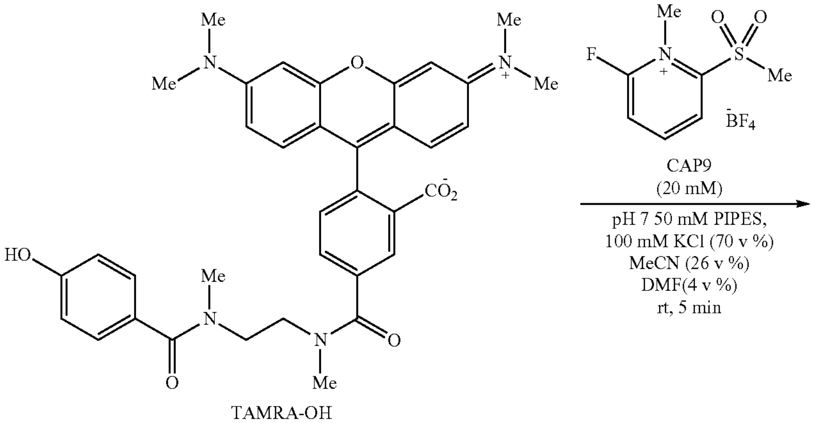

TAMRA-OH
(10 mM)

-continued

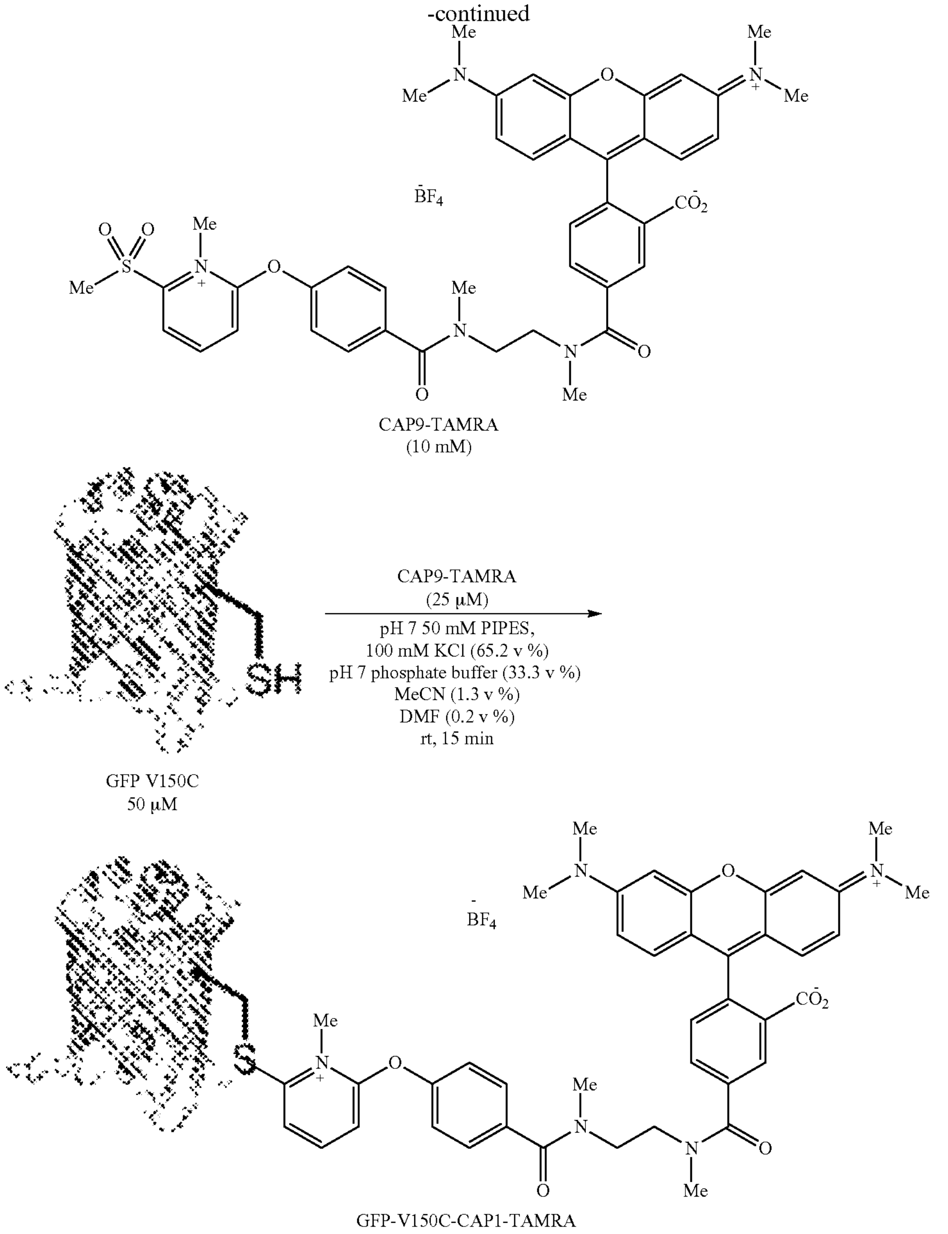

An aliquot of freshly prepared CAP9 (2 μL, 100 mM in MeCN) was added to a mixture of PIPES buffer (7 μL, pH 7, 50 mM PIPES, 100 mM KCl) and tetramethyl rhodamine phenol derivative (1 μL, 100 mM in MeCN/DMF, 63:37 v:v). The reaction was kept at room temperature for 5 min. An aliquot of this solution (1 μL, 100 mM) was diluted with water (19 μL) to give a 10 mM CAP9-TAMRA solution. An aliquot of the above CAP9-TAMRA solution (0.75 μL, 0.5 mM, 1.25 equiv.) was mixed with GFP V150C (5 μL, 60 μM in pH 7 phosphate buffer) in PIPES buffer (9.25 μL, pH 7, 50 mM PIPES, 100 mM KCl). After 15 min, the reaction mixture was analyzed by gel electrophoresis. Protein samples were loaded in 2× Laemmli sample buffer (Bio-Rad 1610737) and resolved by SDS-PAGE (Bio-Rad, Any kD™ mini-PROTEAN® TGX Stain-Free™ protein gels, 4568126). The gel was visualized with an Azure Sapphire Biomolecular Imager for GFP (excitation 488 nm; emission 518 nm) and TAMRA (excitation 520 nm; emission 565 nm), which confirmed the formation of the desired GFP-V150C-CAP9-TAMRA conjugate. Analogous results were obtained with CAP9-TAMRA prepared with CAP9 and TAMRA in 4:1 molar ratio under similar reaction conditions.

Quantification of the Reactivity of CAP1-a Toward Various Nucleophiles

In a typical experiment, an aliquot of the stock solution of CAP1-a in water was added to nucleophile in PIPES buffer or water. The progress of the reaction was monitored by UV-Vis spectrometer at suitable wavelength. The pseudo first order reaction rate constant was determined by plotting the ln value of the concentration of CAP1-a against the reaction time. The pseudo first order reaction rate constant thus obtained was plotted against the concentration of the nucleophile. The slope of this linear correlation is the second order reaction rate constant. CAP1-a was reacted separately with GSH, cysteine, N-acetylcysteine, and phenol.

Unexpectedly, each reaction proceeded at an exceptionally high second order reaction rate constant ($k_2$). The reaction between CAP1-a and GSH had a $k_2$ of $1.2 \times 10^2$ $M^{-1} \cdot S^{-1}$ at 25° C. and pH 7 in 50 mM PIPES. The $k_2$ for the reaction between CAP1-a and cysteine was $2.8 \times 10^2$ $M^{-1} \cdot S^{-1}$ under similar reaction conditions. On the other hand, the $k_2$ for the reaction between CAP1-a and water was only $4.5 \times 10^{-6}$ $M^{-1}$ $S^{-1}$, indicating the high stability of CAP1-a in water.

Quantification of the Reactivity of CAP Compounds Toward Various Nucleophiles

Following the study above, compounds CAP1-F, CAP2, and CAP4 each were reacted with either GSH or phenol in water or 50 mM PIPES at pH 7. Surprisingly, each reaction proceeded at an exceptionally high second order reaction rate constant ($k_2$). The reaction between CAP4 and GSH had a $k_2$ as high as $5.3 \times 10^4$ $M^{-1} \cdot S^{-1}$ at 25° C. and pH 7 in 50 mM PIPES.

On the other hand, the reaction between CAP4 and water is very slow, showing a $k_2$ of only $4.8\text{–}10^{-6}$ $M^{-1} \cdot S^{-1}$ at 25° C. and pH 7 in 50 mM PIPES. The slow reaction with water demonstrates that CAP compounds are stable in water.

In another study, compounds CAP1-b, CAP1-F, CAP2, CAP3, CAP4, and CAP5 each were reacted with either GSH in a 50 mM PIPES and 150 mM KCl aqueous solution at pH 7 and 25° C. Surprisingly, each reaction proceeded at a high rate. The reaction between CAP5 and GSH has a $k_2$ as high as $3.2 \times 10^5$ $M^{-1} \cdot S^{-1}$, $7 \times 10^9$ folds faster than its reaction with water under the same conditions. Similarly, the reactions between GSH and one of CAP1-b, CAP1-F, CAP2, CAP3, and CAP4 had a $k_2$ of, respectively, $1.2 \times 10^2$ $M^{-1} \cdot S^{-1}$, $3.5 \times 10$ $M^{-1} \cdot S^{-1}$, $2.4 \times 10$ $M^{-1} \cdot S^{-1}$, $9.8 \times 10^3$ $M^{-1} \cdot S^{-1}$, and $1.2 \times 10^5$ $M^{-1}$. $S^{-1}$.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention also can be made and used for modifying a substrate having a suitable functional group. Thus, other embodiments were also within the claims.

What is claimed is:

1. A pnictogen-containing heterocyclic compound of Formula (I):

(I)

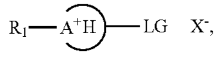

in which $R_1$ is $C_1$-$C_6$ alkyl, C4-C10 cycloalkyl, 5- to 8-membered heterocycloalkyl, aryl, or heteroaryl;

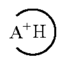

is a heterocyclic ring;

$A^+$ is a cationic quaternary pnictogen atom;

LG is a leaving group selected from the group consisting of halogen, aryloxy, $R_aO_2S$—, $R_bO_2S$—O—, $R_cOS$—, $R_dS(O)(NSO_2R_e)$—, and $R_fS(O)(N^+(CH_3)_2)$-, each of $R_a$, $R_b$, $R_c$, $R_d$, $R_e$, and $R_f$, independently, being $C_1$-$C_6$ alkyl, aryl, heteroaryl, halogen, alkoxy, or aryloxy;

$X^-$ is a counter anion selected from the group consisting of halide, polyhalide anion, perchlorate, hydroxide, peroxide, siloxide, sulfate, hydrogen sulfate, sulfite, disulfite, dithionate, dithionite, halosulfate, thiosulfate, persulfate, disulfate, sulfinate ($R'SO_2^-$), sulfonate ($R''SO_3^-$), bis(sulfonyl)imide ($(R'SO_2)_2N^-$), nitrate, nitrite, azide, cyanide, cyanate, thiocyanate, phosphate, metaphosphate, polyphosphate, hydrogen phosphate, dihydrogen phosphate, monohalophosphate, dihalophosphate, hexahalophosphate, organophosphonate ($R'P(O)(O^-)_2$ or $R'P(O)(OR^-)(O^-)$), organophosphate ($R'OP(O)(O)_2$ or $R'OP(O)(OR'')(O^-)$), arsenate, alkoxide, alkenoxide, aryloxide, carboxylate, percarboxylate, carbonate, bicarbonate, oxalate, borate, tetrahaloborate, tetraalkylborate, tetraarylborate, carborane, and combinations thereof, each of R' and R'', independently, being $C_1$-$C_6$ alkyl or aryl; and the number of net negative charges of X'' equals to that of the net positive charges of

.

2. The pnictogen-containing heterocyclic compound of claim 1, wherein the compound is a compound of Formula (II):

(II)

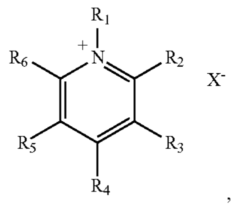, in which the cationic quaternary pnictogen atom is $N^+$ in Formula (II);

$R_1$ is $CH_3$, $CH_2CH_3$ or -L-Het$^+$;

each of $R_2$, $R_3$, $R_4$, $R_5$, and $R_6$, independently, is H, F, Cl, Br, I, $C_1$-$C_{10}$ alkoxy, $R_aO_2S$—, $R_bO_2S$—O—, $R_fS(O)(N^+(CH_3)_2)$—, halogenated aryl, halogenated heteroaryl, Het$^+$, or -L-Het$^+$, in which Het$^+$ is

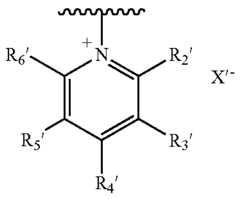,
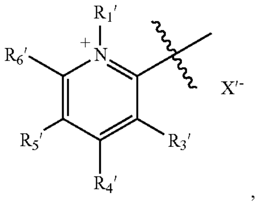,
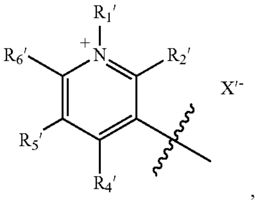,
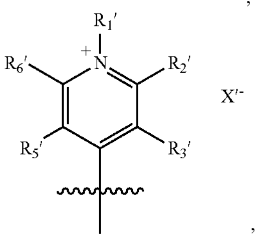,
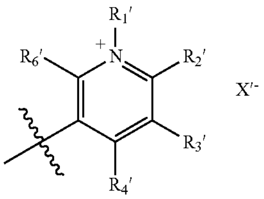, or
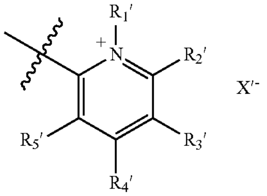;

$R_1$' is $CH_3$ or $CH_2CH_3$; each of $R_2$', $R_3$', $R_4$', $R_5$', and $R_6$', independently, is H, $NO_2$, F, Cl, Br, I, $R_a$'$O_2$S—, $R_b$'$O_2$S—O—, or $R_f$S(O)($N^+(CH_3)_2$)—; each of $R_a$', $R_b$', and $R_f$', independently, is $C_1$-$C_6$ alkyl or aryl; and X' is a counter anion selected from the group consisting of halide, polyhalide anion, perchlorate, hydroxide, peroxide, siloxide, sulfate, hydrogen sulfate, sulfite, disulfite, dithionate, dithionite, halosulfate, thiosulfate, persulfate, disulfate, sulfinate ($R'SO_2^-$), sulfonate ($R''SO_3^-$), bis(sulfonyl)imide ($(R'SO_2)_2N^-$), nitrate, nitrite, azide, cyanide, cyanate, thiocyanate, phosphate, metaphosphate, polyphosphate, hydrogen phosphate, dihydrogen phosphate, monohalophosphate, dihalophosphate, hexahalophosphate, organophosphonate ($R'P(O)(O^-)_2$ or $R'P(O)(OR'')(O^-)$), organophosphate ($R'OP(O)(O^-)_2$ or $R'OP(O)(OR'')(O^-)$), arsenate, alkoxide, alkenoxide, aryloxide, carboxylate, percarboxylate, carbonate, bicarbonate, oxalate, borate, tetrahaloborate, tetraalkylborate, tetraarylborate, carborane, and combinations thereof, each of R' and R'', independently, being $C_1$-$C_6$ alkyl or aryl; L is a linker selected from the group consisting of

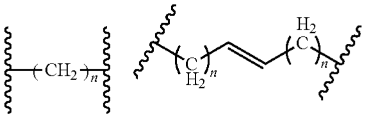
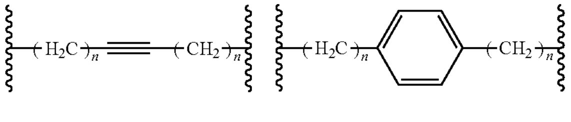

-continued

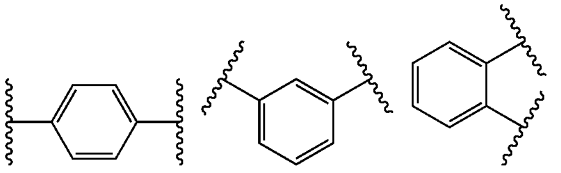
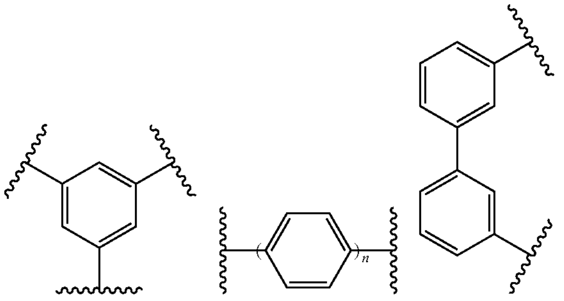
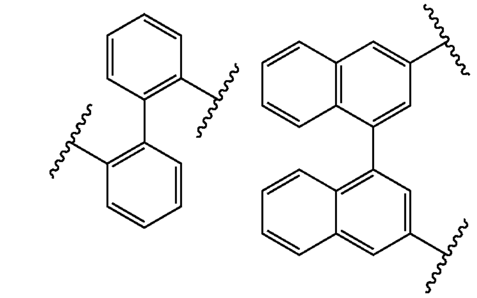
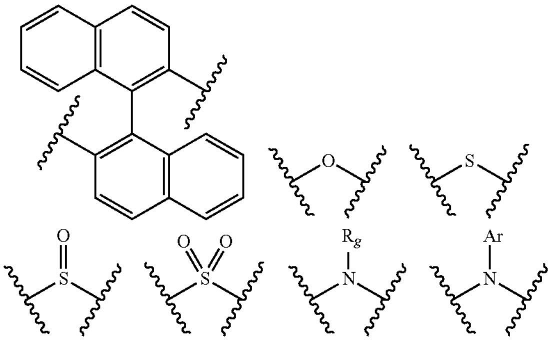
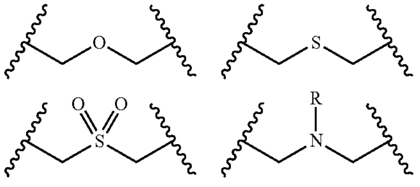
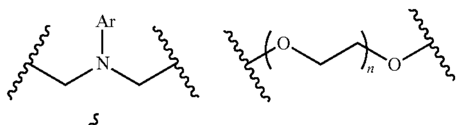
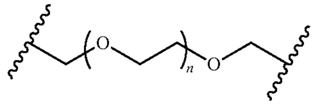 and
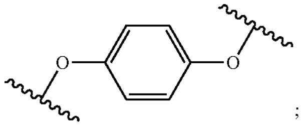;

n is an integer from 0 to 20; $R_g$ is $C_1$-$C_6$ alkyl; and Ar is aryl;

at least one of $R_2$, $R_3$, $R_4$, $R_5$, and $R_6$ is the leaving group that is F, Cl, Br, I, $R_aO_2S$—, or $R_bO_2S$—O—;

when $R_2$ is F, (i) $R_4$ is F, Cl, Br, I, $C_1$-$C_{10}$ alkoxy, $R_aO_2S$—, or $R_bO_2S$—O—, (ii) $R_5$ is $NO_2$, or (iii) one and only one of $R_3$, $R_4$, $R_5$, and $R_6$ is $Het^+$;

when $R_2$ is Cl, $R_5$ is H or $Het^+$; and when $R_4$ is-$SO_2CH_3$, (i) $R_2$ is F, Cl, Br, I, $C_1$-$C_{10}$ alkoxy, $R_aO_2S$—, or $R_bO_2S$—O—, or (ii) one and only one of $R_2$, $R_3$, $R_5$, and $R_6$ is $Het^+$.

3. The pnictogen-containing heterocyclic compound of claim 2, wherein at least one of $R_2$, $R_4$, and $R_6$ is the leaving group.

4. The pnictogen-containing heterocyclic compound of claim 3, wherein the leaving group is F or $CH_3O_2S$—.

5. The pnictogen-containing heterocyclic compound of claim 2, wherein $R_2$, being the leaving group, is $CH_3O_2S$—, and $R_4$ is H, $C_1$-$C_{10}$ alkoxy, or $Het^+$.

6. The pnictogen-containing heterocyclic compound of claim 2, wherein $R_1$ is methyl or ethyl.

7. The pnictogen-containing heterocyclic compound of claim 2, wherein $R_3$ or $R_5$ is $NO_2$.

8. The pnictogen-containing heterocyclic compound of claim 2, wherein the compound is a compound of Formula (III):

(III)

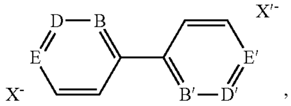, in which one and only one of B, D, and E is $N^+CH_3$ or $N^+CH_2CH_3$;

one and only one of B, D, and E is $CR_2$, $R_2$ being F, Cl, Br, I, $R_aO_2S$—, or $R_bO_2S$—O—;

one and only one of B, D, and E is $CR_{11}$, $R_{11}$ being $C_1$-$C_6$ alkyl, $C_1$-$C_6$ alkoxy, $C_2$-$C_6$ alkenyl, $C_2$-$C_6$ alkynyl, $C_1$-$C_6$ alkyl amino, $C_4$-$C_{10}$ cycloalkyl, $C_4$-$C_{10}$ cycloalkoxy, 5- to 8-membered heterocycloalkyl, 5- to 8-membered heterocycloalkoxy, aryl, aryloxy, heteroaryl, or heteroaryloxy;

one and only one of B', D', and E' is $N^+CH_3$ or $N^+CH_2CH_3$;

one and only one of B', D', and E' is $CR_2'$, $R_2'$ being F, Cl, Br, I, $R_a'O_2S$—, or $R_b'O_2S$—O—;

one and only one of B', D', and E' is $CR_{11}'$, $R_{11}'$ being $C_1$-$C_6$ alkyl, $C_1$-$C_6$ alkoxy, $C_2$-$C_6$ alkenyl, $C_2$-$C_6$ alkynyl, $C_1$-$C_6$ alkyl amino, $C_4$-$C_{10}$ cycloalkyl, $C_4$-$C_{10}$ cycloalkoxy, 5- to 8-membered heterocycloalkyl, 5- to 8-membered heterocycloalkoxy, aryl, aryloxy, heteroaryl, or heteroaryloxy; and $X'^-$ is a counter anion selected from the group consisting of halide, polyhalide anion, perchlorate, hydroxide, peroxide, siloxide, sulfate, hydrogen sulfate, sulfite, disulfite, dithionate, dithionite, halosulfate, thiosulfate, persulfate, disulfate, sulfinate ($R'SO_2^-$), sulfonate ($R''SO_3^-$), bis(sulfonyl)imide ($(R'SO_2)_2N^-$), nitrate, nitrite, azide, cyanide, cyanate, thiocyanate, phosphate, metaphosphate, polyphosphate, hydrogen phosphate, dihydrogen phosphate, monohalophosphate, dihalophosphate, hexahalophosphate, organophosphonate ($R'P(O)(O^-)_2$ or $R'P(O)(OR'')(O^-)$), organophosphate ($R'OP(O)(O^-)_2$ or $R'OP(O)(OR'')(O^-)$), arsenate, alkoxide, alkenoxide, aryloxide, carboxylate, percarboxylate, carbonate, bicarbonate, oxalate, borate, tetrahaloborate, tetraalkylborate, tetraarylborate, carborane, and combinations thereof, each of R' and R'', independently, being $C_1$-$C_6$ alkyl or aryl.

9. The pnictogen-containing heterocyclic compound of claim 8, wherein each of $R_2$ and $R_2'$, independently, is F or $CH_3O_2S$—.

10. The pnictogen-containing heterocyclic compound of claim 1, wherein the compound is a compound of Formula (IV):

(IV)

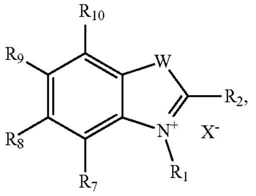

in which $R_1$ is $CH_3$ or $CH_2CH_3$;

$R_2$ is F, Cl, Br, I, $R_aO_2S$—, or $R_bO_2S$—O—;

each of $R_7$, $R_8$, $R_9$, and $R_{10}$, independently, is H or $C_1$-$C_6$ alkyl; and W is S or $NR_{11}$, Ru being $C_1$-$C_6$ alkyl.

11. The pnictogen-containing heterocyclic compound of claim 10, wherein $R_2$ is $CH_3O_2S$—.

12. The pnictogen-containing heterocyclic compound of claim 1, wherein the compound is a compound of Formula (V):

(V)

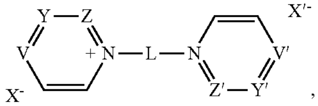, in which one and only one of V, Y, and Z is $CR_2$, $R_2$ being F, Cl, Br, I, $R_aO_2S$—, or $R_bO_2S$—O—;

the other two of V, Y, and Z is $CR_{11}$, $R_{11}$ being $C_1$-$C_6$ alkyl, $C_1$-$C_6$ alkoxy, $C_2$-$C_6$ alkenyl, $C_2$-$C_6$ alkynyl, $C_1$-$C_6$ alkyl amino, $C_4$-$C_{10}$ cycloalkyl, $C_4$-$C_{10}$ cycloalkoxy, 5- to 8-membered heterocycloalkyl, 5- to 8-membered heterocycloalkoxy, aryl, aryloxy, heteroaryl, or heteroaryloxy;

one and only one of V', Y', and Z' is $CR_2'$, $R_2'$ being F, Cl, Br, I, $R_a'O_2S$—, or $R_b'O_2S$—O—;

the other two of V', Y', and Z' is $CR_{11}'$, $R_{11}'$ being $C_1$-$C_6$ alkyl, $C_1$-$C_6$ alkoxy, $C_2$-$C_6$ alkenyl, $C_2$-$C_6$ alkynyl, $C_1$-$C_6$ alkyl amino, $C_4$-$C_{10}$ cycloalkyl, $C_4$-$C_{10}$ cycloalkoxy, 5- to 8-membered heterocycloalkyl, 5- to 8-membered heterocycloalkoxy, aryl, aryloxy, heteroaryl, or heteroaryloxy;

L is a linker selected from the group consisting of

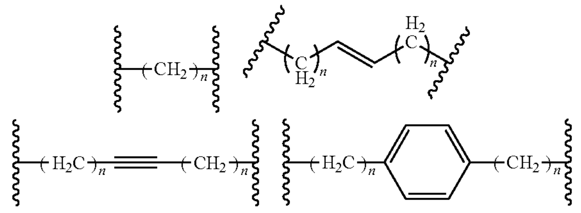

-continued

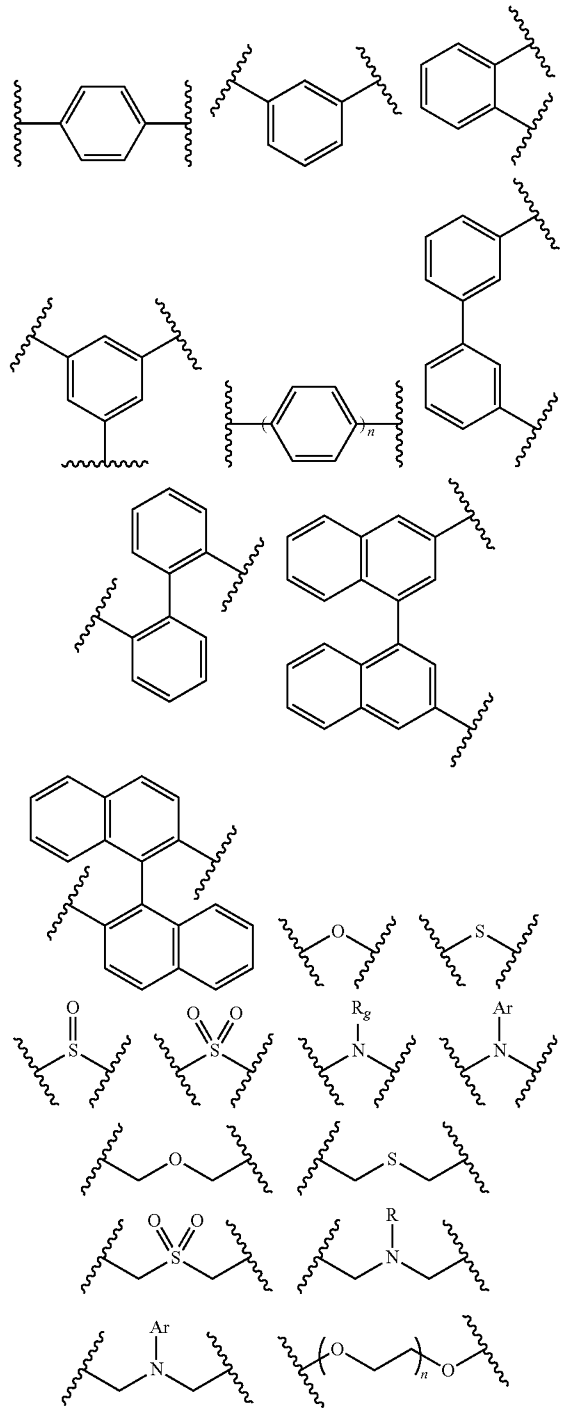

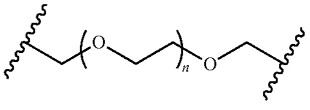

and

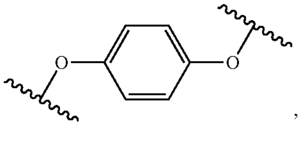

, n being an integer from 0 to 20, $R_g$ is $C_1$-$C_6$ alkyl, and Ar is aryl; and X'⁻ is a counter anion selected from the group consisting of halide, polyhalide anion, perchlorate, hydroxide, peroxide, siloxide, sulfate, hydrogen sulfate, sulfite, disulfite, dithionate, dithionite, halosulfate, thiosulfate, persulfate, disulfate, sulfinate ($R'SO_2^-$), sulfonate ($R''SO_3^-$), bis(sulfonyl)imide ($(R'SO_2^-)_2N$), nitrate, nitrite, azide, cyanide, cyanate, thiocyanate, phosphate, metaphosphate, polyphosphate, hydrogen phosphate, dihydrogen phosphate, monohalophosphate, dihalophosphate, hexahalophosphate, organophosphonate ($R'P(O)(O^-)_2$ or $R'P(O)(OR'')(O^-)$), organophosphate ($R'OP(O)(O^-)_2$ or $R'OP(O)(OR'')(O^-)$), arsenate, alkoxide, alkenoxide, aryloxide, carboxylate, percarboxylate, carbonate, bicarbonate, oxalate, borate, tetrahaloborate, tetraalkylborate, tetraarylborate, carborane, and combinations thereof, each of R' and R'', independently, being $C_1$-$C_6$ alkyl or aryl.

13. The pnictogen-containing heterocyclic compound of claim 1, wherein the compound is selected from the group consisting of:

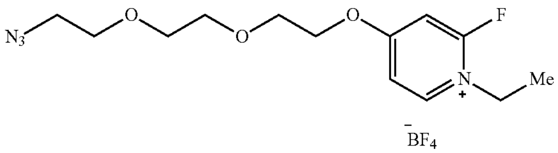

1-$N_3$

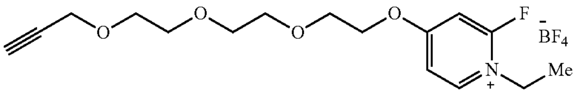

1-CCH

4

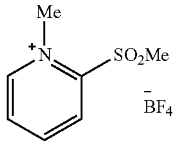

5

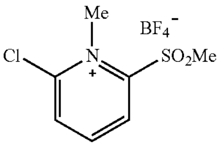

6

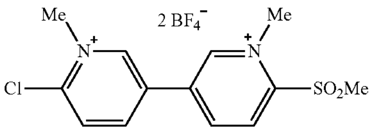

7

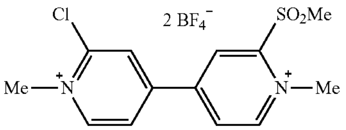

8

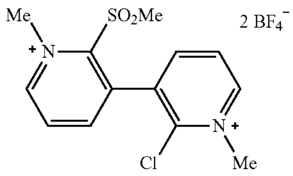

-continued

9

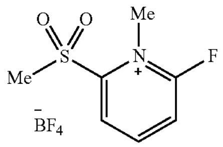

10

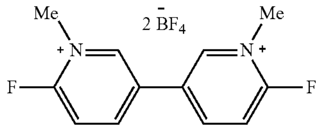

11

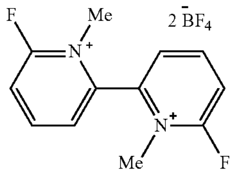

12

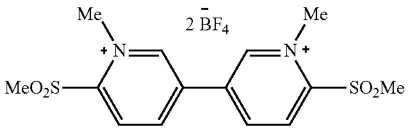

13

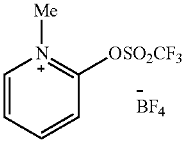

14

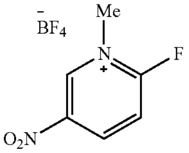

18

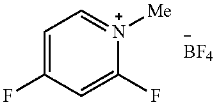

19

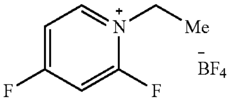

21

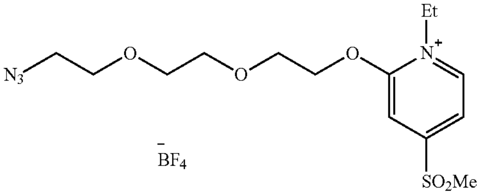

22

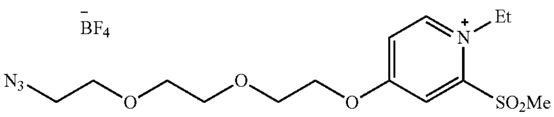

-continued

23

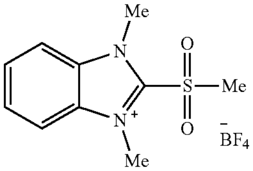

24

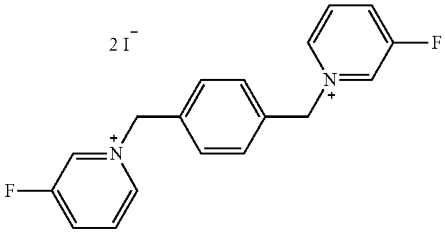

25

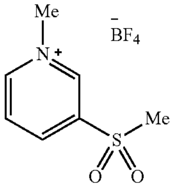

26

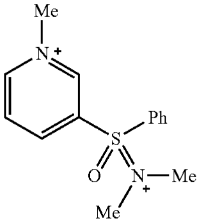

and

27

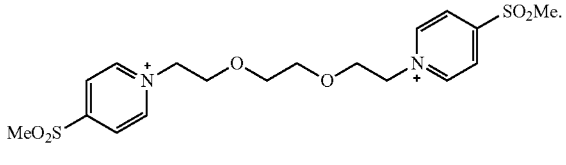

14. The pnictogen-containing heterocyclic compound of claim 13, wherein the compound is one of Compounds 4-9, 21, and 22.

15. A conjugated biomolecule comprising:

(i) a biomolecule moiety derived from a biomolecule, and (ii) a pnictogen-containing heterocyclic moiety derived from a pnictogen-containing heterocyclic compound of claim 1, wherein the biomolecule is an amino acid, a peptide, a protein, a deoxyribonucleic acid or a derivative thereof, a ribonucleic acid or a derivative thereof, a peptoid, or poly(amino acid), each having a functional group selected from the group consisting of hydroxyl, thiol, selenol, and tellurol, and the biomolecule moiety is linked to the pnictogen-containing heterocyclic moiety via a covalent bond formed by substitution of the leaving group in the pnictogen-containing heterocyclic compound by the functional group in the biomolecule.

16. The conjugated biomolecule of claim 15, further comprising a therapeutic moiety derived from a therapeutic agent selected from the group consisting of an anticancer agent, a therapeutically active peptide and protein, a medication for a neurological disorder, a molecular scaffold for targeted drug delivery, or a radioactive tracer, wherein the therapeutic moiety is linked to the pnictogen-containing heterocyclic moiety via a covalent bond, the therapeutic agent contains a functional group selected from the group consisting of hydroxyl, thiol, selenol, and tellurol, and the pnictogen-containing heterocyclic compound has two leaving groups.

17. A pharmaceutical composition comprising a conjugated biomolecule of claim 15 and a pharmaceutically acceptable carrier thereof.

* * * * *